(12) United States Patent
Sivan et al.

(10) Patent No.: US 11,937,943 B2
(45) Date of Patent: *Mar. 26, 2024

(54) DETECTION OF PHYSICAL ABUSE OR NEGLECT USING DATA FROM EAR-WEARABLE DEVICES

(71) Applicant: Starkey Laboratories, Inc., Eden Prairie, MN (US)

(72) Inventors: Matan Sivan, Tel Aviv (IL); Nitzan Bornstein, Tel Aviv (IL); Justin Burwinkel, Eden Prairie, MN (US); Roy Talman, Herzliya (IL); Neta Aviel, Tel-Mond (IL)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/186,568

(22) Filed: Mar. 20, 2023

(65) Prior Publication Data

US 2023/0225675 A1 Jul. 20, 2023

Related U.S. Application Data

(63) Continuation of application No. 16/777,525, filed on Jan. 30, 2020, now Pat. No. 11,607,170.

(Continued)

(51) Int. Cl.
*A61B 5/00* (2006.01)
*A61B 5/0205* (2006.01)
(Continued)

(52) U.S. Cl.
CPC .......... *A61B 5/6815* (2013.01); *A61B 5/0002* (2013.01); *A61B 5/0024* (2013.01);
(Continued)

(58) Field of Classification Search
CPC ........ H04R 25/55; H04R 3/005; G16H 50/30; A61B 5/165; A61B 5/7264; A61B 5/00;
(Continued)

(56) References Cited

U.S. PATENT DOCUMENTS 9,510,765 B2 12/2016 Greder
10,096,319 B1 10/2018 Jin et al.
(Continued)

FOREIGN PATENT DOCUMENTS

GB 2533430 A 6/2016
WO 2010/108287 A1 9/2010
(Continued)

OTHER PUBLICATIONS

Berke et al., "Objective Measurement of Sociability and Activity: Mobile Sensing in the Community", Annals of Family Medicine, vol. 9, No. 4, Jul./Aug. 2011, pp. 344-350.

(Continued)

*Primary Examiner* — Yosef K Laekemariam
(74) *Attorney, Agent, or Firm* — Shumaker & Sieffert, P.A.

(57) ABSTRACT

A system may obtain a set of features characterizing a segment of inertial measurement unit (IMU) data generated by an IMU of an ear-wearable device. The system may apply a machine learning model (MLM) that takes the features characterizing the segment of the IMU data as input. The system may determine, based on output values produced by the MLM, whether a user of the ear-wearable device has potentially been subject to physical abuse. The system may then perform an action in response to determining that the user of the ear-wearable device has potentially been subject to physical abuse.

18 Claims, 18 Drawing Sheets

Related U.S. Application Data

(60) Provisional application No. 62/800,227, filed on Feb. 1, 2019.

(51) Int. Cl.
  *A61B 5/16*     (2006.01)
  *A61B 5/369*    (2021.01)
  *G06N 3/08*     (2023.01)
  *G06N 20/00*    (2019.01)
  *H04R 3/00*     (2006.01)
  *A61B 5/024*    (2006.01)

(52) U.S. Cl.
  CPC .......... *A61B 5/0205* (2013.01); *A61B 5/165* (2013.01); *A61B 5/486* (2013.01); *A61B 5/742* (2013.01); *G06N 3/08* (2013.01); *G06N 20/00* (2019.01); *H04R 3/005* (2013.01); *A61B 5/02438* (2013.01); *A61B 5/369* (2021.01); *A61B 2562/0219* (2013.01); *A61B 2562/0223* (2013.01)

(58) Field of Classification Search
  CPC ..... A61B 5/369; A61B 5/6815; A61B 5/0002; A61B 5/0024; A61B 5/0205; A61B 5/486; A61B 5/742; A61B 5/02438; A61B 2562/0219; A61B 2562/0223; G06N 3/08; G06N 20/00
  See application file for complete search history.

(56) References Cited

U.S. PATENT DOCUMENTS

| | | | |
|---|---|---|---|
| 11,317,863 B2 | 5/2022 | Xu et al. | |
| 2013/0343584 A1 | 12/2013 | Bennett et al. | |
| 2014/0249379 A1 | 9/2014 | Proud | |
| 2014/0278229 A1 | 9/2014 | Hong et al. | |
| 2017/0143246 A1 | 5/2017 | Flickinger | |
| 2018/0228404 A1 | 8/2018 | Bhunia et al. | |
| 2018/0233018 A1* | 8/2018 | Burwinkel | A61B 5/1117 |
| 2018/0338046 A1* | 11/2018 | Hanabusa | H04M 11/045 |
| 2018/0358117 A1 | 12/2018 | Neagle | |
| 2019/0253812 A1 | 8/2019 | Gallégo | |
| 2020/0205746 A1 | 7/2020 | Burwinkel et al. | |
| 2020/0245869 A1 | 8/2020 | Sivan et al. | |
| 2020/0268315 A1 | 8/2020 | Burwinkel et al. | |

FOREIGN PATENT DOCUMENTS

| | | | | |
|---|---|---|---|---|
| WO | WO 2010/108287 | * | 9/2010 | A61B 5/145 |
| WO | 2012006549 A2 | | 1/2012 | |
| WO | 2014163358 A1 | | 10/2014 | |
| WO | 2021030585 A1 | | 2/2021 | |

OTHER PUBLICATIONS

Gierveld et al., "A 6-Item Scale for Overall, Emotional, and Social Loneliness", Research on Aging, vol. 28, No. 5, Sep. 2006, pp. 582-598.

Manabe et al., "Earphones to Perform Gaze Detection for Wearable Interfaces", DOCOMO Technical Journal vol. 12, No. 3, 2010, pp. 12-17 (Applicant points out, in accordance with MPEP 609.04(a), that the year of publication, 2010, is sufficiently earlier than the effective U.S. filing date, so that the particular month of publication is not in issue.).

Noury et al., "Use of electrical devices reveals our well being", 33rd Annual International Conference of the IEEE EMBS, Aug./Sep. 2011, pp. 1769-1772.

Prosecution History from U.S. Appl. No. 16/777,525, dated May 31, 2022 through Nov. 23, 2022, 32 pp.

Weinstein et al., "Relating Hearing Aid Use to Social and Emotional Loneliness in Older Adults", American Journal of Audiology, Mar. 2016, pp. 1-8.

Communication pursuant to Article 94(3) EPC from counterpart European Application No. 20708984.8 dated Aug. 31, 2023, 6 pp.

* cited by examiner

DETECTION OF PHYSICAL ABUSE OR NEGLECT USING DATA FROM EAR-WEARABLE DEVICES

This application is a continuation of U.S. patent application Ser. No. 16/777,525, filed Jan. 30, 2020, which claims the benefit of U.S. Provisional Patent Application 62/800,227, filed Feb. 1, 2019, the entire content of each of which is incorporated herein by reference.

TECHNICAL FIELD

This disclosure relates to ear-wearable devices.

BACKGROUND

In many people, hearing loss is a gradual process that occurs over many years. As a result, many people grow accustomed to living with reduced hearing without recognizing the auditory experiences and opportunities they are missing. For example, a person might not realize how much less conversation he or she engages in due to his or her hearing loss. As a result of hearing loss, reduced audibility, reduced social interaction, and communication pathology, patients may also experience follow-on effects such as dementia, depression, increased risk for falling and generally poorer health. It has further been noted that vulnerable people, such as those with memory loss or dementia, are victims of physical abuse with disturbing regularity.

SUMMARY

Among other techniques, this disclosure describes techniques for improving efficiency of measuring the social benefit of wearing an ear-wearable device. As described herein, a wellness evaluation system may determine, based on data generated by a first set of sensors powered by one or more batteries of one or more ear-wearable devices, that a user is currently in an environment that includes human-directed communication signals. The batteries may also provide a first amount of power to a second set of sensors. The second set of sensors includes at least one sensor that is not included in the first set of sensors. The second set of sensors may be activated such that the one or more batteries provide a second amount of power greater than the first amount of power to the second set of sensors. Furthermore, in some examples, the wellness evaluation system may determine, based on data generated by the second set of sensors, whether the user has satisfied a target level of a wellness measure. If the user has not satisfied the target level of the wellness measure, the wellness evaluation system may perform an action to encourage the user to perform one or more activities to increase an achieved level of the wellness measure. In some examples, the wellness evaluation system may generate statistical data based on the data generated by the second set of sensors.

In one example, this disclosure describes a method comprising: determining, by one or more processing circuits, based on data generated by a first set of sensors powered by one or more batteries of one or more ear-wearable devices, that a user of the one or more ear-wearable device is currently in an environment that includes human-directed communication signals, wherein the batteries provide a first amount of power to a second set of one or more sensors, wherein the second set of sensors includes at least one sensor that is not included in the first set of sensors; in response to determining that the user is currently in the environment that includes human-directed communication signals, activating, by the one or more processing circuits, the second set of sensors such that the one or more batteries provides a second amount of power greater than the first amount of power to the second set of sensors; determining, by the one or more processing circuits, based on data generated by the second set of sensors, whether the user has satisfied a target level of a wellness measure; and based on a determination that the user has not satisfied the target level of the wellness measure, performing, by the one or more processing circuits, an action to encourage the user to perform one or more activities to increase an achieved level of the wellness measure, the achieved level of the wellness measure being a level of the wellness measure achieved by the user.

In another example, this disclosure describes a system comprising: a data storage system configured to store data generated by a first set of sensors powered by one or more batteries of one or more ear-wearable devices; and one or more processing circuits configured to: determine, based on the data generated by the first set of sensors, that a user of the one or more ear-wearable devices is currently in an environment that includes human-directed communication signals, wherein the batteries provide a first amount of power to a second set of one or more sensors, wherein the second set of sensors includes at least one sensor that is not included in the first set of sensors; in response to determining that the user is currently in the environment that includes human-directed communication signals, activate the second set of sensors such that the one or more batteries provide a second amount of power greater than the first amount of power to the second set of sensors, wherein the second set of sensors includes at least one sensor that is not included in the first set of sensors; determine, based on data generated by the second set of sensors, whether the user has satisfied a target level of a wellness measure; and based on a determination that the user has not satisfied the target level of the wellness measure, perform an action to encourage the user to perform one or more activities to increase an achieved level of the wellness measure, the achieved level of the wellness measure being a level of the wellness measure achieved by the user.

In another example, this disclosure describes a method comprising: determining, by one or more processing circuits, first statistical data based on data generated by a first set of sensors powered by one or more batteries of one or more ear-wearable devices, wherein the batteries provide a first amount of power to a second set of one or more sensors, wherein the second set of sensors includes at least one sensor that is not included in the first set of sensors; determining, by the one or more processing circuits, based on the first statistical data, to activate the second set of sensors such that the one or more batteries provide a second amount of power greater than the first amount of power to the second set of sensors; and determining, by the one or more processing circuits, based on data generated by the second set of sensors, second statistical data regarding the user. In another example, this disclosure describes a system comprising a data storage system configured to store data generated by a first set of sensors powered by one or more batteries of one or more ear-wearable devices; and one or more processing circuits configured to perform the method of the previous example.

In other examples, this disclosure describes systems comprising means for performing these examples and computer-readable storage medium having instructions stored thereon that, when executed, cause one or more processing circuits to perform the methods of these examples.

In other examples, this disclosure describes a method comprising obtaining, by one or more processing circuits, a set of features characterizing a segment of inertial measurement unit (IMU) data generated by an IMU of an ear-wearable device; applying, by the one or more processing circuits, a machine learning model (MLM) that takes the features characterizing the segment of the IMU data as input; determining, by the one or more processing circuits, based on output values produced by the MLM, whether a user of the ear-wearable device has potentially been subject to physical abuse; and performing, by the one or more processing circuits, an action in response to determining that the user of the ear-wearable device has potentially been subject to the type of physical abuse.

In another example, this disclosure describes a system comprising: a data storage system configured to a set of features characterizing a segment of inertial measurement unit (IMU) data generated by an IMU of an ear-wearable device; and one or more processing circuits configured to: apply a machine learning model (MLM) that takes the features characterizing the segment of the IMU data as input; determine, based on output values produced by the MLM, whether a user of the ear-wearable device has potentially been subject to physical abuse; and perform an action in response to determining that the user of the ear-wearable device has potentially been subject to physical abuse.

In another example, this disclosure describes a system comprising: means for obtaining a set of features characterizing a segment of inertial measurement unit (IMU) data generated by an IMU of an ear-wearable device; means for applying a machine learning model (MLM) that takes the features characterizing the segment of the IMU data as input; means for determining, based on output values produced by the MLM, whether a user of the ear-wearable device has potentially been subject to a type of physical abuse in the plurality of the types of physical abuse; and means for performing an action in response to determining that the user of the ear-wearable device has potentially been subject to the type of physical abuse.

In another example, this disclosure describes a computer-readable data storage medium having instructions stored thereon that, when executed, cause one or more processing circuits to: obtain a set of features characterizing a segment of inertial measurement unit (IMU) data generated by an IMU of an ear-wearable device; apply a machine learning model (MLM) that takes the features characterizing the segment of the IMU data as input; determine, based on output values produced by the MLM, whether a user of the ear-wearable device has potentially been subject to a type of physical abuse in the plurality of the types of physical abuse; and perform an action in response to determining that the user of the ear-wearable device has potentially been subject to the type of physical abuse.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1:
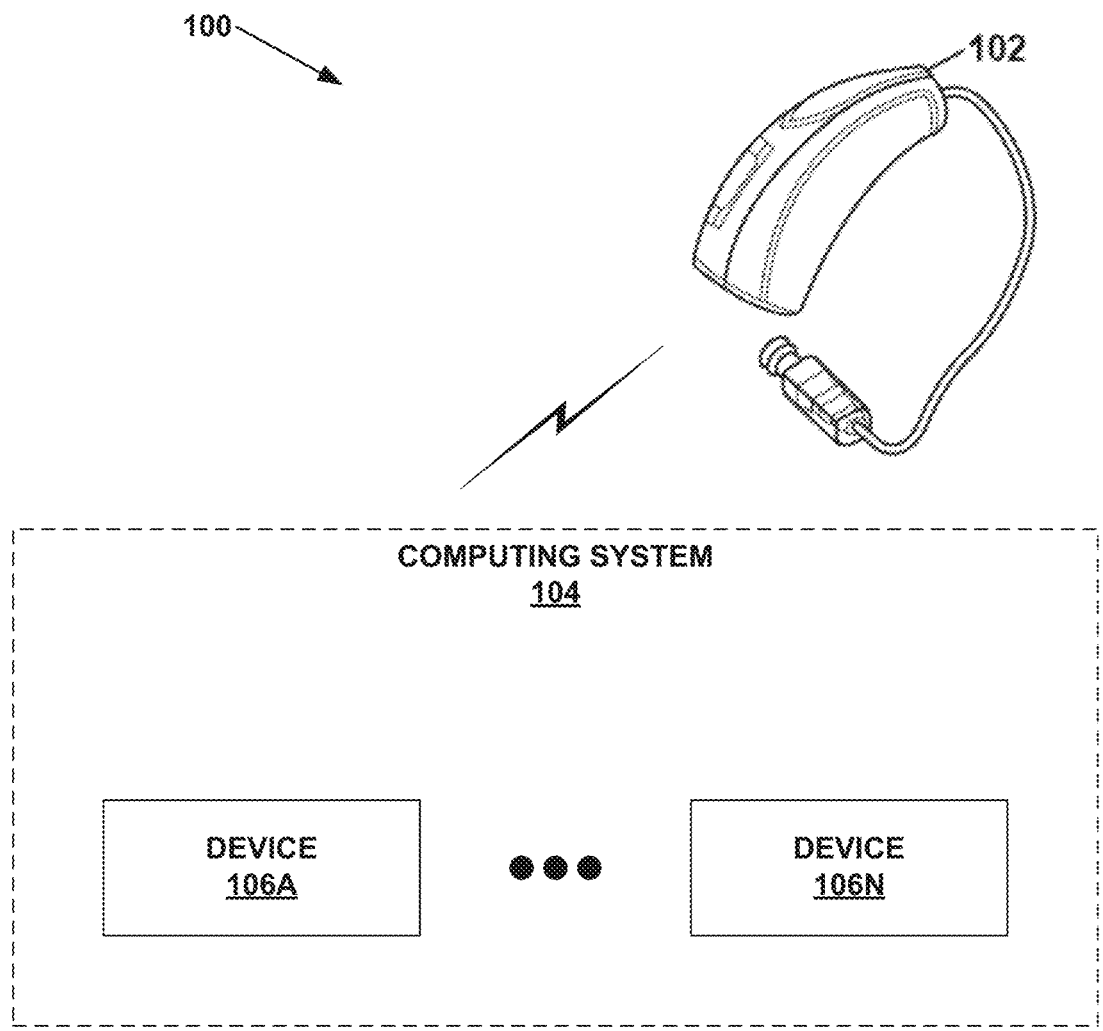
FIG. 1 illustrates an example system for efficient wellness measurement, using an ear-wearable device, implemented in accordance with one or more techniques of this disclosure.

FIG. 1 illustrates an example system 100 for efficient wellness measurement, using an ear-wearable device, implemented in accordance with one or more aspects of this disclosure. In the example of FIG. 1, system 100 includes one or more ear-wearable device(s) 102 and a computing system 104. Computing system 104 includes one or more computing devices. For instance, in the example of FIG. 1, computing system 104 comprises devices 106A through 106N (collectively, "devices 106"). Devices 106 may include various types of devices, such as one or more mobile phones, tablet computers, personal computers, server devices, cloud computers, mesh networks, and/or other types of computing devices.

Ear-wearable device(s) 102 may comprise one or more of various types of devices configured to provide hearing assistance. For example, ear-wearable device(s) 102 may comprise one or more hearing assistance devices. In another example, ear-wearable device(s) 102 may comprise one or more Personal Sound Amplification Products (PSAPs). In another example, ear-wearable device(s) 102 may comprise one or more cochlear implants, cochlear implant magnets, cochlear implant transducers, and cochlear implant processors. In another example, ear-wearable device(s) 102 may comprise one or more so-called "hearables" that provide various types of functionality. In other examples, ear-wearable device(s) 102 may comprise other types of devices that are wearable in, on, or in the vicinity of the user's ears. In other examples, ear-wearable device(s) 102 may comprise other types of devices that are implanted or otherwise osseointegrated with the user's skull; wherein the ear-wearable device is able to facilitate stimulation of the wearer's ears via the bone conduction pathway. The techniques of this disclosure are not limited to the form of ear-wearable device shown in FIG. 1.

Ear-wearable device(s) 102 may be configured to communicate wirelessly with each other. Furthermore, at least one of ear-wearable device(s) 102 is configured to communicate with one or more devices 106 in computing system 104. For example, ear-wearable device(s) 102 and a device in computing system 104 may communicate wirelessly using a Near-Field Magnetic Induction (NFMI) technology, a 900 MHz technology, a BLUETOOTH™ technology, a WI-FI™ technology, or another type of wireless communication technology. In the example of FIG. 1, one or more of ear-wearable device(s) 102 may communicate wirelessly with device 106A, which may, for example, be the user's mobile phone. In some examples, ear-wearable device(s) 102 may use a 2.4 GHz frequency band for wireless communication with one or more of devices 106 or other computing devices.

Devices 106 of computing system 104 may communicate with each other via a communication network. The communication network may include one or more of various types of communication networks, such as cellular data networks, WI-FI™ networks, mesh networks, the Internet, and so on. For example, device 106A (e.g., a mobile phone) may communicate with device 106N (e.g., a server device) to store data to and retrieve data from device 106N. Thus, in this example, from the perspective of device 106A and ear-wearable device(s) 102, the server device may be considered to be in the "cloud."

Ear-wearable device(s) 102 may implement a variety of features that help a user of ear-wearable device(s) 102 hear better. For example, ear-wearable device(s) 102 may amplify the intensity of incoming sound, amplify the intensity of certain frequencies of the incoming sound, translate or compress frequencies of the incoming sound, and/or perform other functions to improve the hearing of the user. In another example, ear-wearable device(s) 102 may implement a directional processing mode in which ear-wearable device(s) 102 selectively amplify sound originating from a particular direction (e.g., to the front of the user) while potentially fully or partially canceling sound originating from other directions. In other words, a directional processing mode may selectively attenuate off-axis unwanted sounds. The directional processing mode may help users understand conversations occurring in crowds or other noisy environments. In some examples, ear-wearable device(s) 102 may reduce noise by canceling out or attenuating certain frequencies. Furthermore, in some examples, ear-wearable device(s) 102 may help a user enjoy audio media, such as music or sound components of visual media, by outputting sound based on audio data wirelessly transmitted to ear-wearable device(s) 102.

A person may lose their hearing gradually over the course of many years. Because changes in hearing may be a slow process, a person who is gradually losing his or her hearing may grow accustomed to living with impaired hearing and not realize the value added to the person's life by being able to fully access the auditory environment. For instance, the person may not realize how much less time he or she spends in conversation or enjoying audio media because of the person's hearing loss. This may remain true even after a person acquires an ear-wearable device, such as a hearing-assistance device. That is, because a person having a hearing-assistance device does not always wear the hearing-assistance device, the person may not realize the extent to which the hearing-assistance device enhances his or her life while wearing the hearing-assistance device as opposed to when the person is not wearing the hearing-assistance device.

Furthermore, research has shown that people who more frequently interact with others and their environments and people who are physically active tend to have better cognitive skills and better emotional health, both of which may lead to better health outcomes. Thus, being exposed to a diverse set of auditory situations or other communication situations while maintaining a level of physical activity may help the user achieve better health outcomes. However, depression, loneliness, physical inactivity, and an increased risk for falling may be more common among people who seldom converse with others or who are victims of abuse or neglect. This problem may be especially acute for older people, who are more likely to have hearing loss.

However, not all auditory or communication situations in which a user is engaged are equally indicative of the user's actual level of social engagement. For example, passively listening to the television is not associated with the same level of social engagement as engaging in extended discussions with multiple people in diverse locations. In another example, sitting in a noisy restaurant without participating in a conversation may be associated with a less positive impact on the user's cognitive and emotional health than being engaged in the conversation while at the same restaurant. In another example, engaging in conversations where the user speaks in full, complex sentences may have more positive impacts than conversations where the user speaks only in one- or two-word utterances. In another example, engaging in conversations where the user expresses various emotions may have more positive impacts than conversations where the user speaks without discernable emotional intent. In yet another example, engaging in conversations where the user communicates using multiple languages may have more positive impacts than conversations where the user communicates in only one language. This disclosure refers to communication situations that are more likely to have positive impacts on the user's cognitive and emotional health as higher-quality communication situations. Similarly, this disclosure refers to communication situations that are less likely to have positive impacts on the user's cognitive and emotional health as lower-quality communication situations.

It may be challenging to distinguish higher-quality communication situations from lower-quality communication situations. Furthermore, it may be challenging to determine what actions to take based on the user's perceived level of social engagement. The challenges of distinguishing higher-quality communication situations from lower-quality communication situations may be especially pronounced in resource-limited devices such as ear-wearable devices. For instance, collecting the needed information and performing the necessary determinations may consume significant amounts of power from the relatively small batteries of ear-wearable device(s) 102.

This disclosure describes techniques for using data generated at least in part by a user's ear-wearable devices to evaluate and act upon the user's achieved levels of one or more wellness measures. Examples of wellness measures may include measures of social engagement, measures of physical activity, and other aspects of the user's physical and mental wellness. As described herein, use of the techniques may reduce the amount of power consumed in evaluating the user's achieved level of one or more wellness measures. This, in turn, may allow for the determination of more accurate achieved levels of the one or more wellness measures.

With reference to the example of FIG. 1, one or more of ear-wearable device(s) 102 includes a set of sensors. For example, each of ear-wearable device(s) 102 may include one or more microphones. In some examples, one or more of ear-wearable device(s) 102 includes a location sensor, such as a satellite-based radio-navigation system sensor, such as a global positioning system (GPS) sensor. In some examples, one or more of ear-wearable device(s) 102 include magnetic sensors, telecoils, heart rate sensors, electroencephalogram (EEG) sensors, and/or other types of sensors.

As described in greater detail elsewhere in this disclosure, a wellness evaluation system may use data generated by the sensors to generate output. For instance, in some examples, the wellness evaluation system may use data generated by the sensors to determine levels of one or more wellness measures that have been achieved by a user of ear-wearable device(s) 102. In such examples, the wellness evaluation system may use the levels of the one or more wellness evaluation measures to generate the outputs. Such wellness measures may include measures of social engagement, measures of physical activity, and/or measures based on combinations of social engagement and physical activity. For instance, a measure of the complexity of the user's social interactions is one example of a measure of social engagement. The measure of the complexity of the user's social complexity may be based on the duration of time that the user is engaged in conversations with other people in which the user speaks in complex sentences or utterances.

The wellness evaluation system may generate various types of output based on the achieved levels of the one or more wellness measures achieved by the user. In another example, the wellness evaluation system may generate notifications to the user. In some examples, the wellness evaluation system may generate data for presentation to individuals other than the user of ear-wearable device(s) 102. For instance, the wellness evaluation system may provide information regarding achieved levels of wellness measures to one or more persons other than the user of ear-wearable device(s) 102. For instance, the wellness evaluation system may generate information for presentation to family members or healthcare providers (e.g., audiologists, speech-language pathologists, physicians, nurses, attendants, etc.) of the user of ear-wearable device(s) 102.

In some examples, the wellness evaluation system may use data generated by the sensors to generate statistical data. The statistical data may include various types of information that relate to the user's wellness but are not necessarily in the form of a level of a wellness measure. For example, the wellness evaluation system may generate, based on the data generated by the sensors, statistical data for use in risk prediction models. For instance, in this example, the wellness evaluation system may generate information utilized by an operatively connected processor that is further adapted to calculate the likelihood of a future risk, e.g., the techniques described in U.S. Patent Publication No. 2018/0228404 A1, filed Dec. 29, 2017, entitled FALL PREDICTION SYSTEM AND METHOD OF USING SAME.

A set of one or more processing circuits may implement the wellness evaluation system. In different examples, the set of processing circuits may be distributed among ear-wearable device(s) 102 and devices 106 of computing system 104 in various ways. For instance, in some examples, ear-wearable device(s) 102 may include all of the processing circuits that implement the wellness evaluation system, one of devices 106 may include all of the processing circuits that implement the wellness evaluation system, or multiple devices 106 of computing system 104 may include all of the processing circuits that implement the wellness evaluation system. In another example, some of the processing circuits that implement the wellness evaluation system are in one or more of ear-wearable device(s) 102 and some of the processing circuits that implement the wellness evaluation system are in one or more of devices 106 of computing system 104.

Another challenge in the evaluation of levels of wellness measures achieved by the user of ear-wearable device(s) 102 and generation of statistical data is how to protect the data used to evaluate the achieved levels of the wellness measures and generate the statistical data. For instance, a user may be uncomfortable with the idea of data indicating the user's location being sent to and stored at a remote computing system. In another example, a user may be uncomfortable with the idea of recordings of their conversations being sent to and stored a remote server for use in evaluating the levels of the wellness measures achieved by the user. At the same time, continuously evaluating the achieved levels of the wellness measures or generating statistical data at ear-wearable device(s) 102 may consume considerable amounts of battery power, which may be in limited supply in ear-wearable device(s) 102. However, wirelessly transmitting data from ear-wearable device(s) 102 to computing system 104 would also be a considerable drain on the battery power of ear-wearable device(s) 102.

Hence, in accordance with some examples of this disclosure, the wellness evaluation system may be configured to selectively activate and deactivate particular sensors that generate data that the wellness evaluation system uses in determining achieved levels of the wellness measures and/or generating statistical data. Selectively activating particular sensors may help conserve battery power. Additionally, selectively activating particular sensors may help reduce the generation of data that could pose privacy concerns and whose wireless transmission may cause further drains on battery power. Furthermore, in some examples, to avoid power consumption associated with continual evaluation of the levels and/or generation of statistical data, the wellness evaluation system may refrain from performing more complex operations to evaluate levels of certain wellness measures and/or generate statistical data until levels of other wellness measures or other data cross particular thresholds.

In some other examples, to avoid the power consumption and privacy concerns associated with wirelessly transmitting sensor data, the wellness evaluation system may perform one or more levels of signal processing to extract features of, compress, simplify, deconstruct, encrypt, or otherwise process the data.

Furthermore, in some examples, ear-wearable device(s) 102 may include a left ear-wearable device and a right ear-wearable device. The left ear-wearable device and the right ear-wearable device may have one or more pairs of sensors that belong to the same type of sensor. For example, both the left ear-wearable device and the right ear-wearable device may have a respective photoplethysmography (PPG) sensor. In accordance with a technique of this disclosure, the wellness evaluation system may conserve power by duty cycling sensors between right and left ear-wearable devices. For instance, rather than having both a PPG sensor in the left ear-wearable device and a PPG sensor in the right ear-wearable device be activated at the same time, the wellness evaluation system may switch between the PPG sensors in the left and right ear-wearable devices being activated such that when one of the PPG sensors is active, the other PPG sensor is inactive. Duty cycling between sensors in a pair of sensors may result in less accuracy but may conserve power. Any suitable duty-cycling schemes may be utilized.

Figure 2:
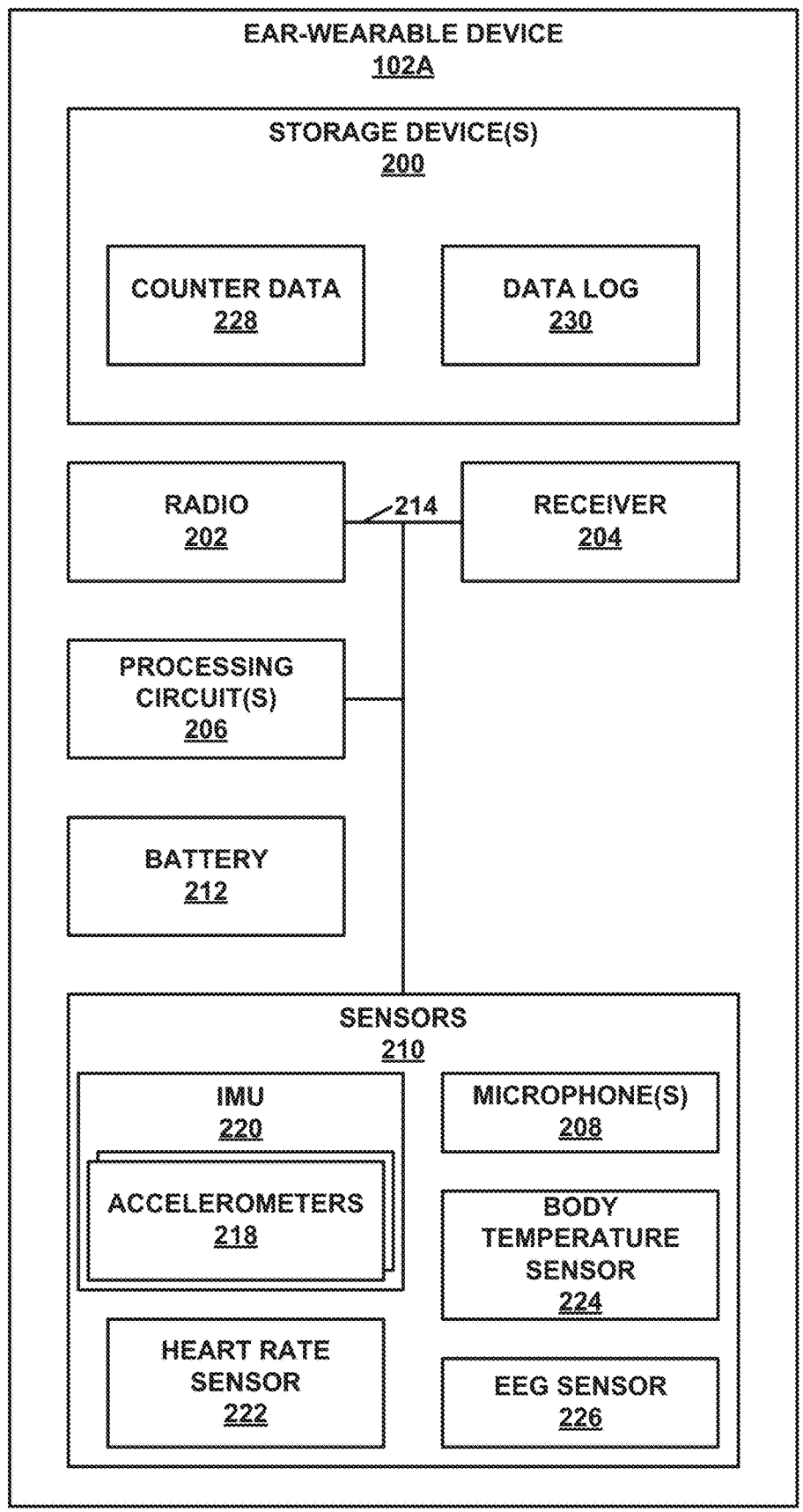
FIG. 2 is a block diagram illustrating example components of an ear-wearable device, in accordance with one or more aspects of this disclosure.

FIG. 2 is a block diagram illustrating example components of an ear-wearable device 102A, in accordance with one or more aspects of this disclosure. Ear-wearable device 102A may be one of ear-wearable device(s) 102 (FIG. 1). In the example of FIG. 2, ear-wearable device 102A includes one or more storage device(s) 200, a radio 202, a receiver 204, one or more processing circuit(s) 206, a set of sensors 210, a battery 212, and one or more communication channels 214. Communication channels 214 provide communication between storage device(s) 200, radio 202, receiver 204, processing circuit(s) 206, and sensors 210. Components 200, 202, 204, 206, and 210 may draw electrical power from battery 212. In other examples, components of ear-wearable device 102A may draw electrical power from another type of power source.

Sensors 210 include one or more microphone(s) 208. Additionally, in the example of FIG. 2, sensors 210 may include one or more accelerometers 218. For instance, in the example of FIG. 2, an inertial measurement unit (IMU) 220 includes accelerometers 218. IMU 220 may also include other sensors, such as gyroscopes, magnetometers, and so on. IMU 220 may use signals generated by sensors in IMU 220 for various purposes. For example, IMU 220 may use the signals generated by the sensors in IMU 220 to count the number of steps that a user of ear-wearable device 102A has taken, determine when the user has stood up, and so on.

Additionally, in the example of FIG. 2, sensors 210 also include a heart rate sensor 222, a body temperature sensor 224, and an electroencephalography (EEG) sensor 226. In other examples, ear-wearable device 102A may include more, fewer, or different components. For instance, in other examples, ear-wearable device 102A does not include one or more of the sensors shown in the example of FIG. 2. In some examples, heart rate sensor 222 comprises a visible light sensor and/or a pulse oximetry sensor.

Storage device(s) 200 may store data. Storage device(s) 200 may comprise volatile memory and may therefore not retain stored contents if powered off. Examples of volatile memories may include random access memories (RAM), dynamic random access memories (DRAM), static random access memories (SRAM), and other forms of volatile memories known in the art. Storage device(s) 200 may further be configured for long-term storage of information as non-volatile memory space and retain information after power on/off cycles. Examples of non-volatile memory configurations may include flash memories, or forms of electrically programmable memories (EPROM) or electrically erasable and programmable (EEPROM) memories.

Radio 202 may enable ear-wearable device 102A to send data to and receive data from one or more other computing devices. For example, radio 202 may enable ear-wearable device 102 to send data to and receive data from one or more of devices 106 of computing system 104 (FIG. 1), another ear-wearable device, body-worn sensor devices, implantable devices, smartwatches, or other types of devices. Radio 202 may use one or more of various types of wireless technology to communicate. For instance, radio 202 may use BLUETOOTH™, 3G, 4G, 4G LTE, ZigBee, WI-FI™, Near-Field Magnetic Induction, or another communication technology.

Receiver 204 comprises one or more speakers for generating sound. Microphone(s) 208 detect incoming sound and generate electrical signal(s) (e.g., analog or digital electrical signal(s)) representing the incoming sound. Processing circuit(s) 206 may process the signal generated by microphone 208 to enhance, amplify, or cancel-out particular channels within the incoming sound. Processing circuit(s) 206 may then cause receiver 204 to generate sound based on the processed signal. In some examples, processing circuit(s) 206 include one or more digital signal processors (DSPs).

Processing circuit(s) 206 may cause radio 202 to transmit one or more of various types of data. For example, processing circuit(s) 206 may cause radio 202 to transmit data to computing system 104. Furthermore, radio 202 may receive audio data from computing system 104 and processing circuit(s) 206 may cause receiver 204 to output sound based on the audio data.

In some examples, ear-wearable device 102 comprises a custom earmold or a standard receiver module at the end of a receiver-in-canal (RIC) cable. The additional volume in a custom earmold may allow room for components such as sensors (accelerometers, heartrate monitors, temperature sensors), a woofer-tweeter (providing richer sound for music aficionados), and an acoustic valve that provides occlusion when desired. In some examples, a six-conductor RIC cable or the like is used in ear-wearable devices with sensors, woofer-tweeters, and/or acoustic valves.

In the example of FIG. 2, storage device(s) 200 may store counter data 228 and a data log 230. Counter data 228 may include actively updated data, such as data used for determining achieved levels of one or more wellness measures. For example, ear-wearable device 102 may store data indicating an amount of time ear-wearable device 102 spent streaming media, an amount of time spent in a directional processing mode, and other values. Processing circuit(s) 206 may update counter data 228 at a more frequent rate than data log 230. Processing circuit(s) 206 may flush values from counter data 228 out to data log 230 on a periodic basis and may reset counter data 228. Additionally, processing circuit(s) 206 may cause radio 202 to send data in data log 230 to computing system 104. For instance, processing circuit(s) 206 may cause radio 202 to send data in data log 230 to computing system 104 in response to radio 202 receiving a request for the data from computing system 104. In some examples, processing circuit(s) 206 perform one or more aspects of the wellness evaluation system.

Figure 3:
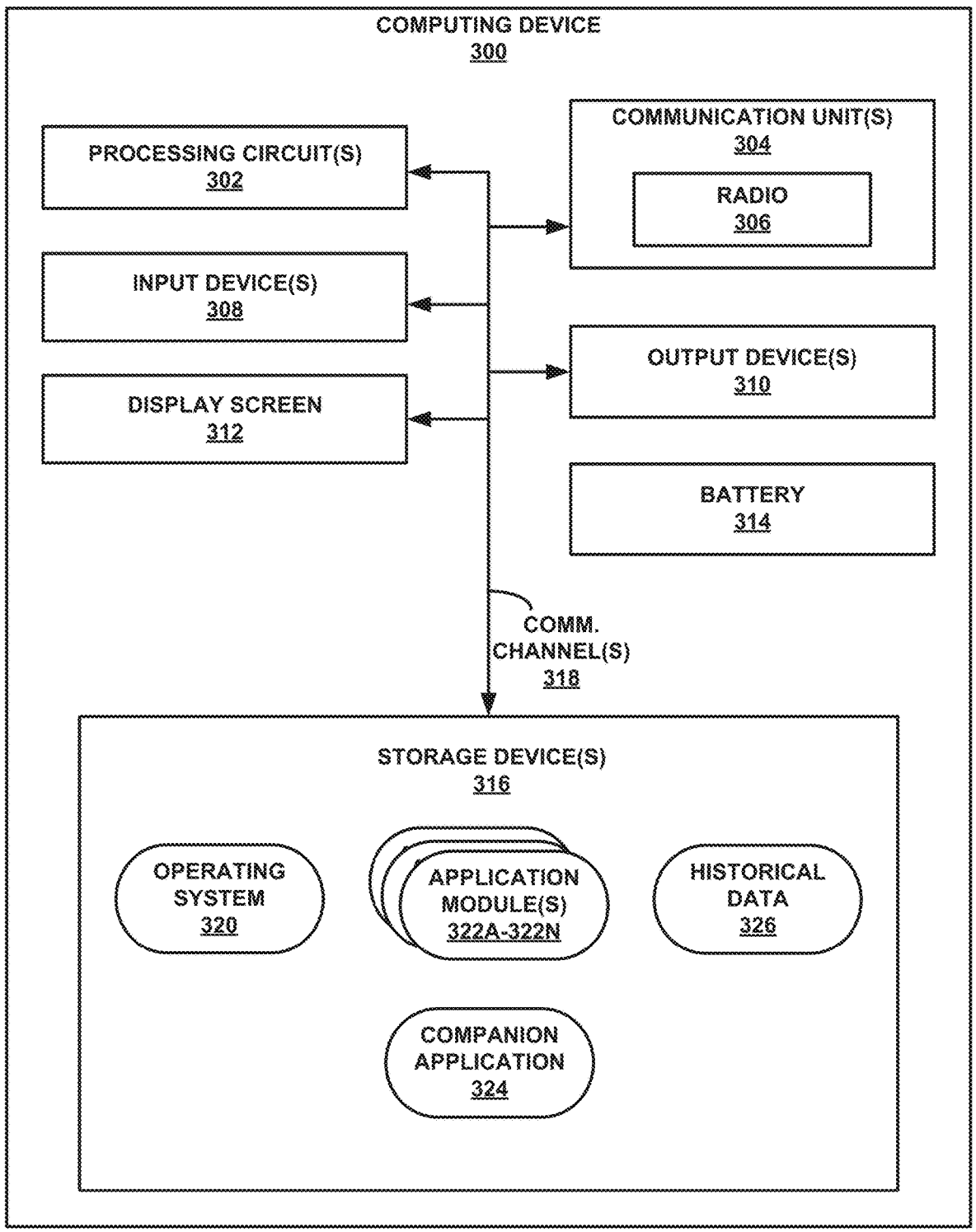
FIG. 3 is a block diagram illustrating example components of a computing device associated with a user of one or more ear-wearable devices, in accordance with one or more aspects of this disclosure.

FIG. 3 is a block diagram illustrating example components of a computing device 300 associated with a user of one or more ear-wearable device(s) 102 (FIG. 1), in accordance with one or more aspects of this disclosure. FIG. 3 illustrates only one particular example of computing device 300, and many other example configurations of computing device 300 exist. Computing device 300 may be one of devices 106 of computing system 104 (FIG. 1). For instance, computing device 300 may be a mobile device of a user of ear-wearable device(s) 102 or another type of computing device.

As shown in the example of FIG. 3, computing device 300 includes one or more processors 302, one or more communication units 304, one or more input devices 308, one or more output devices 310, a display screen 312, a battery 314, one or more storage devices 316, and one or more communication channels 318. Computing device 300 may include many other components. For example, computing device 300 may include physical buttons, microphones, speakers, communication ports, and so on. In other examples, computing device 300 may include more, fewer, or different components. For instance, in other examples, computing device 300 does not include one or more of the components shown in the example of FIG. 3, e.g., such as a display screen 312. Communication channel(s) 318 may interconnect each of components 302, 304, 308, 310, 312, and 316 for inter-component communications (physically, communicatively, and/or operatively). In some examples, communication channel(s) 318 may include a system bus, a network connection, an inter-process communication data structure, or any other method for communicating data. Battery 314 may provide electrical energy to components 302, 304, 308, 310, 312, and 316. In other examples, an alternative power source other than battery 314 may provide electrical energy to components 302, 304, 308, 310, 312 and 316.

Storage device(s) 316 may store information required for use during operation of computing device 300. In some examples, storage device(s) 316 have the primary purpose of being a short term and not a long-term computer-readable storage medium. Storage device(s) 316 may be volatile memory and may therefore not retain stored contents if powered off. Storage device(s) 316 may further be configured for long-term storage of information as non-volatile memory space and retain information after power on/off cycles. In some examples, processing circuit(s) 302 of computing device 300 may read and execute instructions stored by storage device(s) 316.

Computing device 300 may use input device(s) 308 to receive user input. Examples of user input include tactile, audio, and video user input. Input device(s) 308 may include presence-sensitive screens, touch-sensitive screens, mice, keyboards, voice responsive systems, microphones or other types of devices for detecting input from a human or machine.

Communication unit(s) 304 may enable computing device 300 to send data to and receive data from one or more other computing devices (e.g., via a communications network, such as a local area network, mesh network, or the Internet). In some examples, communication unit(s) 304 may include wireless transmitters and receivers that enable computing device 300 to communicate wirelessly with the other computing devices. For instance, in the example of FIG. 3, communication unit(s) 304 include a radio 306 that enables computing device 300 to communicate wirelessly with other computing devices, such as ear-wearable device(s) 102 (FIG. 1). Examples of communication unit(s) 304 may include network interface cards, Ethernet cards, optical transceivers, radio frequency transceivers, or other types of devices that are able to send and receive information. Other examples of such communication units may include 900 MHz, Bluetooth, 3G, and WI-FI™ radios, Universal Serial Bus (USB) interfaces, etc. Computing device 300 may use communication unit(s) 304 to communicate with one or more ear-wearable devices (e.g., ear-wearable device 102 (FIG. 1, FIG. 3)). Additionally, computing device 300 may use communication unit(s) 304 to communicate with one or more other remote devices (e.g., server device 108 (FIG. 1)).

Output device(s) 310 may generate output. Examples of output include tactile, audio, and video output. Video output may include still images or graphics, animated images, and other types of concept designed for visual perception. Output device(s) 310 may include presence-sensitive screens, sound cards, video graphics adapter cards, speakers, liquid crystal displays (LCD), virtual or augmented reality display devices, or other types of devices for generating output.

Processing circuit(s) 302 may read instructions from storage device(s) 316 and may execute instructions stored by storage device(s) 316. Execution of the instructions by processing circuit(s) 302 may configure or cause computing device 300 to provide at least some of the functionality ascribed in this disclosure to computing device 300. As shown in the example of FIG. 3, storage device(s) 316 include computer-readable instructions associated with operating system 320, application modules 322A-322N (collectively, "application modules 322"), and a companion application 324. Additionally, in the example of FIG. 3, storage device(s) 316 may store historical data 326.

Execution of instructions associated with operating system 320 may cause computing device 300 to perform various functions to manage hardware resources of computing device 300 and to provide various common services for other computer programs. Execution of instructions associated with application modules 322 may cause computing device 300 to provide one or more of various applications (e.g., "apps," operating system applications, etc.). Application modules 322 may provide particular applications, such as Short Message Service (SMS) text messaging applications, instant messaging applications, email applications, social media applications, text composition applications, and so on.

Execution of instructions associated with companion application 324 may cause computing device 300 to perform various functions. For concision, rather than indicating that execution of instructions associated with companion application 324 causes computing device 300 to perform various functions, this disclosure may simply describe companion application 324 as performing the various functions. In some examples, such as examples where computing device 300 is a mobile device or a personal computer, companion application 324 may be a native application. In some examples where computing device 300 is a server device, companion application 324 may be an instance of a web application or server application.

In examples where computing device 300 is used by the user of ear-wearable device(s) 102, such as when computing device 300 is a mobile phone of the user of ear-wearable device(s) 102, companion application 324 may configure radio 306 to wirelessly receive data from ear-wearable device(s) 102 (FIG. 1). Additionally, in some examples where computing device 300 is used by the user of ear-wearable device(s) 102, companion application 324 may implement some or all of the wellness evaluation system. For example, companion application 324 may determine levels of one or more wellness measures achieved by the user of ear-wearable device(s) 102, generate output based on one or more of the levels of or statistics relative to the level of the wellness measures, generate statistical data, and/or perform other activities.

Furthermore, in some examples where computing device 300 is used by the user of ear-wearable device(s) 102, a GUI of companion application 324 has a plurality of different sections that may or may not appear concurrently. For example, the GUI of companion application 324 may include a section for controlling the intensity of sound generated by (e.g., the volume of) ear-wearable device(s) 102, a section for controlling how ear-wearable device(s) 102 attenuates wind noise, a section for finding ear-wearable device(s) 102 if lost, and so on. Additionally, the GUI of companion application 324 may include a wellness section that displays data regarding one or more wellness measures. For instance, the GUI of companion application 324 may include a section describing a mental health wellness measure (or "brain wellness score") for the user of ear-wearable device(s) 102. In some examples, the mental health wellness measure section of companion application 324 displays a diagram similar to that shown in the example of FIG. 11. Additionally, the GUI of companion application 324 may include a body wellness score section that displays data regarding a body wellness score for the user of ear-wearable device(s) 102. In some examples, the body wellness score section of companion application 324 displays a diagram similar to the example of FIG. 12, described below. The GUI of companion application 324 may also include a wellness measure section that displays data regarding a wellness measure for the user of ear-wearable device(s) 102. In some examples, the wellness measure section of companion application 324 displays a diagram similar to the example of FIG. 13, described below.

In some examples, companion application 324 may request data for calculating one or more of an achieved level of a wellness measure or other statistical data from ear-wearable device(s) 102 each time computing device 300 receives an indication of user input to navigate to the cognitive benefit section or body wellness score section of companion application 324. In this way, a user of ear-wearable device(s) 102 may get real-time confirmation that companion application 324 is communicating with ear-wearable device(s) 102, and that the data displayed are current, and may ensure that the wireless transfer of the data-log data does not interrupt or interfere with other processes in companion application 324, or on computing device 300 device. Furthermore, requesting data from ear-wearable device(s) 102 only when computing device 300 receives an indication of user input to navigate to the brain wellness score section, the body wellness score section, or the wellness measure section of companion application 324 may reduce demands on a battery (e.g., battery 212 of FIG. 2) of ear-wearable device(s) 102 (FIG. 1), relative to computing device 300 requesting the data from ear-wearable device(s) 102 on a periodic basis.

In some examples, however, it may be desirable for companion application 324 to request data without intentional user input, either periodically or based upon one or more of one or more sensor signals, values of one or more wellness measures, one or more risk predictions, or other data crossing a predetermined or dynamically-adapted threshold. For example, companion application 324 may request data for calculating one or more of an achieved level of a wellness measure or statistical data from ear-wearable device(s) 102 at various different frequencies dependent upon, e.g., the outputs of a risk prediction model or engine, such as the techniques described in U.S. Provisional Patent Application No. 62/785,295, entitled PREDICTIVE FALL EVENT MANAGEMENT SYSTEM AND METHOD OF USING SAME, filed on Dec. 27, 2018. As an illustration, the frequency of wellness data requests by companion application 324 may temporarily increase, for example, based upon detected or predicted events, such as balance events (i.e., events during which a user checks the user's balance). The number, frequency, severity, or other aspects of such balance events may be examples of statistical data generated by the wellness evaluation system based on data generated by the sensors.

Companion application 324 may store one or more of various types of data as historical data 326. Historical data 326 may comprise a database for storing historic data related to cognitive benefit. For example, companion application 324 may store, in historical data 326, brain wellness scores, body wellness scores, sub-component values, data from ear-wearable device(s) 102, and/or other data. Companion application 324 may retrieve data from historical data 326 to generate a GUI for display of past levels of one or more wellness measures of the user of ear-wearable device(s) 102. In at least one example, the wellness level data and statistic data may be stored and shared as an input into to a risk prediction model and optionally associated with, e.g., a detected or predicted balance event.

Figure 4:
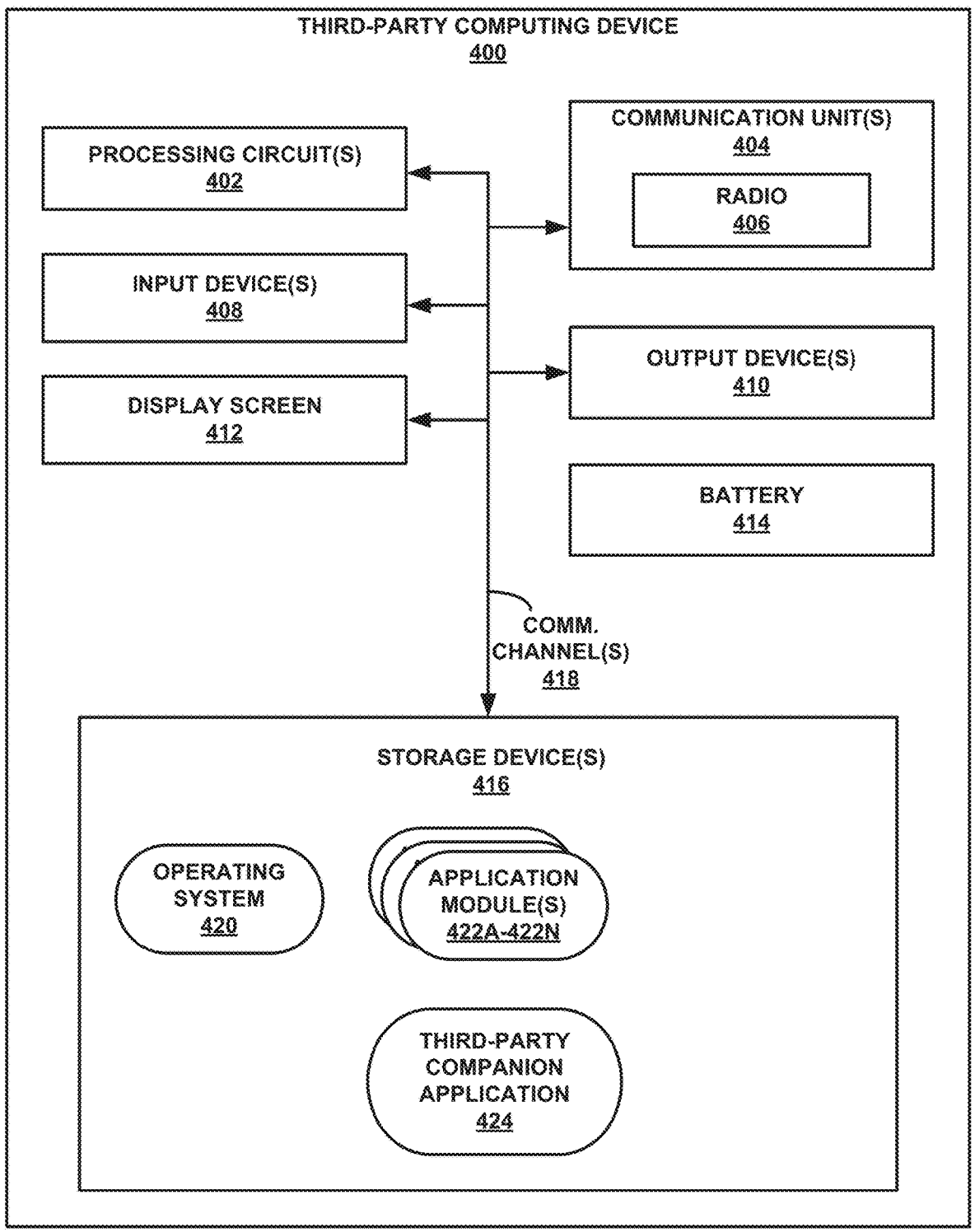
FIG. 4 is a block diagram illustrating example components of a third-party computing device, in accordance with one or more aspects of this disclosure.

FIG. 4 is a block diagram illustrating example components of a third-party computing device 400, in accordance with one or more aspects of this disclosure. Third-party computing device 400 may be one of devices 106 of computing system 104 (FIG. 1). Third-party computing device 400 may be used by a third-party, such as a relative of the user of ear-wearable device(s) 102, a caregiver of the user of ear-wearable device(s) 102, a healthcare professional (e.g., an audiologist) of the user of ear-wearable device(s) 102, or another type of person. In some examples, third-party computing device 400 is a smartphone, a tablet computer, a personal computer, or an artificial intelligence assistant associated with the third-party. In this disclosure, a "third-party" may refer to a person other than the user of ear-wearable device(s).

In the example of FIG. 4, third-party computing device 400 includes one or more processors, i.e., processing circuit(s), 402, communication unit(s) 404 (which may include a radio 406), input device(s) 408, output device(s) 410, a display screen 412, a battery 414, storage device(s) 416, and communication channel(s) 418. These components of third-party computing device 400 may be implemented in the same manner as similar components of computing device 300. In the example of FIG. 4, storage device(s) 416 may include instructions associated with an operating system 420 and application module(s) 422A-422N (collectively, "application module(s) 422"). Operating system 420 and application module(s) 422 may perform similar functions and may be implemented in a similar way as operating system 320 and application module(s) 322 of FIG. 3.

In the example of FIG. 4, storage device(s) 416 may include instructions associated with a third-party companion application 424. Third-party companion application 424 may generate a GUI for display. In some examples, the GUI generated by third-party companion application 424 may include features similar to the features of the GUI described elsewhere in this disclosure. For instance, the GUI of third-party companion application 424 may include a wellness section that displays data regarding one or more wellness measures. In some examples, the GUI of third-party companion application 424 may include statistical data and/or information generated based on the statistical data. Such statistical data may relate to the wellness of the user of ear-wearable device(s) 102. In some examples, the GUI generated by third-party companion application 424 may include the GUIs presented in the examples of FIG. 11, FIG. 12, and FIG. 13.

Furthermore, in some examples, third-party companion application 424 may generate notifications that notify the third-party with respect to one or more aspects of the wellness of the user of ear-wearable device(s) 102. Third-party companion application 424 may generate such notifications based on outputs from a wellness evaluation system. Third-party companion application 424 may generate the notifications in various ways. For example, third-party companion application 424 may cause third-party computing device 400 to display a notification message, output a sound, display text or graphics in a GUI, vibrate, or otherwise provide information that notifies the third-party with respect to the one or more aspects of the wellness of the user of ear-wearable device(s) 102. In some examples, third-party companion application 424 may implement all or a portion of the wellness evaluation system.

Figure 5:
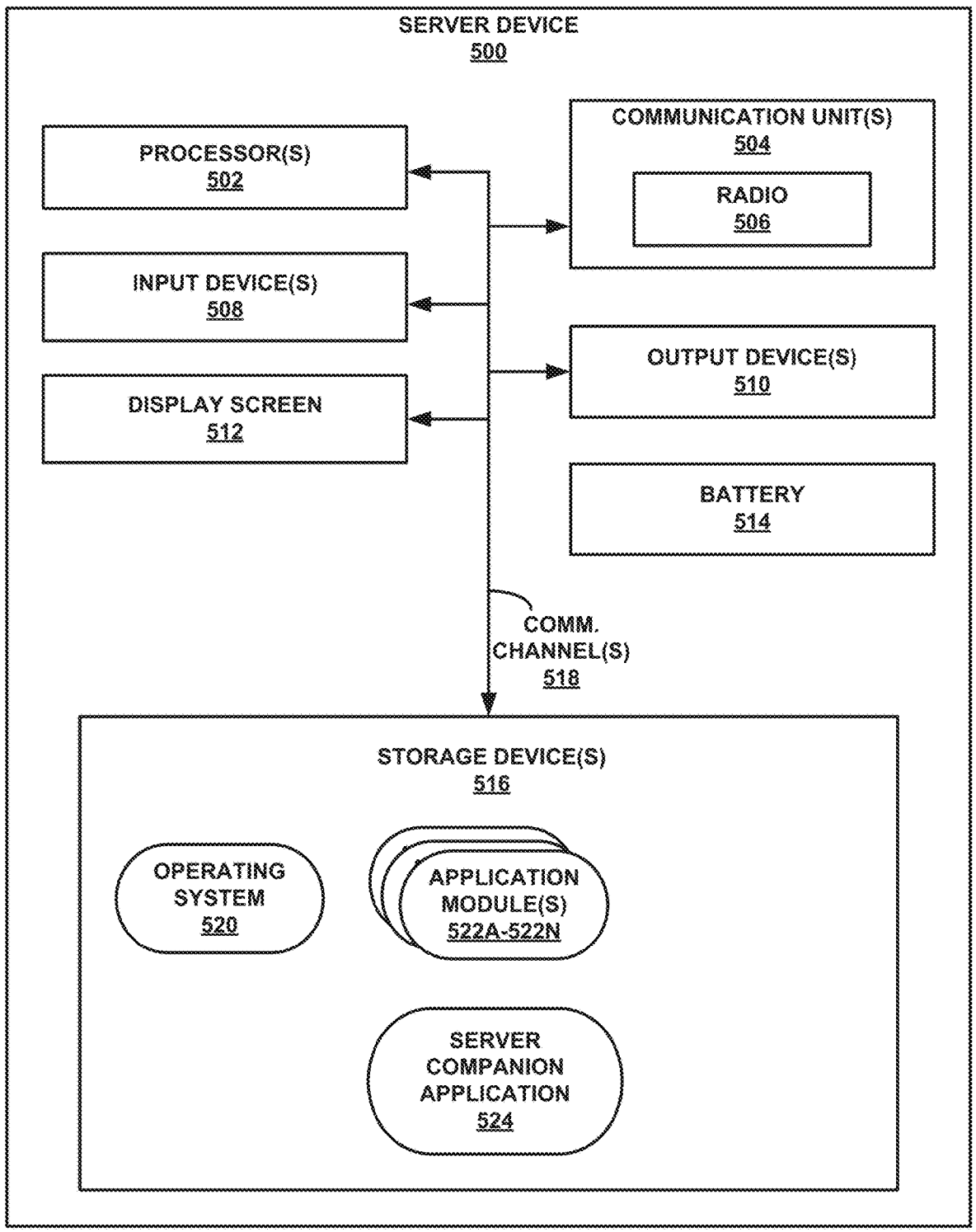
FIG. 5 is a block diagram illustrating example components of a server computing device, in accordance with one or more aspects of this disclosure.

FIG. 5 is a block diagram illustrating example components of a server computing device 500, in accordance with one or more aspects of this disclosure.

Server computing device 500 may be one of devices 106 of computing system 104 (FIG. 1). Server computing device 500 may be remote from the user of ear-wearable device(s) 102 and may be remote from third-parties, such as relatives of the user of ear-wearable device(s) 102, caregivers of the user of ear-wearable device(s) 102, healthcare professionals of the user of ear-wearable device(s) 102, and so on.

In the example of FIG. 5, server computing device 500 includes processing circuit(s) 502, communication unit(s) 504 (which may include a radio 506), input device(s) 508, output device(s) 510, a display screen 512, a battery 514, storage device(s) 516, and communication channel(s) 518. These components of server computing device 500 may be implemented in the same manner as similar components of computing device 300 and 400. In the example of FIG. 5, storage device(s) 516 may include instructions associated with an operating system 520 and application module(s) 522A-522N (collectively, "application module(s) 522"). Operating system 520 and application module(s) 522 may perform similar functions and may be implemented in a similar way as operating system 320 and application module(s) 322 of FIG. 3 and operating system 420 and application module(s) 422 of FIG. 4.

In the example of FIG. 5, storage device(s) 516 may include instructions associated with a server companion application 524. Server companion application 524 may generate a GUI for display. For instance, server companion application 524 may generate one or more webpages that include the GUI and may send data representing the webpages to one or more devices, such as computing device 300 or third-party computing device 400. In some examples, the GUI generated by server companion application 524 may include features similar to the features of the GUI described above. For instance, the GUI generated by server companion application 524 may include a wellness section that displays data regarding one or more wellness measures. In some examples, the GUI generated by server companion application 524 may include the GUIs presented in the examples of FIG. 11, FIG. 12, and FIG. 13.

Furthermore, in some examples, server companion application 524 may generate notifications that notify the user of ear-wearable device(s) 102 and/or the third-party with respect to one or more aspects of the wellness of the user of ear-wearable device(s) 102. Server companion application 524 may generate such notifications based on outputs from a wellness evaluation system. Server companion application 524 may generate the notifications in various ways. For example, server companion application 524 may cause a computing device (e.g., computing device 300, third-party computing device 400, etc.) to display notification messages, output sounds, display text or graphics in a GUI, or otherwise provide information that notifies the user of ear-wearable device(s) 102 or a third-party with respect to the one or more aspects of the wellness of the user of ear-wearable device(s) 102. In some examples, alerts to one or more of the user and a third-party may be generated in the cloud and then communicated using any suitable technique or techniques, e.g., email, SMS text message, voice message and the like. In some examples, server companion application 524 may implement all or a portion of the wellness evaluation system.

Figure 6:
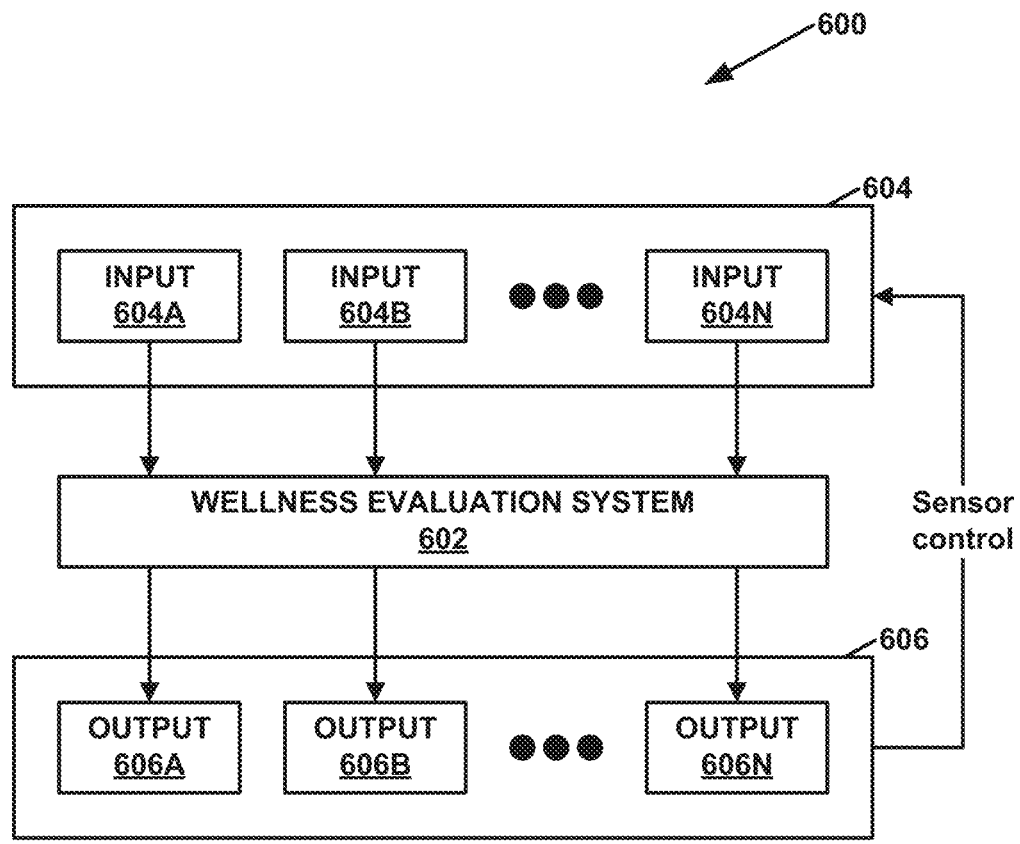
FIG. 6 is a block diagram illustrating an example system that includes a wellness evaluation system implemented in accordance with the techniques of this disclosure.

FIG. 6 is a block diagram illustrating an example system 600 that includes a wellness evaluation system 602 implemented in accordance with the techniques of this disclosure. Wellness evaluation system 602 may be implemented in various devices. For example, some or all of wellness evaluation system 602 may be implemented in one or more of ear-wearable device(s) 102. In some examples, some or all of wellness evaluation system 602 may be implemented in computing system 104. For example, some or all of wellness evaluation system 602 may be implemented by server companion application 524 of server computing device 500 (FIG. 5). In some examples, some or all of wellness evaluation system 602 may be implemented by third-party companion application 424 of third-party computing device 400 (FIG. 4).

In the example of FIG. 6, wellness evaluation system 602 receives a set of inputs 604. Inputs 604 include input 604A through input 604N. Inputs 604 may include data generated by one or more of sensors 210 of ear-wearable device(s) 102. In some examples, inputs 604 include data generated by one or more other devices, such as a mobile device associated with the user of ear-wearable device(s) 102. For instance, in some examples, inputs 604 may include data generated by one or more sensors of the mobile device. In some examples where wellness evaluation system 602 is implemented in ear-wearable device(s) 102, inputs 604 may include data received from the mobile device. In some examples where wellness evaluation system 602 is implemented in mobile device(s) 102 (FIG. 1), inputs 604 may include data received from ear-wearable device(s) 102.

As shown in the example of FIG. 6, wellness evaluation system 602 may generate a set of one or more outputs 606. In the example of FIG. 6, outputs 606 include output 606A through output 606N. Outputs 606 may include notifications, text or graphics in a GUI, verbal feedback to be presented by receivers of ear-wearable device(s) 102, text messages, automated phone calls, and so on.

In some examples, one or more of outputs 606 provide social engagement tips. A social engagement tip may include advice regarding how to increase the user's level of social engagement. For example, if restaurant activity has been identified as being problematic for the user, a social engagement tip may suggest that the user visit restaurants at non-peak times. In another example, if restaurant activity has been identified as being problematic for the user, a social engagement tip may suggest that the user visit specific restaurants where users with similar hearing difficulties tend to succeed. In this example, wellness evaluation system 602 may use data from other users to generate the restaurant suggestions. In some other examples, a social engagement tip may include advice regarding how to improve the quality of a social engagement with e.g., a particular individual. In this example, wellness evaluation system 602 may use one or more of historical data or data from other users to generate and provide the user with tips on how to avoid conflict with e.g., a specific communication partner. Similarly, wellness evaluation system 602 may alert third parties when the user is in positive mood or an otherwise receptive state of mind.

Wellness evaluation system 602 may provide social engagement tips to users in various ways. For example, wellness evaluation system 602 may send a message to a computing device (e.g., a smartphone or tablet) associated with the user of ear-wearable device(s) 102. In some examples, the message is a text message, such as a SMS text message, social media message, or an instant message (e.g., a MESSAGES™ message on a Messages application from Apple Inc. of Cupertino, California, Facebook MESSENGER™ message, etc.). In some examples, wellness evaluation system 602 provides social engagement tips in an application, such as companion application 324. In some examples, wellness evaluation system 602 provides social engagement tips as voice messages played back to the user via receivers (e.g., receiver 204) of ear-wearable device(s) 102.

Wellness evaluation system 602 may direct social engagement tips to one or more third-parties. For instance, wellness evaluation system 602 may direct social engagement tips to caregivers, such as nurses or family members, in order to help the caregivers set the user of ear-wearable device(s) 102 up for success. This may be especially helpful in the case of users who are unfamiliar with, unaccustomed to using, or unable to use electronic devices, such as mobile phones. For instance, many elderly people with hearing loss are also unaccustomed to using or lack efficacy when using electronic devices. Moreover, caregivers may be better equipped to implement the social engagement tips than ear-wearable device users who have memory loss, physical limitations, or who have experienced some cognitive decline. In some examples where wellness evaluation system 602 directs social engagement tips to a third-party, third-party companion application 424 (FIG. 4) may present the social engagement tips to the third-party. In other examples, wellness evaluation system 602 may alert third parties when the user could benefit from additional social interaction, and the wellness evaluation system 602 may e.g., prompt one or more of a third party or an artificial intelligence companion to initiate a social interaction with the user. An artificial intelligence companion may be an artificial intelligence system designed to interact with the user in a manner similar to a real human (e.g., using interactive voice responses). For instance, wellness evaluation system 602 may provide, based on a determination that the user has not satisfied a target level of a wellness measure, an alert that prompts a third party or artificial intelligence companion to initiate a social interaction with the user.

In some examples, gamification of outputs 606 may be used to encourage the user of ear-wearable device(s) to engage in activities associated with better health outcomes. For example, outputs 606 generated by wellness evaluation system 602 may include daily targets for particular activities, such as time spent in conversation, number of individual conversational partners, and so on. In some examples, companion application 324 (FIG. 3) may provide a GUI that presents graphics (e.g., charts, tables, diagrams, etc.) that indicate the user's achieved levels of the wellness measures, e.g., as compared to past achievement and/or as compared to other users.

Social groups may be established in some examples where gamification of one or more of outputs 606 is used. That is, wellness evaluation system 602 may store data indicating that the user of ear-wearable device(s) 102 is a member of one or more of the social groups. Each of the social groups is a group of two or more ear-wearable device users. In such examples, wellness evaluation system 602 may be configured to reward members in a social group for social engagement with other members of the social group and/or with others outside the social group. Wellness evaluation system 602 may provide rankings of the members of a social group to the members of the social group, where the rankings are based on the users' associated levels in one or more wellness measures, such as social engagement measures, physical activity levels, and so on. In some examples, such rankings may help users achieve their target levels of one or more wellness measures by encouraging friendly competition. In some examples, such rankings may help third-parties better understand how the user of ear-wearable device(s) 102 compares with other comparable individuals. In some examples, the score scaling presented by the GUIs described above may be adapted by evaluation system 602 based upon the aggregate of one or more of inputs 604 over time, data inputs of other members of at least one of the user's social groups, or the member rankings of at least one social group.

As mentioned elsewhere in this disclosure, outputs 606 of wellness evaluation system 602 may provide information about the user of ear-wearable device(s) 102 to one or more third-parties. In some examples, the provided information may inform the third-parties of signs of cognitive and/or physical decline. In some examples, the provided information may identify opportunities for intervention. In some examples, the provided information may identify risks of depression, social isolation, activity limitation, falling, loneliness, and/or other factors associated with the mental, emotional, or physical health of the user of ear-wearable device(s) 102. In some other examples, the provided information may identify risks of one or more of a speech language pathology, delayed language development, attention deficit, learning disability, patterns of bullying or abuse, and/or other factors associated with the user, e.g., childhood, adolescent, or educational development of the user of ear-wearable device(s) 102. In some examples, the provided information may indicate whether ear-wearable device(s) 102 need to be adjusted to better serve the user. In some examples, the provided information may recommend communication therapies or additional interventions. In some examples, the provided information may be directed at one or more of emergency responders, medical professionals, or educators.

In the example of FIG. 6, one or more of outputs 606 generated by wellness evaluation system 602 may include sensor controls that selectively activate or deactivate sensors that generate one or more of inputs 604. For example, one or more of outputs 606 may include commands to activate or deactivate a satellite-based radio-navigation system sensor, EEG sensor 226 (FIG. 2), electrocardiogram (ECG) sensors, electrodermal sensors, IMU 220 (FIG. 2), heart rate sensor 222 (FIG. 2), and/or other sensors. In one example, one or more of outputs 606 may include a command to activate a gyroscope of an IMU (e.g., IMU 220 of FIG. 2) in response to one or more accelerometers of the IMU indicating that the user may be engaging in an activity of interest. Selectively activating sensors may help conserve battery power of one or more of ear-wearable device(s) 102 and/or devices 106 (FIG. 1).

In addition to helping to conserve battery life, selectively activating and deactivating sensors may help to preserve the privacy of the user of ear-wearable device(s) 102. For instance, because certain sensors may be only active when needed, the sensors are not producing data that can potentially be subject to inappropriate access. For example, a GPS sensor of ear-wearable device(s) may be activated only under particular conditions.

Figure 7:
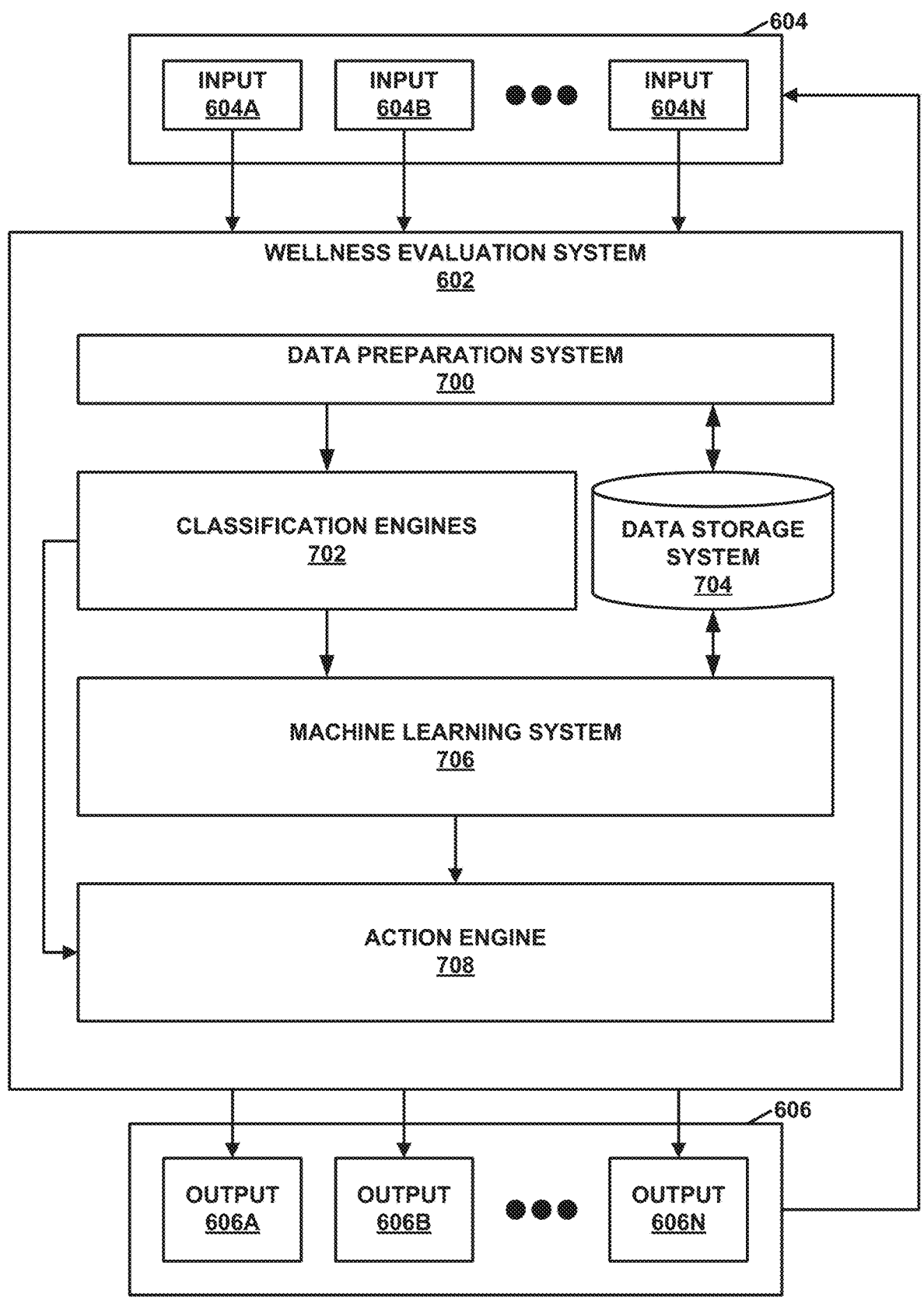
FIG. 7 is a block diagram illustrating example details of the wellness evaluation system that may be implemented in accordance with the techniques of this disclosure.

FIG. 7 is a block diagram illustrating example details of wellness evaluation system 602 that may be implemented in accordance with the techniques of this disclosure. In the example of FIG. 7, wellness evaluation system 602 includes a data preparation system 700, a set of classification engines 702, data storage system 704, a machine learning system 706, and an action engine 708.

Data preparation system 700 prepares data for use by classification engines 702. For instance, data preparation system 700 may prepare inputs 604 for use by classification engines 702. Data preparation system 700 may perform a variety of processes to prepare inputs 604 for use by classification engines 702. Data preparation system 700 can prepare inputs 604 and other data using any suitable technique or techniques. For instance, in one or more examples, data preparation system 700 may e.g., filter, time stamp, assign metadata memory locations, generate statistical data relative to, and combinations thereof, to data of inputs 604. As used herein, the term "data" can include a single datum or a plurality of data values or statistics values. The term "statistical data" can include data calculated according to any appropriate mathematical calculation or metric for data interpretation, e.g., probability, confidence interval, distribution, range, or the like. In some examples, data storage system 704 may store data generated by data preparation system 700. Data storage system 704 may be part of the memories of data storage systems of devices that implement wellness evaluation system 602. In some examples, data storage system 704 may also store data generated by sensors.

Each of classification engines 702 may receive input data and may generate classification data. The input data received by classification engines 702 may include data generated by data preparation system 700. Machine learning system 706 may include one or more machine learning modules. The machine learning modules of machine learning system 706 may use input data that includes the classification data generated by classification engines 702 and/or other data to determine achieved levels of one or more wellness measures and/or statistical data. The statistical data may be relative to one or more wellness measures or inputs 604. In some examples, machine learning system 706 may obtain input data from data storage system 704 and/or store data, such as data indicating achieved levels of wellness measures or statistical data, to data storage system 704. Action engine 708 may generate outputs 606 based on one or more of the achieved levels of the wellness measures and/or the statistical data. As mentioned above, machine learning system 706 may include one or more machine learning modules. One or more of the machine learning modules may be implemented using one or more artificial neural network (ANNs) or another type of machine learning technique. For example, a machine learning module of machine learning system 706 may use information regarding locations visited by the user of ear-wearable device(s) 102, acoustic environments experienced by the user, conversational companions of the user, activities performed by the user, intentional listening performed by the user, emotions experienced by the user, and/or other information as input. In such examples, the machine learning module may be trained to determine achieved levels of one or more wellness measures. In some examples, one or more machine learning module of machine learning system 706 may be fully or partly trained prior to use with the user of ear-wearable device(s) 102. In some examples, training of one or more of the machine learning module of machine learning system 706 may continue after the commencement of use of wellness evaluation system 602 with respect to the user of ear-wearable device(s) 102.

In some examples where a machine learning module of machine learning system 706 is implemented using an ANN, an output layer of the ANN may include a different artificial neuron for each of the wellness measures. In other words, different artificial neurons in the output layer of the ANN may correspond to different wellness measures. In such examples, the artificial neurons in the output layer of the ANN may generate output values that indicate achieved levels of the corresponding wellness measures. The ANN may be trained to determine an achieved level of a wellness measure using set of labeled input data.

In other examples, machine learning system 706 may include different machine learning modules corresponding to different wellness measures. For example, machine learning system 706 may include a first machine learning module that determines an achieved level of interaction with multiple people. In this example, machine learning system 706 may include a second machine learning module that determines an achieved level of diversity of locations. In some such examples where machine learning system 706 includes different ANNs for different wellness measures, output layers of the ANNs may each include a single artificial neuron that outputs the achieved level of the corresponding wellness measure. In some examples, a first machine learning module of machine learning system 706 may correspond to two or more wellness measures and a second machine learning module of machine learning system 706 may correspond to one or more other wellness measures.

Similarly, machine learning system 706 may include different machine learning modules corresponding to different types of statistical data. For example, machine learning system 706 may include a machine learning module that determines a probability of the user of ear-wearable device(s) 102 experiencing a fall. In this example, machine learning system 706 may include one or more machine learning modules that determine probabilities of the user of ear-wearable device(s) 102 experiencing depression, committing self-harm, acquiring dementia, detecting various pathologies, being in abusive relationships, and so on. In some examples, a machine learning module corresponding to a type of statistical data may take, as input, achieved levels of one or more wellness measures as determined by other machine learning modules of machine learning system 706.

In some examples, machine learning system 706 applies reinforcement machine learning techniques to select the best possible output behavior strategy for one or more of the user or a context regarding the user. Reinforcement learning models can consider one or more of a determined achieved level of one or more wellness measures, outputs 606, inputs 604, outputs of classification engines 702, user rankings, risk models, and the like. In one or more examples, the reinforcement machine learning model(s) can further consider the statistical data associated with historical data (e.g., data stored in data storage system 704) to optimize one or more of the actions determined by action engine 708. In one or more examples, determining an action includes applying, by action engine 708, input data to a statistical model or module. Such a statistical model or module can be developed from evaluating the effectiveness of outputs 606 from wellness evaluation system 602 over time. In one or more examples, machine learning system 706 includes one or more modules, e.g., a mental state module, a social engagement state module, an emotional state module, a physical state module, etc. that may influence action engine 708.

In some examples, a wellness measure may be based on one or more other wellness measures. For example, machine learning system 706 may determine achieved levels of a use score, an engagement score, and an active listening score. In this example, the use score may be based on how much time the user of ear-wearable device(s) 102 uses the ear-wearable device(s) 102 during a scoring period. In another example, the "engagement" sub-component may be based at least in part on how much time the user of ear-wearable device(s) 102 engages in conversation during a scoring period and how much time the user of ear-wearable device(s) 102 uses ear-wearable device(s) 102 to stream audio media during the scoring period. The "active listening" sub-component may be determined based on exposure of the user of ear-wearable device(s) 102 to a plurality of different environments, such as acoustic environments, during a current scoring period. In this example, a "brain wellness score," which may correspond to an overall level of mental wellness of the user of ear-wearable device(s), may be based on one or more of the use score, the engagement score, the active listening score, and/or other types of scores or data. For instance, the "brain wellness score" may be the weighted sum of e.g., the use score, the engagement score, the active listening score and/or other types of scores or data.

In another example of a wellness measure that is based on one or more other wellness measures, a "body wellness score" may be based on a "steps" component, an "activity" component, and a "move" component. In this example, the "steps" component may be based on a number of steps taken by the user of ear-wearable device(s) 102 during a scoring period. The "activity" component may be a measure of vigorous activity in which the user of ear-wearable device(s) 102 has engaged during the current scoring period. The "move" component may be based on a number time of intervals during the current scoring period in which the user of ear-wearable device(s) 102 moves for a given amount of time. In some examples, the "body wellness score" may be based on a sum of the "steps" component, "activity" component, and "move" component. Any suitable arrangement of components may be used to calculate "body wellness score." In some examples, a "body wellness score" may also be based on an optional "exercise" component, in addition to a "steps" component, an "activity" component, and a "move" component. In some examples, an "exercise" component may only be calculated or displayed for a subset of users of wellness evaluation system 602.

As mentioned above, action engine 708 may generate outputs 606 based on the achieved levels of the one or more wellness measures determined by machine learning system 706. In other words, action engine 708 may determine which actions to take based on the achieved levels of the wellness measures. For instance, in some examples, one of outputs 606 is a webpage that contains information associated with the levels of one or more wellness measures achieved by the user of ear-wearable device(s) 102. Accordingly, in such examples, action engine 708 may include a web server that generates such webpages and provides the webpages to computing devices (e.g., computing device 300 (FIG. 3), third-party computing device 400 (FIG. 4), etc.). In some examples, wellness evaluation system 602 implements an application programming interface (API) that enables client applications (e.g., companion application 324 (FIG. 3), third-party companion application 424 (FIG. 4), or other applications) to obtain data that the client applications may use to present information to the user or third-parties.

In some examples, outputs 606 may include text messages. Accordingly, in such examples, action engine 708 may include a server for automatically sending text messages. In some examples, outputs 606 may include voice messages. Accordingly, in such examples, action engine 708 may include a server for sending the voice messages or information for generating or playing back the voice messages.

Outputs 606 generated by action engine 708 may include messages to activate or deactivate one or more sensors (e.g., sensors 210 (FIG. 2)). Accordingly, action engine 708 may send messages to one or more ear-wearable device(s) 102 and/or other devices indicating that the ear-wearable device(s) or other device are to activate or deactivate particular sensors. In some examples, action engine 708 may send messages to ear-wearable device(s) 102 and/or other devices to start or stop duty cycling between sensors in a set (e.g., pair) of sensors.

Furthermore, in some examples, outputs 606 generated by action engine 708 may include messages to activate or deactivate one or more of classification engines 702. For example, a first one of classification engines 702 may classify the type of environment that the user is currently in and a second one of classification engines 702 may classify the types of people present in the environment that the user is currently in. In this example, outputs 606 may include a message to activate the second classification engine if the first classification engine determines that the environment that the user is currently in is an environment that includes human-directed communication signals, such as the sounds of human voices. Human-directed communication signals may also include one or more of natural human communication, recorded human communication, or synthesized human communication. In some examples, human-directed communication signals may also include e.g., utterances from pre-linguistic children or animals that have vocal efforts that carry meaning to some humans.

In some other examples, human-directed communication signals may also include manual forms of communication such as sign-language, house signs (e.g., informal forms of sign language), gestures, and the like. In examples where human-directed communication signals include one or more of non-verbal and manual forms of communication, operatively connected cameras may capture video of the user's environment. In some examples, non-verbal communication may include facial expression, eye contact, joint attention, or body language. Joint attention is the shared focus of two or more individuals on the same object. In some examples, sensors or sensor elements on one or more of a signer's hands or arms may be used to detect manual forms of communication. Furthermore, in some examples, the user may be considered to be in an environment that includes human-directed communication signals when the user is interacting with a communication device (e.g., a smartphone, tablet, personal computer, etc.) to receive text, audio, or video messages. In some other examples, the user may be considered to be in an environment that includes human-directed communication signals when the user is interacting with an augmentative and alternative communication (AAC) device such as: basic communicators, multiple message communicators, picture communicators, progressive communicators, adaptable recorded speech communication devices, type and talk devices, sequential message communicators, scanning communicators, communicators for the visually impaired, and the like.

In some examples, a set of cameras (e.g., cameras worn by the user of ear-wearable device(s) 102, fixed-position cameras, etc.) may generate video signals that can be used for non-verbal communication. In examples where video signals are used to detect eye contact and joint attention, the set of cameras may include one or more cameras positioned to detect the direction of eye gaze of the user of ear-wearable device(s) 102 and one or more cameras positioned to detect the direction of eye gaze of one or more other people. In one example, based on video signals from these cameras, wellness evaluation system 602 (e.g., data preparation system 700) may determine 3-dimensional gaze vectors of the user and one or more other people. In other examples, wellness evaluation system 602 may estimate a gaze vector based on signals from other types of sensors (e.g., IMUs such as IMU 220) configured to detect head pose of the user of ear-wearable device(s) 102 and/or other people. Various techniques for determining gaze vectors are known in the art. See e.g., Manabe et al., "Using Earphones to Perform Gaze Detection for Wearable Interfaces," NTT DOCOMO Technical Journal Vol. 12 No. 3 (2010).

In this example, wellness evaluation system 602 (e.g., classification engine 702) may determine that there is eye contact between the user of ear-wearable device(s) 102 and another person if the gaze vector of the user points to an origin points of the other person's gaze vector, and vice versa. In this example, classification engines 702 may output classification data indicating the occurrence of eye contact. Furthermore, in this example, wellness evaluation system 602 (e.g., classification engines 702 of wellness evaluation system 602) may determine joint attention based on the user's gaze vector and another person's gaze vector intersecting at an object in the user's environment. Wellness evaluation system 602 may determine whether triadic joint attention has occurred if the user's gaze vector shifts back to the other person's face after the user's gaze vector and the other person's gaze vector intersect at the object, potentially followed by shifting the user's gaze vector back to the object. Triadic joint attention is the highest level of joint attention and occurs when each of the individuals (e.g., the user of ear-wearable device(s) 102 and the other person) understand that the other individual is looking at the same object and realize that there is an element of shared attention.

Data from the eye movement sensor and the positional sensors can be analyzed to determine the direction of simultaneous head and eye movements (i.e., determine gaze). The processed signals can be analyzed to determine normal data traits at using any suitable technique or techniques. Such normal data traits can indicate smooth eye and head movements. Further, abnormal data traits such as nystagmus can be identified using any suitable technique or techniques.

Such abnormal data traits can include abnormal signatures of head and eye movements. Further, nystagmus can be observed in eye movement sensor data. Nystagmus can be identifiable when the user's eyes exhibit both a fast movement phase followed by a slow movement phase in the opposite direction of the fast phase. Nystagmus can appear as a pattern of repeated fast phase and slow phase eye movements. Further, the abnormal signatures may include abnormal head movement, which may include rapid movement, detection of free fall or impact, etc.

The direction of beating (fast phase) of the user's eye movements can be determined using any suitable technique or techniques. The eyes can be determined to be beating in one direction (e.g., right or left), in alternating directions (i.e., right and left), or torsionally (i.e., in a twisting motion to right or left and either up or down).

The data regarding the direction of beating of the eyes can be correlated to positional sensor data at using any suitable technique or techniques. For example, eye motion data can be analyzed within the context of the measured head movement (i.e., positional data).

Eye movement and positional data may indicate a typical vestibulo-ocular reflex (VOR). In other words, eye movement and positional data may indicate that the user's eyes move in opposite angular directions of the head when the user is maintaining a steady gaze. In one or more examples, the eye movement and positional data indicate typical optokinetic responses, i.e., nystagmus is present when the user experiences a rapid velocity (e.g., when looking through the window of a car and watching the trees pass by).

Eye movement and positional data may indicate that the user is experiencing a vestibular disturbance. Such disturbance can be determined when nystagmus is present when the head is not moving, when the eyes are moving in alternating directions, when the onset of nystagmus follows seconds after a movement of the head (usually, but not always, when the head is tilted upward), or when such nystagmus persists for greater than several seconds.

One or more of ear-wearable device(s) 102 include magnetic sensors, telecoils, or other sensors that are sensitive to magnetic fields. In accordance with one or more techniques of this disclosure, wellness evaluation system 602 may use the sensors which are sensitive to magnetic fields (i.e., magnetic field sensors) that are present in the user's environment for the detection and classification of the user's activities and environment. Numerous identified activities and environments that have distinct electromagnetic signature patterns. Magnetic field sensors are common hearing device hardware. In one example, a magnetic sensor may sense the magnetic field emitted by a car engine. In another example, one or more magnetic sensors may track usage of electrical appliances. For example, there are numerous electrical appliances that self-sustaining adults typically use during daily activities. Monitoring the use of an individual's day-to-day use of electrical appliances has been found to be reflective of well-being and this individualized insight has also been reported as being useful in assisting older adults to age in place.

In some examples, classification engines 702 may use signals from the magnetic field sensors to classify types and durations of the sources of magnetic fields in the user's environment. Machine learning system 706 of wellness evaluation system 602 may use the resulting classification data generated by classification engines 702 to determine achieved levels of one or more wellness measurements, to determine statistical data, or generate other types of information.

In some examples, machine learning system 706 may use machine learning techniques to associate one or more of an observed behavior, a wellness measure level, a wellness measure statistic, an output, a social engagement tip, a gamification technique, and outcomes such that outputs and gamification techniques may be optimized over time on one or more of the individual level or group level. Outcomes may include, for example, wellness measure levels and statistics relative to wellness measures observed over time. Outcome measures may also include other physiological and behavioral observations which may be measured or reported by one or more sensors, monitoring devices, and health record systems operatively connected the computing device. In some examples, data may be entered manually by one or more of the user or a third-party. For example, stress levels, blood pressure, occurrence of balance events, and the like may be measured by input devices.

In some examples, action engine 708 may generate one or more outputs 606 based on data generated by classification engines 702 without the involvement of machine learning system 706. For instance, one or more of outputs 606 may be generated by action engine 708 without reference to an achieved level of a wellness measure. For example, if one of classification engines 702 determines that the user of ear-wearable device(s) 102 is in an environment that includes human-directed communication signals, outputs 606 may include a message to activate one or more additional sensors.

In some examples, data preparation system 700, classification engines 702, machine learning system 706, and action engine 708 may be implemented in a modular fashion. For instance, code modules that perform data preparation routines may be plugged in and removed from data preparation system 700 without changing an architecture of wellness evaluation system 602. Similarly, code modules for different classification engines 702 may be plugged in and removed from wellness evaluation system 602 without changing the architecture of wellness evaluation system 602. Furthermore, in some examples, machine learning modules may be plugged into and removed from machine learning system 706 (e.g., in order to add or remove support for various corresponding wellness measures). Likewise, action engine 708 may be implemented as a set of action modules. Action modules may be plugged into and removed from action engine 708 in order to add or remove support for performing various actions. For instance, in one example, an action module may be added in order to support the performance of an additional action (e.g., send text messages with social engagement tips). Plugging in and removing engines and module may involve installing and uninstalling software, configuring a software system to use or not use the engines or modules, and so on.

Furthermore, because data preparation system 700, classification engines 702, machine learning system 706, and action engine 708 may be implemented in a modular fashion, the modules included in data preparation system 700, classification engines 702, machine learning system 706, and action engine 708 may be distributed among various devices, such as one or more of ear-wearable devices and devices 106 of computing system 104. For instance, in some examples, processing circuit(s) 206 of ear-wearable device 102A (FIG. 2) may perform one or more data preparation processes that prepare data by other components of wellness evaluation system 602. Furthermore, in some examples, processing circuit(s) 206 of ear-wearable device 102A may implement one or more of classification engines 702 that generate classification data based at least in part on data generated by sensors 210. In such examples, the classification data may classify various aspects of the user's activities and experiences.

For example, the classification data may indicate the types of locations visited by the user of ear-wearable device(s) 102. In some examples, radio 202 of ear-wearable device 102A may transmit the classification data to another computing device, which may in turn perform other operations of wellness evaluation system 602 using the classification data. For instance, the other computing device may implement some or all modules of machine learning system 706, action engine 708, additional classification engines 702, additional data preparation processes, and so on. In such examples where processing circuit(s) 206 of ear-wearable device 102A implement one or more of classification engines 702, because ear-wearable device 102A does not necessarily transmit the data generated by sensors 210 to another computing device, this data does not leave ear-wearable device 102A, which may reduce privacy concerns. For example, the classification data transmitted to the other computing device may indicate that the user of ear-wearable device 102A visited one or more restaurants in the past week but does not necessarily include the data used to make the determination that the user of ear-wearable device 102A visited the one or more restaurants. For instance, in this example, the transmitted data might not indicate which restaurants the user visited or when the user visited the restaurants.

Figure 8:
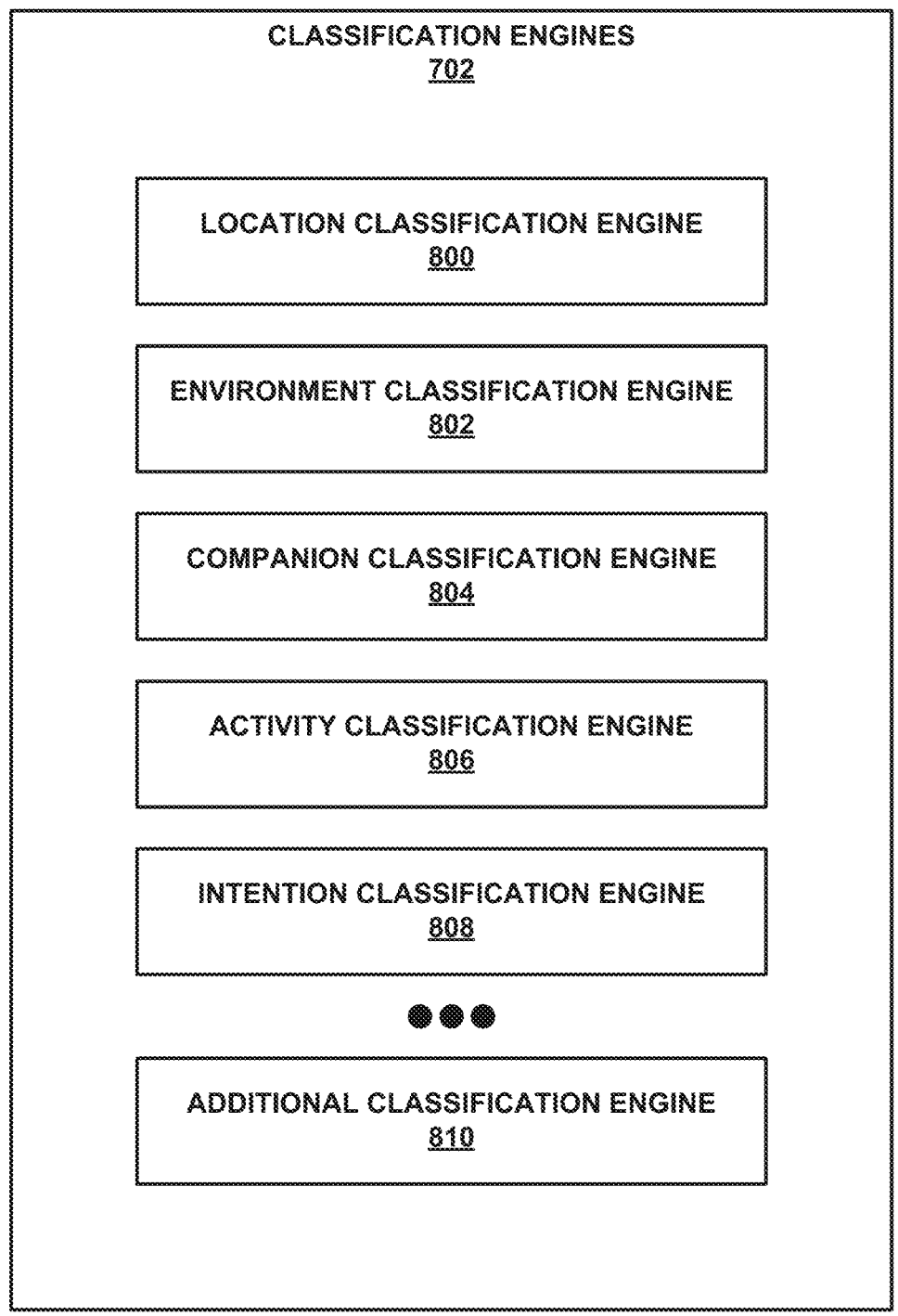
FIG. 8 is a block diagram illustrating examples of classification engines that may be implemented in accordance with the techniques of this disclosure.

FIG. 8 is a block diagram illustrating examples of classification engines 702 that may be implemented in accordance with the techniques of this disclosure. In the example of FIG. 8, classification engines 702 include a location classification engine 800, an environment classification engine 802, a companion classification engine 804, an activity classification engine 806, and an intention classification engine 808. As shown in the example of FIG. 8, classification engines 702 may include one or more additional classification engines 810. In other examples, classification engines 702 may include more, fewer, or different classification engines than shown in the example of FIG. 8.

Each of classification engines 702 may receive input data and generate classification data. Different classification engines 702 may have different input data and classification data. The classification data generated by classification engines 702 may provide various types of information that machine learning system 706 may use to determine achieved levels of one or more wellness measures or other statistical data. The other statistical data may include statistics regarding achieved levels of the one or more wellness measures.

In the example of FIG. 8, the classification data generated by location classification engine 800 may indicate a classification of a location visited by the user of ear-wearable device(s) 102. For example, the classification data generated by location classification engine 800 may indicate that the user has visited or is at a restaurant, a movie theatre, a store, a sports venue, a residence, a place of worship, a park, or another type of location.

Location classification engine 800 may classify the locations visited by the user of ear-wearable device(s) 102. Location classification engine 800 may generate various types of classification data that provide information about the locations visited by the user of ear-wearable device(s) 102. For example, location classification engine 800 may generate information indicating how often the user leaves his or her house, how far the user travels from home, how often the user traverses geographic boundaries (e.g., rivers, state borders, county lines, neighborhood boundaries, etc.), information indicating the variety of places that the user visits, and so on. In some examples, location classification engine 800 may generate classification data that indicate a category of location at which the user is currently located. For example, the location engine may characterize the environment at a particular location. In other examples, the location engine may characterize a location based upon the types of BLUETOOTH™ devices (e.g., appliances, medical devices, personal communication devices, etc.) that advertise their wireless addresses at or about the particular location. In some examples, suitable BLUETOOTH™ direction of arrival location schemes may be utilized to characterize aspects of a particular location. In other examples, a particular location or type of location may be identified by the Wi-Fi networks available at or about the location. As previously stated, location classification engine 800 may be located remotely from the location and may be further adapted to send or receive information regarding the location with one or more other users and beacons, such as the techniques described in U.S. Patent Publication No. 2018/0233018, filed Feb. 13, 2018, entitled FALL PREDICTION SYSTEM INCLUDING A BEACON AND METHOD OF USING SAME.

In some examples, location classification engine 800 may generate profile information regarding people who go to places visited by the user. Visiting places associated with diverse types of people may be associated with better health outcomes. For instance, if the user of ear-wearable device(s) 102 is a senior citizen, it may be healthy for the user to visit places that younger people also visit so that the user's universe of opportunities for social engagement is not limited only to social engagement with other senior citizens.

Accordingly, the profile information generated by location classification engine 800 may indicate types of people that visit the places visited by the user. In this example, a first phase of location classification engine 800 may identify places visited by the user and a second phase of location classification engine 800 may generate the profile information based on the list of identified places visited by the user. In some examples, to generate the profile information, location classification engine 800 may access a database that maps locations to profiles of people who visit the locations. For instance, in one example, the database maps locations to categories in one or more dimensions. Example dimensions may include typical ages of visitors at a location, typical wellness level scores of people at the location, typical numbers of people concurrently at the location, demographic information of visitors to the location, and so on.

Environment classification engine 802 generates classification data that classifies the environments to which the user of ear-wearable device(s) 102 is exposed. Exposure to different types of environments, such as acoustic environments, may be correlated with more complex social interactions, which in turn may be associated with better health outcomes. For example, environment classification engine 802 may classify an acoustic environment as quiet, an acoustic environment that includes the sound of human voices, a restaurant, distant talking, speech in reverberant room, various modes of transportation e.g., automobiles, trains, motorcycle, train stations, subways, airplanes, airports, etc. (which would also relate to the individual's mobility), outdoors, music, cinema, theater, lecture, classroom, auditoriums, library, gymnasiums, sport spectating, sporting, pub, church, amusement parks, doctor's office, lobby/waiting area, barnyard, casino, bingo hall, office setting, courtroom, emergency situations, large groups, small groups, shopping, grocery checkout, bank, cocktail party, lawn mower, conversation in the street, barber shop, factory, daycare, clattering dishes, etc. There are also transitory noises that might provide further context beyond just location: footsteps/footfalls, laughter, applause, crying, dog barking, coughing, chewing/swallowing, machine noise, household appliances, water boiling, running water, toilet flushing, door creaking, door slamming, wind noise, printing noise, alarms, hammering nails, children's voices, children's play, infant cooing, opening Champaign bottle, etc.

Companion classification engine 804 generates classification data that classifies the companions of the user of ear-wearable device(s) 102. Having conversations with a variety of different people may be correlated with better health outcomes. Hence, in some examples, companion classification engine 804 may generate classification data that categorize the people with whom the user is conversing. As an illustration, categories may include family member, friend, caregiver, or other type of person. It is possible for a conversational partner to have one or more different categories assigned to them. In some examples, companion classification engine 804 determines that the user is communicating with the user's self, e.g., when the user is 'thinking out loud', 'debating with one's self', or displaying signs of having multiple personalities. It may be determined by machine learning system at 706 that having conversations with one's self or with certain other individuals may, alternatively, be correlated with poorer health outcomes, e.g., increased stress, higher blood pressure, physical or emotional abuse, and so on.

Companion classification engine 804 may use various types of input data to categorize the people with whom the user is conversing. For example, data preparation system 700 may process sound detected by ear-wearable device(s) 102 or another operatively connected microphone to generate a voice print. The voice print may comprise information that characterizes a voice of a person. Various technologies may be used to generate voice prints, such as frequency estimation, formant classification, hidden Markov models, Gaussian mixture models, pattern recognition algorithms, matrix representation, vector quantization, and decision trees. For comparing utterances against voice prints, neural networks, cosine similarity, and so on. Spectral features may be used in representing speaker characteristics. In an example where data preparation system 700 generates a voice print, the input data used by companion classification engine 804 may include the voice print. In some examples where ear-wearable device(s) 102 are used in a phone call, the input data used by companion classification engine 804 may include a phone number associated with the person with whom the user is conversing.

In some examples, a device associated with the user of ear-wearable device(s) 102 (e.g., ear-wearable device(s) 102 or another device) may detect wireless network identifiers of computing devices that are within wireless reception range of the device. The detected wireless network identifiers may include wireless network identifiers of computing devices associated with third-parties who are in the vicinity of the user of ear-wearable device(s) 102. In such examples, the input data of companion classification engine 804 may include data based on the wireless network identifiers of computing devices associated with third-parties. For example, the input data may include a set of BLUETOOTH™ identifiers of computing devices associated with third-parties. In some examples, the third-party BLUETOOTH™ identifiers may be obtained through a paired connection between devices. In some other examples, the third-party BLUETOOTH™ identifiers may be obtained through one or more of a device address advertisement or through eavesdropping. In some examples, companion classification engine 804 may use a mapping from wireless network identifiers to third-parties to identify the third-parties who are in the vicinity of the user of ear-wearable device(s) 102.

In some examples, companion classification engine 804 does not use a mapping from wireless network identifiers to third-parties. Rather, in such examples, companion classification engine 804 may use the detected wireless network identifiers as a proxy for the diversity of people who are in the vicinity of the user of ear-wearable device(s) 102. Thus, companion classification engine 804 may generate, based on the detected wireless network identifiers, classification data indicating one or more of an estimate of the number of people and the identity or identities of people who are in the vicinity of the user of ear-wearable device(s) 102.

In some examples, the input data used by companion classification engine 804 includes one or more of social media, personal correspondence, and calendar data. The social media, personal correspondence, and calendar data may include data indicating appointments of the user of ear-wearable device(s) 102. The social media and calendar data may also indicate who the user is planning to meet during the appointments. Companion classification engine 804 may generate classification data that classify the people that the user is planning to meet during the meet during the appointments. In some examples, the input data used by companion classification engine 804 may include data that may enable companion classification engine 804 to determine whether the user kept appointments on the user's calendar. For instance, the input data used by companion classification engine 804 may include location data that companion classification engine 804 may use to determine whether the user went to locations specified by the calendar data for the appointments. In another example, the input data used by companion classification engine 804 may include server data that companion classification engine 804 may use to determine whether the user logged into a virtual meeting specified by the calendar data for the appointments. Breaking appointments may, for example, be a sign of declining cognitive or physical health.

Activity classification engine 806 generates classification data that identifies the activities performed by the user of ear-wearable device(s) 102. In other words, activity classification engine 806 may categorize the activities that the user performs. Performing a variety of different types of activities may be correlated with better health outcomes. Example types of activities may include running, walking, watching television, sleeping, talking on the telephone, traveling, engaging in conversation, participating in group activities or meetings, exercising, sitting still, and so on.

Activity classification engine 806 may use a variety of different types of input to determine the activities performed by the user of ear-wearable device(s) 102. For example, the inputs to activity classification engine 806 may include data based on signals from IMU 220, data based on signals from microphone 208, and so on.

Intention classification engine 808 may generate classification data that identify whether the user is engaged in intentional listening. In other words, intention classification engine 808 may classify a level of intent with which the user of ear-wearable device(s) 102 is engaged in a conversation. A user of ear-wearable device(s) may engage in intentional listening when the user is actively listening with the intention to engage in conversation or absorb information provided in human-directed communication. In contrast, the user may be engaged in passive 'listening' when the user is able to hear speech sounds or observe human-directed communication efforts but is not actively absorbing information in the speech sounds or human-directed communication efforts. Outputs of intention classification engine 808 may include data indicating amounts or percentages of time in which the user engaged in intentional 'listening'. In some examples, outputs of intention classification engine 808 may include data indicating amounts or percentages of time in which the user engaged in intentional listening relative to passive listening.

Intention classification engine 808 may use various types of input data. For example, the input data used by intention classification engine 808 may include data based on signals from IMU 220, data based on signals from microphone 208, EEG data based on signals generated by EEG sensor 226 (FIG. 2), and so on. Particular types of mental activities or states are frequently associated with different EEG signals. For example, alertness, daydreaming, and sleep are associated with different patterns in EEG signals.

In some examples, changes in emotional state, e.g., emotional reactions to what the user has, e.g., heard, may be associated with active listening. There are various methods by which intention classification engine 808 may characterize the emotional state of the user. For example, the input data used by intention classification engine 808 may include data based on signals from a microphone 208, EEG data based on signals generated by EEG sensor 226 (FIG. 2), data based on signals generated by blood pressure sensor, and so on. For example, prosody of speech may be associated with the emotional state of a talker. Prosody of speech refers to characteristics of speech such as intonation, stress patterns, loudness variations, pausing, speech rate and rhythm.

As an illustration, an emotion such as "anger" may be expressed in vocal utterances with a lower pitch, higher intensity, higher first formant frequency, and faster attack times at voice onset. In contrast, "hot anger" may be expressed with a higher, more varied pitch frequency, and even greater energy. In comparison to neutral speech, sad emotions are produced with a higher pitch frequency, less intensity, longer duration with more pauses, and a lower first formant frequency. Expressions of fear often have a higher pitch frequency with relatively little variation, lower energy, and a faster speech rate with more pauses. Feelings of disgust are often expressed with a lower, downward directed pitch frequency with relatively little variation, a lower first formant frequency, and fast attack times and shorter durations.

In some examples, one of classification engines 808 may be adapted to detect instances of bullying, abuse, or abusive relationships (e.g., elder abuse, child abuse, domestic abuse, etc.) between the user of ear-wearable device(s) and the user's communication partners. For example, the classification engine may generate classification data that identifies sounds, such as speech, detected in the environment of the user of ear-wearable device(s) that may be associated with potential abuse. For instance, a neural network of the classification engine may be trained to identify aggressive speech, sounds of physical abuse, and so on. As described elsewhere in this disclosure, content analysis may be performed on human-directed communication and abusive or manipulative content may be detected based on such analyses. Additionally, in this example, wellness evaluation system 602 (e.g., the classification engine, another one of classification engines 702, or machine learning system 706) may generate statistical data or classification data based on probabilities that the user of the ear-wearable device(s) 102 is experiencing certain types of emotions characteristic of victims of bullying or abuse, such as fear, anxiousness, sadness, or depression. Machine learning system 706 of wellness evaluation system 602 may use such information to generate statistical data indicating a probability that the user of ear-wearable device(s) 102 is involved in an abusive relationship with another person. In some examples, this statistical data may be used to perform various actions, such as activating additional sensors, generating alerts, and so on.

Particular conversational patterns are associated with active listening or engagement. In a similar way, particular conversational patterns are associated with level of language development or with outcomes of disorders that are associated with language proficiency or pathology. For instance, turn taking is typically associated with active listening while extended periods of time where the user does not make a make an utterance with a conversational partner may be associated with lack of engagement. Conversational turn-taking may also be a marker of language development or proficiency. Furthermore, the content and complexity of the user's utterances may be associated with one or more of the user's degree of active listening and language development or proficiency. For example, simply restating aspects of what a conversational partner has previously said, e.g., mimicry, may be associated with a lack of active listening; whereas, utterances where the user introduces novel conversational contents or challenges previous contents may be associated with active listening. Any suitable method of content analysis and comparison may be utilized.

In some examples, a classification engine of wellness evaluation system 602 may analyze communication efforts of the user for possible pathology. In other words, the classification engine may classify the user's communication efforts with respect to one or more possible pathologies. For example, changes in speech complexity (e.g., semantic complexity, grammatical incompleteness, etc.) or fluency (e.g., atypical pause patterns) may be a sign of aphasia or symptoms of a stroke or traumatic brain injury.

Machine learning system 706 of wellness evaluation system 602 may use such information to generate statistical data indicating a probability that the user of ear-wearable device(s) 102 has a particular pathology. In some examples, this statistical data may be used to perform various actions, such as activating additional sensors, generating alerts, and so on.

Furthermore, particular types of head movements and orientations are associated with active listening. For instance, a level head pose and side-to-side head movements are typically associated with active listening while upward or downward tilted head pose without side-to-side head movements may be associated with lack of engagement. Furthermore, lack of head movement in response to voices coming from different directions may be associated with lack of engagement, and therefore passive, rather than active, listening. In addition, seemingly sporadic head movements and orientations may be associated with possible attention deficits, hyperactivity disorders, or anxiety. IMU 220 (FIG. 2) may generate signals indicative of the movement and orientation of the user's head. Accordingly, in some examples, the input data used by intention classification engine 808 may include information based on signals generated by IMU 220.

In further examples, it may be possible for wellness evaluation system 602 to determine the type of stroke or brain injury that an individual may be experiencing or have experienced previously. For example, Wernicke's Aphasia is characterized by receptive language comprehension difficulties. In this example, the wellness evaluation system may utilize content analyses to determine that an individual is not understanding what is being communicated to them by others, and/or the individual may not realize that utterances that they are using are nonsensical (e.g., the individual may string together a series of meaningless words that sound like a typical sentence but carries no little linguistic meaning to others). In another example, Broca's Aphasia is characterized by expressive language difficulties. In this example, the wellness evaluation system may utilize content analyses to determine that the individual is not properly adhering to typical language conventions (e.g., the individual may utter some words that convey meaning but omit grammatical words like "is" or "the"; thereby making the utterance difficult for others to understand).

In some examples, wellness evaluation system 602 may be adapted to monitor the progress of an individual during rehabilitation, e.g., after a stroke. As described elsewhere in this disclosure, wellness evaluation system 602 may be adapted to differentiate between voices of the user and the voices of the user's communication partners. In some examples, the individual being evaluated for a pathology may be the user of the ear-wearable system 102A. Furthermore, in some examples, the individual being evaluated for a pathology may be a communication partner relative to the user of the ear-wearable system 102A. For example, the user may be a caregiver for the individual who has a pathology; therefore, the user would have an interest in knowing the rehabilitation progress of the individual with the pathology.

As mentioned above, the set of classification engines 702 may include one or more additional classification engines. For instance, in one example, one of the additional classification engines may generate classification data that classify the user's pattern of news sources from which the user receives television or radio news. In this example, the classification engine may generate classification data that classify the user as being a person who only receives news from a limited number of new sources or as being a person who receives news from news sources with diverse sets of views. In this example, receiving news from a greater array of news sources may be associated with greater levels of social complexity.

In another example, the additional classification engines may additionally or alternatively include a fall risk classification engine. The fall risk classification engine may generate classification data that classify the risk of the user of ear-wearable device(s) 102 experiencing a fall. In this example, the fall risk classification engine may use inputs based on signals from IMU 220 (FIG. 2), heart rate sensor 222 (FIG. 2), a blood pressure sensor, a blood perfusion sensor, EEG sensor 226, and/or other types of sensors using any suitable technique or techniques, such as those described in U.S. Provisional Patent Application No. 62/785,295, entitled PREDICTIVE FALL EVENT MANAGEMENT SYSTEM AND METHOD OF USING SAME, filed on Dec. 27, 2018. In some examples, action engine 708 may generate outputs that activate or deactivate one or more sensors based on the fall risk classification determined by the fall risk classification engine. For instance, fall risk classification engine may use data based on signals from IMU 220 to initially determine that the user of ear-wearable device(s) 102 is at an elevated risk of falling. In this example, based on this initial determination of the user's fall risk, action engine 708, to refine the fall risk classification, action engine 708 may generate output to activate one or more additional sensors, such as a blood perfusion sensor, that generate data that the fall risk classification engine may use to refine the user's fall risk classification.

One or more of classification engines 702 may be implemented using machine learning technologies. For example, one or more of classification engines 702 may be implemented using machine learning systems, such as ANNs or other machine learning techniques. A machine learning module used in one of classification engines 702 may be trained to perform the classification task of the classification engine. For example, a machine learning module of location classification engine 800 may be trained to generate classification data that classify a location visited by the user based on one or more input data. In some examples, one or more of the machine learning modules are fully trained prior to starting use of wellness evaluation system 602 with respect to the user of ear-wearable device(s) 102. In some examples, wellness evaluation system 602 continues to train one or more of the machine learning modules after starting to use wellness evaluation system 602 with respect to the user of ear-wearable device(s) 102. In some examples, one or more of classification engines 702 may be implemented as a set of business rules, implemented using imperative programming, or implemented using other types of programming techniques.

As mentioned above, one or more components of wellness evaluation system 602 may be trained to recognize the voice of the user of ear-wearable device(s) 102. Furthermore, in some examples, one or more components of wellness evaluation system 602 may be trained to recognize the voices of other or more other people. Wellness evaluation system 602 may use various techniques for recognizing the user's voice and other peoples' voices. For instance, wellness evaluation system 602 may be trained to recognize patterns in communication patterns of the user, such as: fundamental frequency of voice, spectral distribution of voice formants, prosody patterns, communication content, mannerisms, and the like. In a least one example, wellness evaluation system 602 may differentiate the user's voice sounds from other peoples' voice sounds based on signals generated by directional microphones in ear-wearable device(s) 102. In this example, the direction of origin of a voice sound can be determined based on the signals from an array of operatively connected microphones (e.g., directional microphones) and a model of the relative positioning of the array of microphones. For example, if the direction of origin of a voice sound is between the forward direction of a binaural set of microphones as part of a pair of ear-wearable device(s) 102, then the voice sounds may be determined to be the sounds of the user's own voice. In another example, if the sound pressure level of one voice is substantially louder than that of another voice, then it may be determined that the louder voice is that of the user and the softer voice is that of the communication partner. In yet another example, wellness evaluation system 602 may differentiate the user's voice sounds from other peoples' voice sounds based on signals from own-voice sensors, such as accelerometers, placed in or about one or more of the user's ear or ear canals. In examples where the own-voice sensors comprise accelerometers, the user's act of speaking may cause movements and/or vibrations detectable in the user's ear canal that would otherwise not be present for other peoples' voices. Thus, in these examples, the fact that ear-wearable device(s) 102 may include sensors at or about the user's ears may help wellness evaluation system 602 to robustly identify the user's own voice e.g., as compared to systems that do not involve ear-wearable devices.

In some examples, data preparation system 700 may annotate audio and other human-directed communication data with information that identifies segments of the communication data that contain the user's voice or gestures, identifies segments of the communication data that contain other peoples' voice or gestures, and so on. One or more of classifications engines 702 may use the annotated communication data for classification purposes. In other examples, one or more of classification engines 702 may recognize the user's communication efforts or other peoples' communication efforts as part of generating classification data.

In some examples, the classification data generated by one or more of classification engines 702 is associated with at least one statistic. For example, a confidence value or interval may indicate a level of confidence that a classification made by a classification engine is accurate. For example, location classification engine 800 may generate classification data that indicates a confidence level that the user of ear-wearable device(s) 102 is at a particular type of location. For instance, in this example, location classification engine 800 may generate classification data that indicate an 80% confidence level that the user of ear-wearable device(s) 102 is currently at a restaurant. It should be understood that any suitable statistic may be associated with the classification data.

Figure 9:
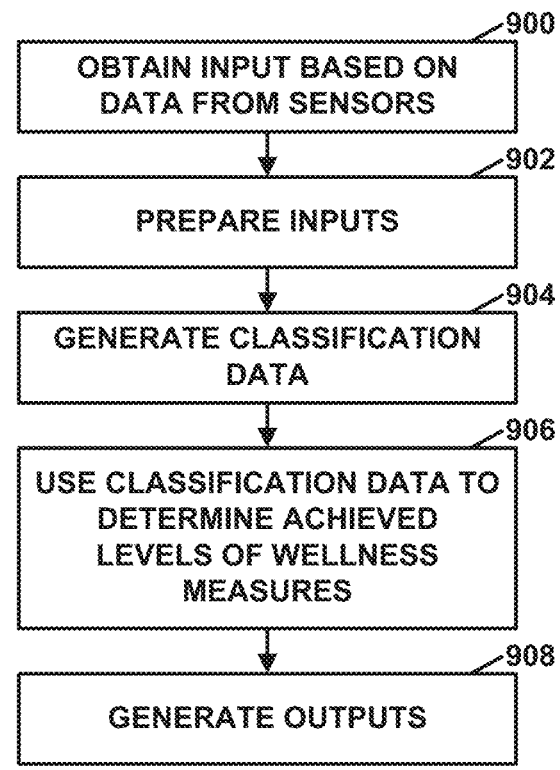
FIG. 9 is a flowchart illustrating an example operation of the wellness evaluation system that is implemented in accordance with the techniques of this disclosure.

FIG. 9 is a flowchart illustrating an example operation of wellness evaluation system 602 that is implemented in accordance with the techniques of this disclosure. The flowcharts of this disclosure are provided as examples. In other examples, operations shown in the flowcharts may include more, fewer, or different actions, or actions may be performed in different orders or in parallel.

In the example of FIG. 9, wellness evaluation system 602 may obtain inputs 604, which may be based on data from one or more sensors (e.g., one or more of sensors 210 (FIG. 2)) (900). For instance, in some examples, wellness evaluation system 602 may obtain one or more of inputs 604 from a data storage system, from a computer-readable medium, directly from a sensor, or otherwise obtain inputs 604.

Furthermore, in the example of FIG. 9, data preparation system 700 of wellness evaluation system 602 may prepare inputs 604 for use in classification engines 702 (902). Data preparation system 700 may prepare inputs 604 in accordance with any of the examples provided elsewhere in this disclosure. Classification engines 702 may generate classification data based on the prepared inputs (904). Classification engines 702 may generate the classification data in accordance with any of the examples provided elsewhere in this disclosure.

Machine learning system 706 of wellness evaluation system 602 may use the classification data to determine achieved levels of one or more wellness measures (906). In some examples, machine learning system 706 may use the classification data or other types of data (including e.g., achieved levels of one or more wellness measures) to determine statistical data. Such statistical data may include statistics (e.g., averages, deviations, distributions, probabilities, etc.), of the achieved levels of one or more wellness measures. Machine learning system 706 may determine the achieved levels of one or more wellness measures and statistical data in accordance with any of the examples provided elsewhere in this disclosure. Machine learning system 706 may determine the most effective outputs 606 that are generated by action engine 708 for a specific user or relative to a specific context of the user in accordance with any of the examples provided elsewhere in this disclosure. Additionally, in the example of FIG. 9, action engine 708 generates outputs 606 (908). Action engine 708 may generate one or more of outputs 606 based on the achieved levels of the wellness measures and/or statistical data determined by machine learning system 706. Action engine 708 may generate outputs 606 in accordance with any of the examples provided elsewhere in this disclosure. For instance, in some examples, action engine 708 may include routines that map particular achieved levels of the wellness measures and/or statistical data to particular outputs.

Figure 10:
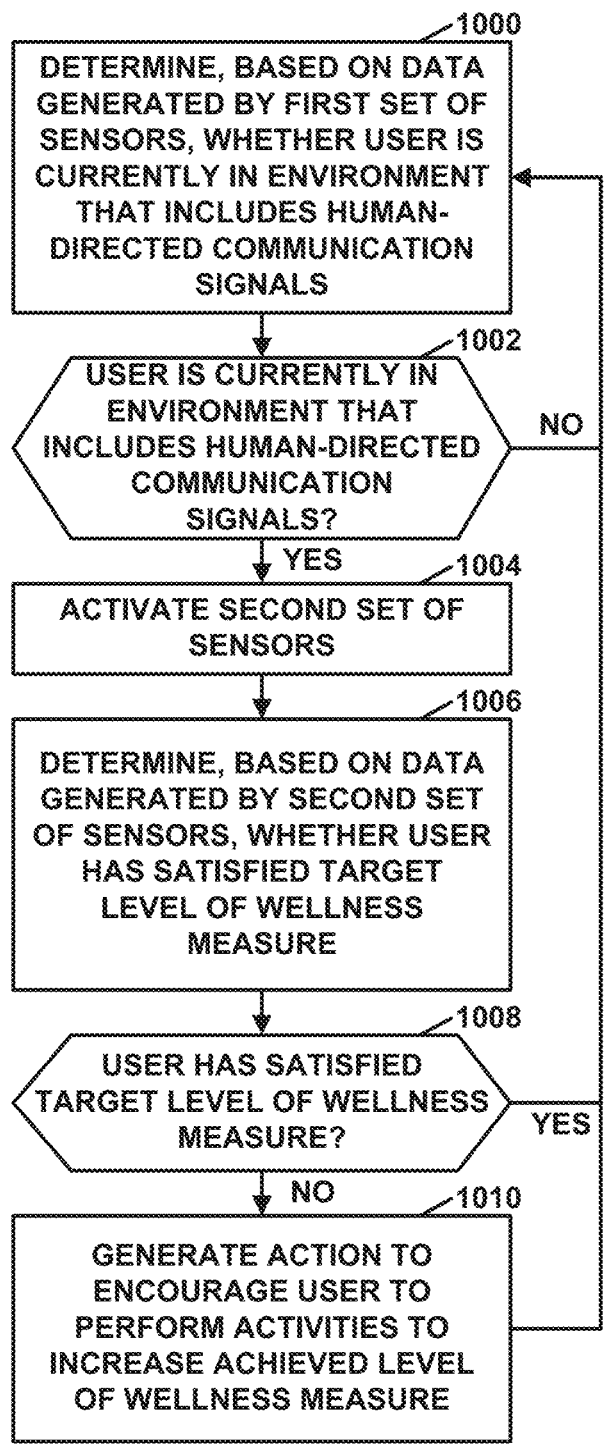
FIG. 10 is a flowchart illustrating an example operation of the wellness evaluation system in which additional sensors are activated, in accordance with the techniques of this disclosure.

FIG. 10 is a flowchart illustrating an example operation of wellness evaluation system 602 in which additional sensors are activated, in accordance with the techniques of this disclosure. The operation of FIG. 10 is one of many examples that may be implemented using wellness evaluation system 602.

In the example of FIG. 10, wellness evaluation system 602 (FIG. 6) may determine, based on data generated by the first set of sensors powered by one or more batteries (e.g., battery 212 (FIG. 2)) or other sources of power of ear-wearable device(s) 102, that the user is currently in an environment that includes human-directed communication signals (1000). As discussed elsewhere in this disclosure, one or more processing circuits may implement wellness evaluation system 602. In some examples, environment classification engine 802 (FIG. 8) of wellness evaluation system 602 may determine whether the user of ear-wearable device(s) 102 is currently in an environment that includes human-directed communication signals, such as human voices.

In the example of FIG. 10, if the user is not currently in an environment that includes human-directed communication signals ("NO" branch of 1002), wellness evaluation system 602 may continue to obtain data based on the first set of sensors and determine whether the user is currently in an environment that includes human-directed communication signals (1000). In response to determining that the user is currently in the environment that includes human-directed communication signals ("YES" branch of 1002), wellness evaluation system 602 may activate a second set of one or more sensors of ear-wearable device(s) 102 such that the set of batteries provides a second amount of power greater than a first amount of power to the second set of sensors (1004). Prior to activation of the second set of sensors, the batteries may provide the first amount of power to the second set of sensors. In some examples, the first amount of power may be no power. The second amount of power to the second set of sensors may result in delivery of an increased amount of overall power, e.g., to the second set of sensors, relative to the amount of power provided only to the second set of sensors prior to activating the second set of sensors. One or more of outputs 606 generated by action engine 708 (FIG. 7) of wellness evaluation system 602 may include commands to activate the second set of sensors. In some examples, one or more of ear-wearable device(s) 102 includes the second set of sensors. In some examples, one or more body-worn devices other than ear-wearable device(s) 102 may include one or more sensors in the second set of sensors.

In some examples, prior to receiving the increased amount of power, the set of batteries may have been providing no power to the second set of sensors. Furthermore, in some examples, the increased amount of power provided to the second set of sensors may be sufficient for the second set of sensors to generate data.

The second set of sensors may include at least one sensor that is not included in the first set of sensors. For instance, in one example based on the example of FIG. 2, the first set of sensors may include microphone 208, but not EEG sensor 226. However, in this example, the second set of sensors includes EEG sensor 226.

Additionally, in the example of FIG. 10, wellness evaluation system 602 may determine, based on data generated by the second set of sensors, whether the user has satisfied a target level of a wellness measure (1006). For instance, in some examples, to determine whether the user has satisfied a target level of the wellness measure, wellness evaluation system 602 may determine an achieved level of the wellness measure. For instance, in some examples, machine learning system 706 (FIG. 7) of wellness evaluation system 602 may determine the achieved level of the wellness measure. Wellness evaluation system 602 may then compare the achieved level of the wellness measure and associated statistics with the target level of the wellness measure. For instance, in some examples, action engine 708 may compare the achieved level of the wellness measure with the target level of the wellness measure.

In the example of FIG. 10, in response to determining that the user has satisfied the target level of the wellness measure ("YES" branch of 1008), wellness evaluation system 602 may perform various actions, such as deactivating the second set of sensors and/or continuing to obtain inputs and determine whether the user is in an environment that includes human-directed communication signals (1000, 1002).

However, in the example of FIG. 10, based on a determination that the user has not satisfied the target level of the wellness measure ("NO" branch of 1008), wellness evaluation system 602 may perform an action to encourage the user to perform one or more activities to increase an achieved level of the wellness measure (1010). The achieved level of the wellness measure may be a level of the wellness measure achieved by the user. Wellness evaluation system 602 may perform various types of actions to encourage the user to perform one or more activities to increase the achieved level of the wellness measure. For example, wellness evaluation system 602 may generate a notification message that provides a tip on how to improve the achieved level of the wellness measure.

In various examples, the wellness measure may be one of various types of measures of the mental and/or physical wellness of the user of ear-wearable device(s) 102. For example, the wellness measure may be a social engagement measure. The social engagement measure may be a measure of complexity of social engagement of the user of ear-wearable device(s) 102. As another example, the wellness measure may be a language development measure or language rehabilitation measure. One or more of the language development measure or the language rehabilitation measure may be a measure of complexity of expressive or receptive communication of one or more of the user of ear-wearable device(s) 102 and a communication partner to the user of ear-wearable device(s) 102.

It is noted that in other examples, wellness evaluation system 602 may perform actions other than or in addition to actions to encourage the user to perform one or more activities to increase the achieved level of the wellness measure. For instance, in other examples, wellness evaluation system 602 may generate alerts that warn third-parties about a condition of the user of ear-wearable device(s) 102. In some examples, wellness evaluation system 602 may generate alerts that warn third-parties about an unhealthy or abusive relationships between a user of the ear-wearable device(s) 102 and a communication partner. Furthermore, in some examples, such as examples where the wellness measure is a measure of the complexity of social engagement, wellness evaluation system 602 may generate a visual representation of the measure of complexity of social engagement of the user. For instance, wellness evaluation system 602 may generate a GUI that includes a chart or graph that represents the complexity of social engagement of one or more of the user and a social group. In the example of FIG. 7, machine learning system 706 may include a machine learning module (e.g., an ANN) that is trained using labeled examples to determine the complexity of social engagement of the user. Furthermore, in some such examples, the visual representation of the measure of complexity of social engagement of the user may comprise a visual representation of a comparison to a typical level of the wellness measure achieved by a population or group of individuals. For instance, the visual representation of the comparison may comprise a bar chart that compares the complexity of social engagement of the user with the typical level of the wellness measure among other individuals.

Figure 11:
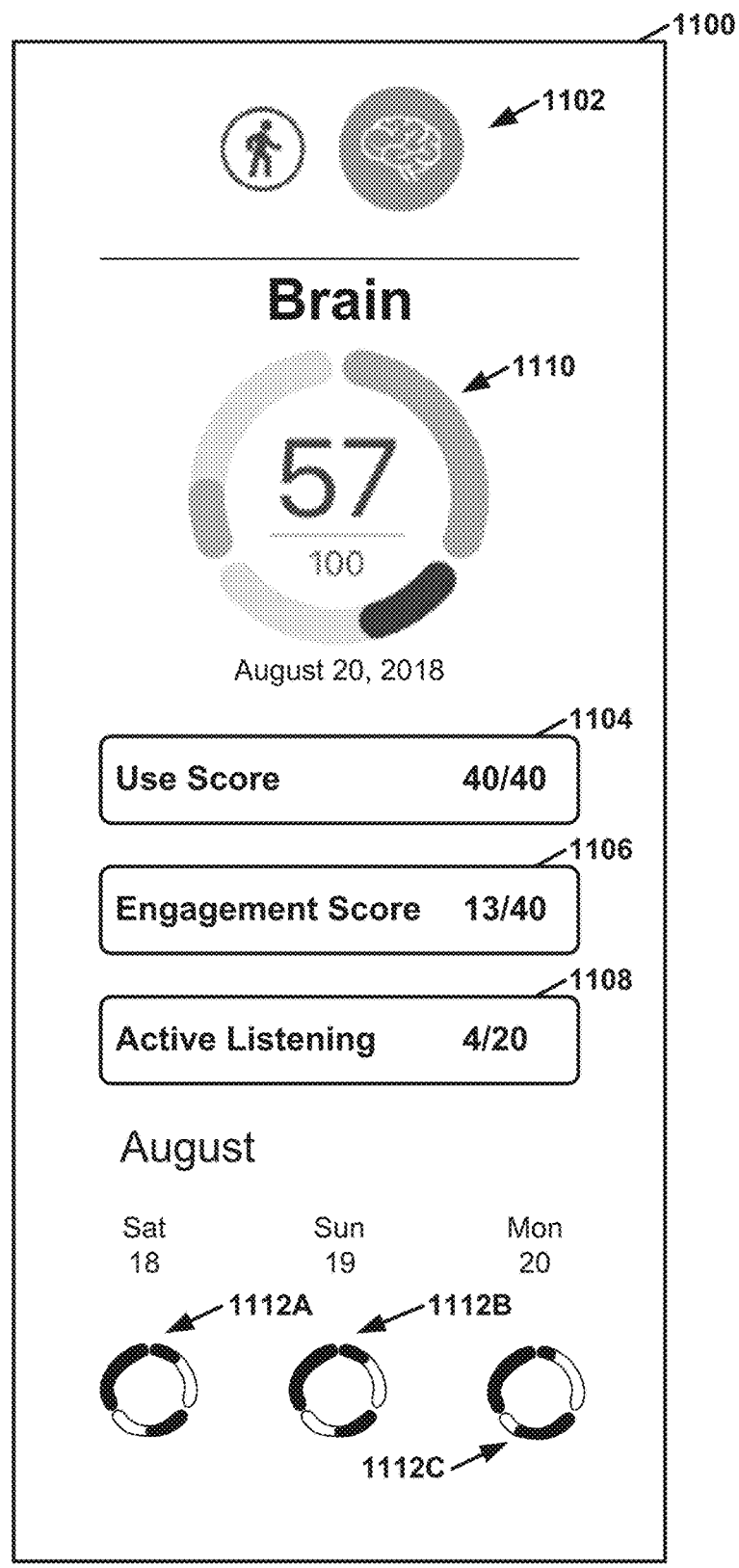
FIG. 11 is an example graphical user interface (GUI) for display of a brain wellness score in accordance with one or more aspects of this disclosure.
Figure 12:
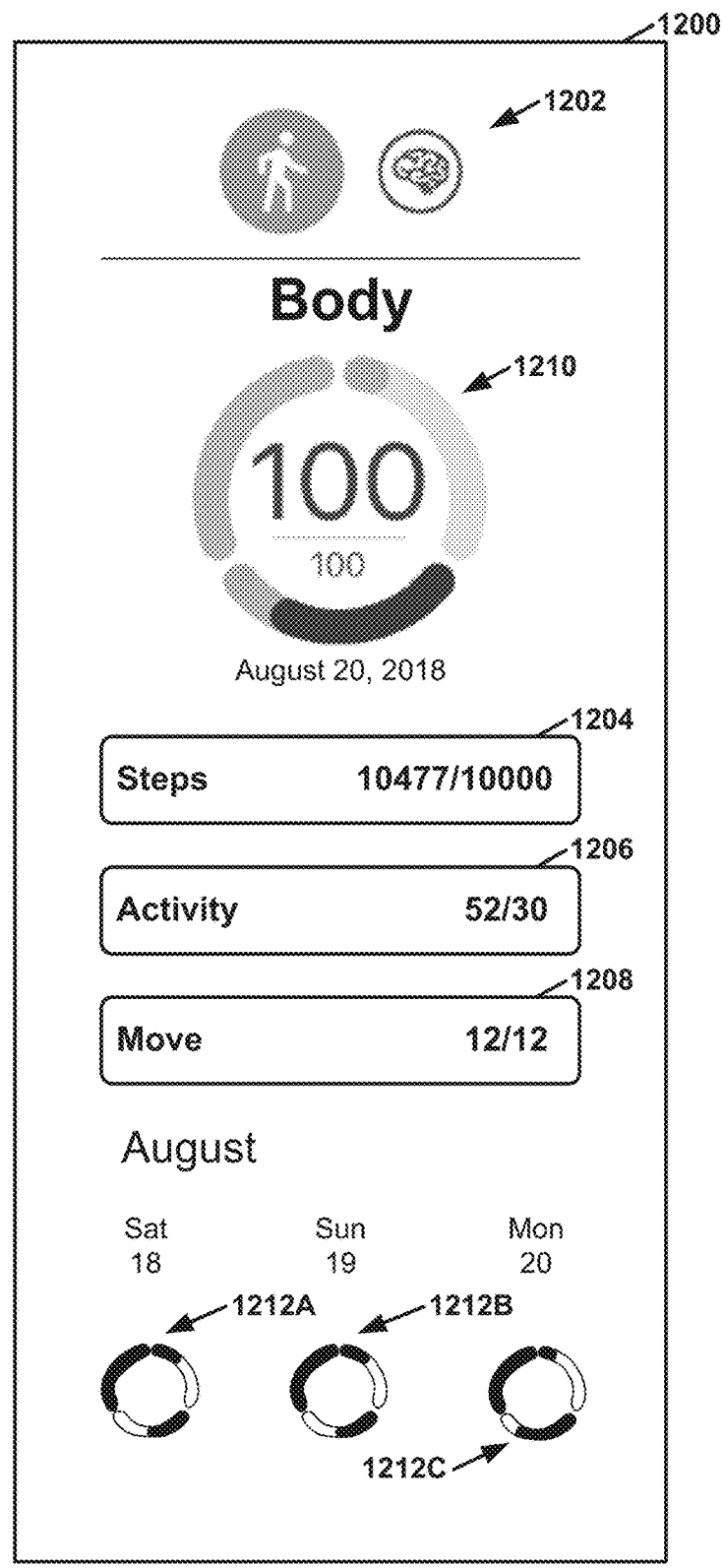
FIG. 12 is an example GUI for display of a body wellness score in accordance with one or more aspects of this disclosure.
Figure 13:
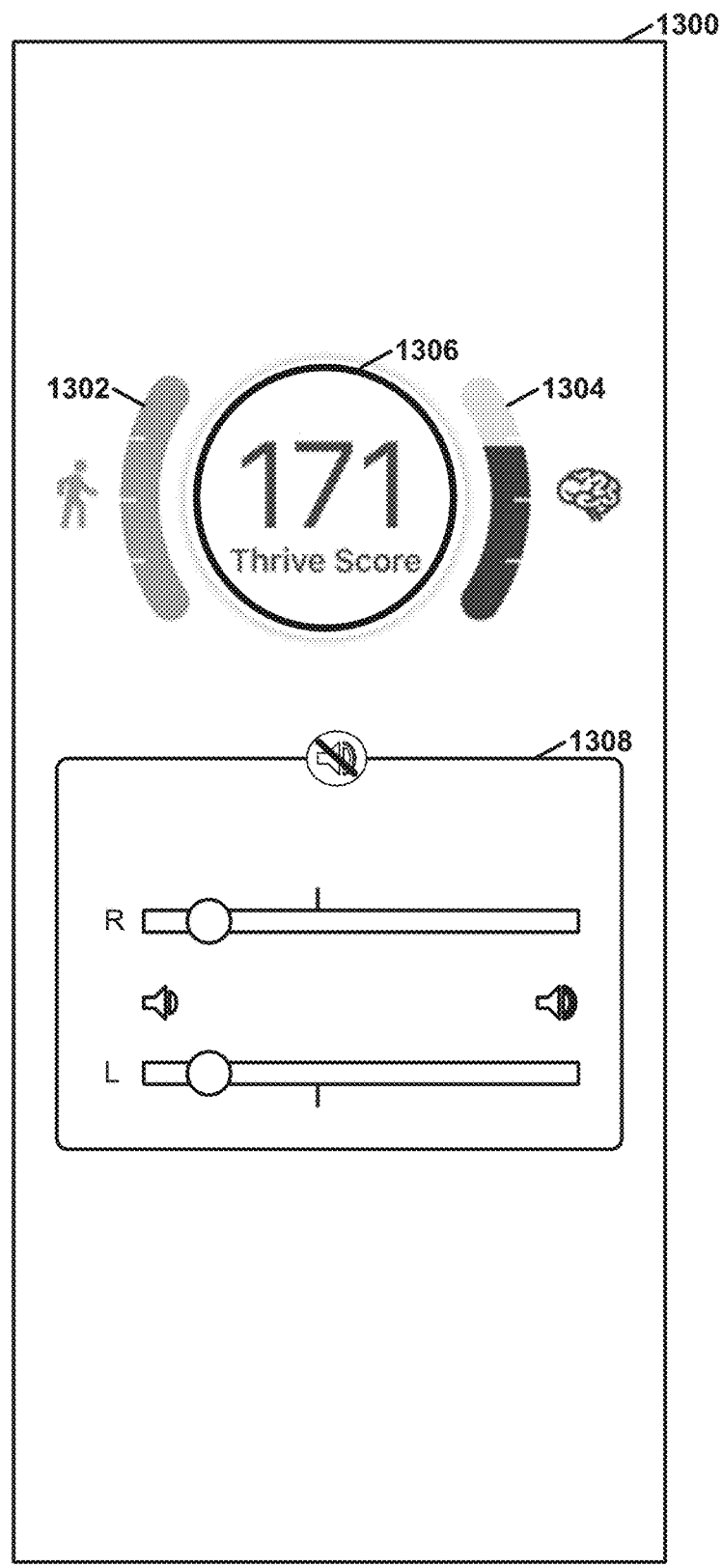
FIG. 13 is an example GUI for display of a wellness measure in accordance with one or more aspects of this disclosure.

In some examples, wellness evaluation system 602 (e.g., parts of wellness evaluation system 602 implemented by companion application 324, third-party companion application 424, or server companion application 524) may generate a GUI that presents the achieved level of the wellness measure. FIG. 11, FIG. 12, and FIG. 13 are example GUIs that may present achieved levels of wellness measures.

Furthermore, in some examples, instead of an achieved level of a wellness measure and a target level of the wellness measure, an example similar to the example of FIG. 10 may apply to a determined statistic. Thus, wellness evaluation system 602 may determine, based on data generated by a first set of sensors powered by one or more batteries of one or more ear-wearable devices, first statistical data regarding a user of ear-wearable device(s) 102. In this example, as in the example of FIG. 10, the batteries provide a first amount of power to a second set of one or more sensors and the second set of sensors may include at least one sensor that is not included in the first set of sensors. Furthermore, wellness evaluation system 602 may determine, based on the first statistical data, whether to activate the second set of sensors such that the one or more batteries provides a second amount of power greater than the first amount of power to the second set of sensors. In this example, wellness evaluation system 602 may determine, based on data generated by the second set of sensors (and in some examples data from the first set of sensors), second statistical data regarding the user. Wellness evaluation system 602 may perform various actions based on the second statistical data.

For instance, in one example, one or classification engines 702 of wellness evaluation system 602 may use data (e.g., IMU signal data) from a first set of sensors (e.g., IMU 220 of FIG. 2) to determine first classification data. In this example, the first classification data may indicate whether movements of the user of ear-wearable device(s) 102 are balance checks. In this example, machine learning system 706 may use the classification data in a fall prediction model to determine first statistical data regarding a first fall probability of the user of ear-wearable device(s) 102. Furthermore, in this example, based on the first statistical data indicating a fall probability exceeding some threshold, action engine 708 may activate a second set of sensors, such as one or more ear-worn PPG sensors that may detect changes in the user's blood perfusion. Subsequently, classification engine 702 may generate second classification data based on signals from the second set of sensors. For instance, classification engine 702 may generate second classification data that classify segments of signals from the PPG sensors into categories regarding whether the signals from the PPG sensors indicate changes in blood pressure that may be associated with the user falling. Machine learning system 706 may use the second classification data as input to a refined fall prediction model that determines second statistical data. The second statistical data may indicate a second fall probability of the user of ear-wearable device(s) 102. Action engine 708 of wellness evaluation system 602 may perform various actions, such as action types described elsewhere in this disclosure, based on second statistical data generated by using the refined fall prediction model. For instance, in some examples, if the second statistical data generated by machine learning system 706 using the refined fall prediction model exceeds a threshold, action engine 708 may generate an alert to a caregiver.

In some examples, classification data generated by one or more of classification engines 702 may indicate whether conversations involving the user are associated with potentially abusive behavior (either by the user of ear-wearable device(s) 102, directed to the user of ear-wearable device(s) 102, or between third parties). In one such example, machine learning system 706 may use this classification data and potentially other data to generate statistical data (e.g., first or second statistical data) that comprises a probability that the user is involved in an abusive relationship with another person. In some examples, machine learning system 706 may use various types of classification data to generate statistical data (e.g., first or second statistical data) that comprises a probability that the user has a pathology.

FIG. 11 is an example GUI 1100 for display of a brain wellness score in accordance with one or more aspects of this disclosure. The brain wellness score is one example of a wellness measure. GUI 1100 may be generated based on one or more outputs 606 (FIG. 6) of wellness evaluation system 602. For instance, companion application 324 (FIG. 3) or third-party companion application 424 (FIG. 4) may generate GUI 1100.

In the example of FIG. 11, GUI 1100 includes controls 1102 that allow a user to switch between a user interface for display of a brain wellness score and a user interface for display of a body wellness score. The brain wellness score and the body wellness score may be two different wellness measures. In the example of FIG. 11, the brain wellness score is based on a use score sub-component, an engagement score sub-component, and an active listening sub-component. Wellness evaluation system 602 may determine the use score sub-component, the engagement score sub-component, and the active listening sub-component in the manner described in any of the examples provided elsewhere in this disclosure. Feature 1104 of GUI 1100 indicates a value of the use score sub-component. Feature 1106 of GUI 1100 indicates a value of the engagement score sub-component. Feature 1108 of GUI 1100 indicates a value of the active listening sub-component. In features 1104, 1106, and 1108 of GUI 1100, the value before the "/" mark indicates a current value of the sub-component and the value after the "/" mark indicates a target for the sub-component.

Furthermore, in the example of FIG. 11, GUI 1100 includes a circular diagram 1110 having segments corresponding to the sub-components of the brain wellness score. Each of the segments is filled in an amount proportional to the user's progress toward meeting the targets for the sub-components of the brain wellness score. Additionally, circular diagram 1110 may include a numerical value indicating the user's brain wellness score (e.g., 57 in the example of FIG. 11) and a numerical value indicating the user's target for the brain wellness score (e.g., 100 in the example of FIG. 11).

GUI 1100 also includes historical icons 1112A, 1112B, and 1112C (collectively, "historical icons 1112"). In the example of FIG. 11, like circular diagram 1110, historical icons 1112 include segments with filled portions corresponding to the user's progress toward meeting the goals for the sub-components on previous days, e.g., Saturday, Sunday and Monday in the example of FIG. 11. In response to receiving an indication of user selection of one of historical icons 1112, a computing device (e.g., computing device 300, third-party computing device 400, etc.) may output for display a GUI having more details regarding the user's brain wellness score for the day corresponding to the selected historical icon.

FIG. 12 is an example GUI 1200 for display of a body wellness score in accordance with one or more aspects of this disclosure. The body wellness score is one example of a wellness measure. GUI 1200 may be generated based on one or more outputs 606 (FIG. 6) of wellness evaluation system 602. For instance, companion application 324 (FIG. 3) or third-party companion application 424 may generate GUI In the example of FIG. 12, GUI 1200 includes controls 1202 that allow a user to switch between a user interface for display of the brain wellness score and a user interface for display of a body wellness score. In the example of FIG. 12, the body wellness score is based on a steps sub-component, an activity sub-component, and a movement sub-component. Wellness evaluation system 602 may determine the steps sub-component, the activity sub-component, and the movement sub-component in the manner described in any of the examples provided elsewhere in this disclosure. Feature 1204 of GUI 1200 indicates a value of the steps sub-component. Feature 1206 of GUI 1200 indicates a value of the activity sub-component. Feature 1208 of GUI 1200 indicates a value of the movement sub-component. In features 1204, 1206, and 1208 of GUI 1200, the value before the "/" mark indicates a current value of the sub-component and the value after the "/" mark indicates a goal for the sub-component.

Furthermore, in the example of FIG. 12, GUI 1200 includes a circular diagram 1210 having segments corresponding to the sub-components of the body wellness score. Each of the segments is filled in an amount proportional to the user's progress toward meeting the goals for the sub-components of the body wellness score. Additionally, circular diagram 1210 may include a numerical value indicating the user's body wellness score (e.g., 100 in the example of FIG. 12) and a numerical value indicating the user's body wellness score goal (e.g., 100 in the example of FIG. 12).

GUI 1200 also includes historical icons 1212A, 1212B, and 1212C (collectively, "historical icons 1212"). Like circular diagram 1210, historical icons 1212 include segments with filled portions corresponding to the user's progress toward meeting the goals for the sub-components on previous days, e.g., Saturday, Sunday and Monday in the example of FIG. 12. In response to receiving an indication of user selection of one of historical icons 1212, a computing device (e.g., computing device 300, third-party computing device 400, etc.) may output for display a GUI having more details regarding the user's brain wellness score for the day corresponding to the selected historical circular diagram.

FIG. 13 is an example GUI 1300 for display of a wellness measure in accordance with one or more aspects of this disclosure. In the example of FIG. 13, GUI 1300 includes a body wellness score feature 1302 and a brain wellness score feature 1304. Body wellness score feature 1302 is filled in an amount proportional to the user's progress toward meeting the user's target level of a body wellness score. Brain wellness score feature 1304 is filled in an amount proportional to the user's progress toward meeting the user's target level of a brain wellness score. Additionally, in the example of FIG. 13, GUI 1300 includes a wellness measure feature 1306 (e.g., indicated by "Thrive Score" in the example of FIG. 13) that includes a numeric value indicating the user's wellness measure. The wellness measure may be based on the body wellness score and the brain wellness score.

In the example of FIG. 13, GUI 1300 may be a primary screen of companion application 324 (FIG. 3) or third-party companion application 424 (FIG. 4). Because controlling the volume of hearing-assistance device(s) may be the feature for which the user uses companion application 324 the most, GUI 1300 may be designed to indicate the user's wellness measure along with volume controls 1308 in order to bring the user's wellness measure to the user's attention.

Figure 14:
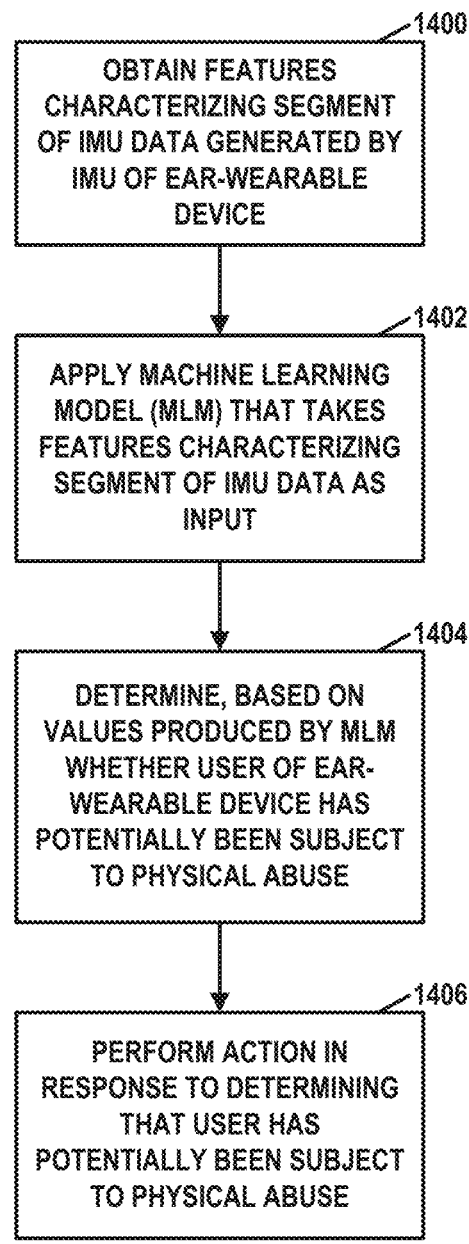
FIG. 14 is a flowchart illustrating an example operation of a wellness evaluation system to determine whether a user of an ear-wearable device has been potentially subject to a type of physical abuse, in accordance with one or more aspects of this disclosure.

FIG. 14 is a flowchart illustrating an example operation of wellness evaluation system 602 to determine whether a user of ear-wearable device(s) 102 has been potentially subject to a type of physical abuse, in accordance with one or more aspects of this disclosure.

In the example of FIG. 14, wellness evaluation system 602 may obtain a set of features characterizing a segment of IMU data generated by an IMU (e.g., IMU 220 (FIG. 2)) of an ear-wearable device (1400). In some examples, inputs 604 (FIG. 6, FIG. 7) may include the set of features characterizing the segment of IMU data. In some examples, inputs 604 may include a raw segment of IMU data (e.g., accelerometer signals, gyroscope signals, etc.). A data storage system (e.g., storage device(s) 316) may store the set of features characterizing a segment of inertial measurement unit (IMU) data generated by an IMU of an ear-wearable device.

A segment of data (e.g., a segment of IMU data) corresponds to a predefined time period, such as 1 second, 0.5 seconds, etc. The IMU data may include a set of acceleration signals. Each acceleration signal in the set of acceleration signals may correspond to a level of acceleration in a different axis. For instance, each of the acceleration signals may be generated by a different one of accelerometers 218 of IMU 220. In some examples, the IMU data may include a gyroscope signal or signals from other sensors of the IMU.

The set of features characterizing a segment of IMU data may include one or more of a variety of types of data. For example, the data characterizing a segment of IMU data may include, for each of the acceleration signals, one or more of a mean value of an acceleration signal within the segment, a standard deviation of the acceleration signal within the segment, a skewness of the acceleration signal within the segment, a kurtosis of the acceleration signal within the segment, a minimum value of the acceleration signal within the segment, a maximum value of the acceleration signal within the segment, a minimum absolute differential (i.e., slope) of the acceleration signal, a maximum absolute differential (i.e., slope) of the acceleration signal, a mean square differential of the acceleration signal, a spectral centroid of the acceleration signal, the last x number (e.g., 4, 3, 2, etc.) samples of raw data of the acceleration signal, and/or other features.

Wellness evaluation system 602 may obtain the segment of IMU data in one or more ways. For example, wellness evaluation system 602 may obtain the segment of IMU data from the ear-wearable device based on the segment of IMU data representing a level of acceleration above a predetermined threshold. That is, in this example, the ear-wearable device may generate and send the segment of IMU data to a computing system implementing system 600 (e.g., computing system 104 (FIG. 1)) in response to detecting an acceleration above a predetermined threshold. In this example, the system 600 may process the segment of IMU data to extract the set of features characterizing the segment of IMU data. For instance, in the context of FIG. 7, data preparation system 700 may process the segment of IMU data to generate the set of features characterizing the segment of IMU data.

Sending the segment of IMU data to the computing system in response to detecting an acceleration above the predetermined threshold may conserve battery power of the ear-wearable device. Routinely sending segments of the IMU data which are not associated with sufficient levels of acceleration to correspond to physical abuse may drain the battery power of the ear-wearable device.

Furthermore, in the example of FIG. 14, wellness evaluation system 602 may apply a machine learning model (MLM) that takes the features characterizing the segment of the IMU data as input (1402). In some examples, one or more of classification engines 702 (FIG. 7) may include the MLM. In some examples, machine learning system 706 (FIG. 7) implements the MLM. In some examples, the MLM is implemented outside the context of FIG. 7. The MLM may be implemented as an artificial neural network (ANN), a support vector machine, or another type of machine learning model.

In examples where the MLM is implemented as an ANN, the ANN may include input neurons. The input neurons of the ANN include input neurons that accept the set of features. The ANN also includes a plurality of output neurons. The plurality of output neurons may include a separate output neuron for each type of physical abuse in a plurality of types of physical abuse. In some examples, the plurality of output neurons may include an output neuron corresponding to no detected physical abuse. In some examples, the ANN does not include separate output neurons for different types of physical abuse. Rather, in such examples, the output neurons may include an output neuron that generates an output value that indicates in general whether the user has potentially been subject to physical abuse. In this example, the output neurons may also include an output neuron indicating whether the user has not been subject to physical abuse.

In addition to the input neurons and the output neurons, the ANN may include one or more hidden layers. Each of the hidden layers includes a set of artificial neurons. In an example where the ANN includes a single hidden layer and the input layer includes 234 input neurons, the hidden layer may include 200 artificial neurons. In this example, the ANN may be a fully connected artificial neural network. In other examples, the ANN may be another type of artificial neural network, such as a convolutional neural network, a recurrent neural network, or another type of ANN.

Applying the ANN comprises generating an output value for each of the output neurons of the ANN. For instance, in an example where the types of abuse include slapping, shaking, and throwing on a lower surface (e.g., a bed, floor, etc.), a first output neuron of the ANN may generate an output value corresponding to whether the user was slapped, a second output neuron of the ANN may generate an output value corresponding to whether the user was shaken, a third output neuron of the ANN may generate an output value corresponding to whether the user was thrown onto a lower surface, and a fourth output neuron of the ANN may generate an output value corresponding to whether the user was not subject to physical abuse during the time corresponding to the segment of the IMU data. Slapping, shaking, and throwing on a lower surface are three of the most common types of physical elder abuse, but it should be appreciated that there are many forms of physical elder abuse. For instance, punching, pushing, thrusting, etc. are other forms of physical abuse.

Figure 15:
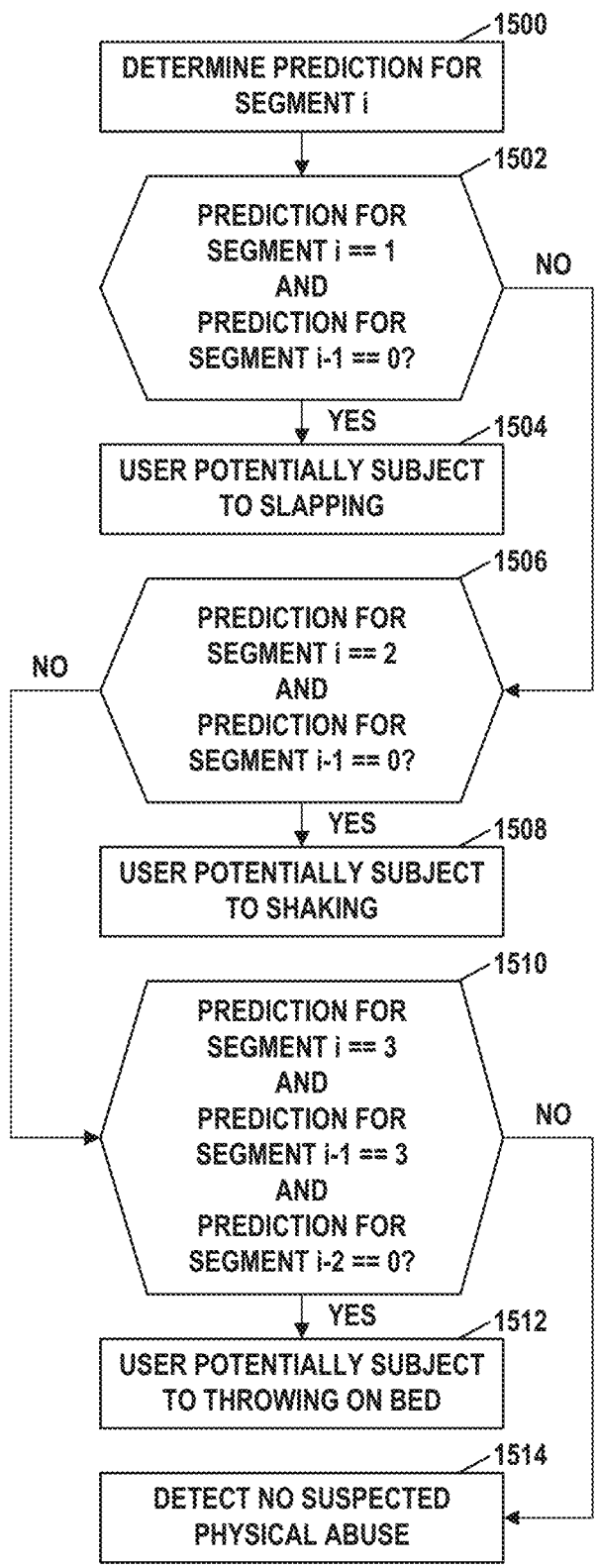
FIG. 15 is a flowchart illustrating an example operation of a system for determining a type of physical abuse to which the user may potentially have been subject, in accordance with one or more aspects of this disclosure.

Furthermore, in the example of FIG. 14, wellness evaluation system 602 may determine, based on the output values produced by the MLM, whether a user of the ear-wearable device has potentially been subject to physical abuse (1404). In an example where the MLM is implemented using an ANN, wellness evaluation system 602 may determine, based on output values produced by the output neurons of the ANN, whether the user has potentially been subject to physical abuse. For instance, in one example, the output neurons of the ANN may output numerical values, such as likelihood values, confidence values, scores, Boolean values, or other types of numerical values. In this example, wellness evaluation system 602 may determine which of the output neurons generated the largest numerical value. Furthermore, in this example, wellness evaluation system 602 may determine that the user was potentially subject to a type of abuse if the output neuron that generated the largest numerical value corresponds to the type of abuse. For instance, if the output neuron corresponding to slapping generated the largest numerical value, wellness evaluation system 602 may determine that the user was potentially subject to slapping. FIG. 15, which is described in greater detail elsewhere in this disclosure, describes an example operation for determining a type of physical abuse to which the user may potentially have been subject.

In some examples, inputs to the MLM may include features characterizing one or more other types of data than IMU data. For example, inputs to the MLM may include features characterizing audio data. The audio data may include audio detected by one or more microphones of ear-wearable device(s) 102 (e.g., microphones 208 (FIG. 2)). Features characterizing the audio data may include words detected in the audio data, data characterizing an emotional content of the audio data, distance to a sound source in the audio data, direction to a sound source in the audio data, and so on. Thus, wellness evaluation system 602 may obtain a second set of features, wherein the second set of features characterizes a segment of audio data generated by the ear-wearable device or another ear-wearable device concurrently worn by the user. In this example, the MLM takes the first set of features and the second set of features as input. In the context of FIG. 7, data preparation system 700 may extract the features. In some examples, one or more of ear-wearable device(s) 102 may extract features from the audio data.

In some examples, the other types of data used as input to the MLM may include heart rate data, galvanic skin response data, and/or other types of data. The signals from these sensors may provide secondary indications of whether the user was potentially subject to physical abuse. For example, physical abuse or other danger is associated with increased heart rate and sweat production, which may be measured by the heart rate sensor and galvanic skin response sensor, respectively. Features characterizing data from the other sensors may include a heart rate of the user, characteristics of the electrodermal activity, and so on. In some examples, one or more of ear-wearable device(s) 102 extracts some or all of the features. In the context of FIG. 7, data preparation system 700 may extract the features.

In some examples, rather than a single MLM (e.g., a single ANN) receiving features characterizing IMU data, audio data, and/or data from other sensors, two or more separate MLMs (e.g., two or more separate ANNs) may be used for determining that the user was potentially subject to physical abuse. For instance, a first MLM may determine based on features characterizing IMU data whether the user was potentially subject to physical abuse, a second MLM may determine based on features characterizing audio data whether the user was potentially subject to physical abuse, and so on. In such examples, the different MLMs may be instances of different classification engines 702 (FIG. 7). In some examples, wellness evaluation system 602 may determine that the user was potentially subject to a type of physical abuse if the multiple MLMs agree.

For instance, in examples where there are multiple MLMs (e.g., multiple ANNs), wellness evaluation system 602 may obtain a second set of features (in addition to features characterizing the IMU data), wherein the second set of features characterizes a segment of audio data generated by the ear-wearable device or another ear-wearable device concurrently worn by the user. Wellness evaluation system 602 may make, based on the second set of features, a second determination of whether the user has been potentially subject to the type of physical abuse. For instance, wellness evaluation system 602 may use a second MLM to make the second determination. Furthermore, wellness evaluation system 602 may determine, based on the first determination and the second determination whether the user has been potentially subject to physical abuse (e.g., a particular type of physical abuse).

In the example of FIG. 14, wellness evaluation system 602 may perform one or more actions in response to determining that the user of ear-wearable device(s) 102 has potentially been subject to physical abuse (1406). In the context of FIG. 7, action engine 708 may perform the one or more actions in response to classification engines 702 and/or machine learning system 706 determining that the user of ear-wearable device(s) 102 has potentially been subject to physical abuse. In some examples, the action may be specific to a type of the potential physical abuse.

In one example of an action that wellness evaluation system 602 may take in response to determining that the user of ear-wearable device(s) 102 has potentially been subject to physical abuse, wellness evaluation system 602 may notify one or more other persons. Such other persons may include family members, law enforcement personnel, social workers, housing supervisors, health caregivers, or other types of individuals. Notification may take the form of application-based alerts, email messages, telephone calls, etc.

In another example of an action, wellness evaluation system 602 may instruct ear-wearable device(s) 102 to gather and/or transmit location data for ear-wearable device(s) 102. Thus, wellness evaluation system 602 may obtain location data for ear-wearable device(s) 102 in response to determining that the user of ear-wearable device(s) 102 has potentially been subject to the type of physical abuse. The location data may include satellite navigation system-based location data, such as Global Positioning System (GPS)-based location data. Continuous generation of satellite navigation system-based location may consume unnecessary amounts of power from a power source of an ear-wearable device. Thus, in accordance with a technique of this disclosure, an ear-wearable device may generate satellite navigation system-based location data when wellness evaluation system 602 determines that the user of the ear-wearable device has potentially been subject to physical abuse, thereby conserving power from the power source of the ear-wearable device.

In some examples, the location data may include wireless access point data. For instance, many facilities, such as nursing homes and assisted living centers, include wireless access points (e.g., WiFi routers) at relatively stable locations. By determining relative signal strengths from multiple wireless access points as measured by an ear-wearable device, a location of an ear-wearable device may be determined. This technique for determining a location of an ear-wearable device may be especially advantageous in an indoor environment where satellite navigation system-based location data may not provide sufficient accuracy. However, as with satellite navigation system-based location data, the collection and/or transmission of wireless access point-based location data may come at a cost in terms of consumption of power from a power source of an ear-wearable device.

In another example of an action, wellness evaluation system 602 may instruct ear-wearable device(s) 102 to send a list of wireless communication identifiers of devices detected may the ear-wearable device(s) 102. Thus, wellness evaluation system 602 may obtain a list of wireless communication identifiers of devices detected by ear-wearable device(s) 102 worn by the user in response to determining that the user was potentially subject to physical abuse. Example types of wireless communication identifiers may include Internet Protocol (IP) addresses, Media Access Control (MAC) addresses, Bluetooth™ addresses, or other types of data that identify devices for purposes of wireless communication. Because people commonly carry wireless devices around with them, collecting such wireless communication identifiers in the immediate aftermath of a potential incident of physical abuse may help to identify who was close to the user of ear-wearable device(s) 102 around the time of the potential incident of physical abuse.

In another example of an action, wellness evaluation system 602 may cause at least one of ear-wearable device(s) 102 to output an audible request for confirmation that the user was subject to physical abuse. Wellness evaluation system 602 may determine, based on data obtained from ear-wearable device(s) 102 in response to the audible request, that the user provided an indication that the user was or was not subject to physical abuse. Ear-wearable device(s) 102 may be uniquely situated for asking the user of ear-wearable device(s) 102 whether the user was subject to abuse because typically only the user of ear-wearable device(s) 102 would be able to hear or otherwise know that a system was inquiring about possible physical abuse.

In some examples, the response by the user of ear-wearable device(s) 102 may be non-verbal. Thus, wellness evaluation system 602 may determine, based on data obtained from ear-wearable device(s) 102 that the user provided a non-verbal indication that the user was or was not subject to physical abuse. For example, the response by the user may be a particular type of jaw movement or head movement that is detectable by IMUs of ear-wearable device(s) 102, but that might not be readily apparent as being a response. This may allow the user to provide the confirmation without the potential abuser knowing that the user is providing the response, thereby potentially decreasing danger to the user.

Figure 16:
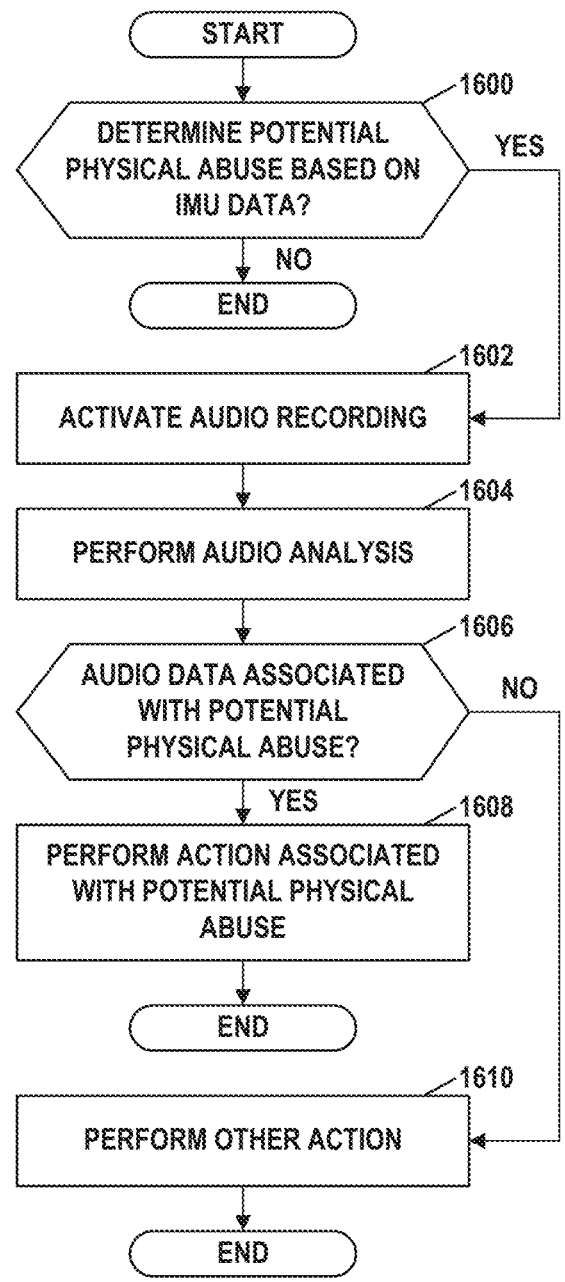
FIG. 16 is a flowchart illustrating an example operation of a system for determining whether to take an action associated with potential physical abuse of the user, in accordance with one or more aspects of this disclosure.

FIG. 15 is a flowchart illustrating an example operation of wellness evaluation system 602 for determining a type of physical abuse to which the user may potentially have been subject, in accordance with one or more aspects of this disclosure. In the example of FIG. 16, wellness evaluation system 602 may determine whether the user has potentially been subject to physical abuse based on a current segment and up to two previous segments.

As shown in the example of FIG. 16, wellness evaluation system 602 may determine a prediction value for a segment i (1500). Segment i may correspond to a current segment. The prediction value indicates a type of potential physical abuse or no physical abuse. In the example of FIG. 16, a prediction value equal to 0 corresponds to no physical abuse, a prediction value equal to 1 corresponds to slapping, a prediction value equal to 2 corresponds to shaking, and a prediction value equal to 3 corresponds to being thrown to a lower surface. In other examples, prediction values may have different meanings and/or may correspond to different types of potential abuse. Wellness evaluation system 602 may determine the prediction value for segment i in one of a variety of ways, such as by applying the MLM as described with respect to FIG. 14. Additionally, wellness evaluation system 602 may have determined prediction values for segments i−1 and i−2. Segment i−1 corresponds to a time before segment i and segment i−2 corresponds to a time before segment i−2.

Wellness evaluation system 602 may then determine whether the prediction value for segment i is equal to 1 and the prediction value for segment i−1 is equal to 0 (1502). If the prediction value for segment i is equal to 1 and the prediction value for segment i−1 is equal to 0 ("YES" branch of 1502), wellness evaluation system 602 may determine that the user was potentially subject to slapping (1504). This is because the acceleration associated with a slapping event typically occurs over a very short period of time (e.g., less than 0.5 seconds). In contrast, other types of head movements (e.g., nodding or shaking of the head) typically occur over longer periods of time.

Furthermore, in the example of FIG. 15, if the prediction value for segment i is not equal to 1 or the prediction value for segment i−1 is not equal to 0 ("NO" branch of 1502), wellness evaluation system 602 may determine whether the prediction value for segment i is equal to 2 and the prediction value for segment i−1 is equal to 0 (1506). In response to determining that the prediction value for segment i is equal to 2 and the prediction value for segment i−1 is equal to 0 ("YES" branch of 1502), wellness evaluation system 602 may determine that the user was potentially subject to shaking (1508). This is because the onset of acceleration associated with a shaking event typically occurs over a very short period of time (e.g., less than 0.5 seconds).

If the prediction value for segment i is not equal to 2 or the prediction value for segment i−1 is not equal to 0 ("NO" branch of 1506), wellness evaluation system 602 may determine whether the prediction value for segment i is equal to 3 and the prediction value for segment i−1 is equal to 3 and the prediction value for segment i−2 is equal to 0 (1510). In response to determining that the prediction value for segment i is equal to 3 and the prediction value for segment i−1 is equal to 3 and the prediction value for segment i−2 is equal to 0 ("YES" branch of 1510), wellness evaluation system 602 may determine that the user was potentially subject to being thrown on a lower surface (1512). Otherwise, in the example of FIG. 16, if the prediction value for segment i is not equal to 3 or the prediction value for segment i−1 is not equal to 3 or the prediction value for segment i−2 is not equal to 0 ("NO" branch of 1510), wellness evaluation system 602 may determine that the user was not subject to physical abuse (1514). This is because the acceleration associated with being thrown to a lower surface typically occurs over the span of two segments.

Thus, in the example of FIG. 15, wellness evaluation system 602 (which comprises one or more processing circuits) may obtain a set of features characterizing a segment of IMU data generated by an IMU of an ear-wearable device. Additionally, wellness evaluation system 602 may obtain a second set of features. The second set of features characterizes a first previous segment of IMU data generated by the IMU, where the first previous segment corresponds to a time before the current segment. Furthermore, wellness evaluation system 602 may obtain a third set of features. The third set of features characterizes a second previous segment of IMU data generated by the IMU, where the second previous segment corresponds to a time before the first previous segment. In this example, wellness evaluation system 602 may apply the MLM (e.g., ANN) to the second set of features to generate a second set of output values produced by the output neurons of the artificial neural network. Additionally, wellness evaluation system 602 may apply the MLM (e.g., ANN) to the third set of features to generate a third set of output values produced by the output neurons of the artificial neural network. To determine whether the user of the ear-wearable device has potentially been subject to the type of physical abuse comprises, wellness evaluation system 602 may determine that the user has potentially been subject to slapping based on the first set of output values indicating that the user has potentially been subject to slapping and the second set of output values indicating that the user has not been potentially subject to abuse. Wellness evaluation system 602 may determine that the user has potentially been subject to shaking based on the first set of output values indicating that the user has potentially been subject to shaking and the second set of output values indicating that the user has not been potentially subject to abuse. Wellness evaluation system 602 may determine that the user has potentially been subject to being thrown to the lower surface based on the first set of output values indicating that the user has potentially been subject to being thrown to the lower surface, the second set of output values indicating that the user has potentially been subject to being thrown to the lower surface, and the third set of output values indicating that the user has not been potentially subject to abuse.

FIG. 16 is a flowchart illustrating an example operation of wellness evaluation system 602 for determining whether to take an action associated with potential physical abuse of the user, in accordance with one or more aspects of this disclosure. The operation shown in the example of FIG. 16 may be implemented at least in part by action engine 708 of wellness evaluation system 602 of system 600 (FIG. 7). In the example of FIG. 16, wellness evaluation system 602 may determine, based on IMU data, that the user was potentially subject to physical abuse (1600). For instance, wellness evaluation system 602 may determine that the user was potentially subject to physical abuse based on the operation of FIG. 14. In response to determining based on the IMU data that the user was not potentially subject to physical abuse ("NO" branch of 1600), the operation of FIG. 16 may end and wellness evaluation system 602 does not take further action.

However, in response to determining based on the IMU data, that the user was potentially subject to physical abuse ("YES" branch of 1600), wellness evaluation system 602 may activate audio recording on one or more of ear-wearable device 102 (1602). In other words, wellness evaluation system 602 may activate recording of sound by one or more of ear-wearable device(s) 102 in response to determining that the user of ear-wearable device(s) 102 has potentially been subject to the type of physical abuse. A command to activate audio recording may be one of outputs 606 (FIG. 7). In the context of FIG. 6, the command to activate audio recording may be a type of sensor control. Ear-wearable device(s) 102 may be uniquely positioned to detect the sounds associated with physical or verbal abuse because they are not commonly covered in a way that muffles sound and because ear-wearable device(s) 102 may already include microphones designed to detect sounds perceived by the user. Additionally, ear-wearable devices are not commonly shared by different people, so it is unlikely that there will be any confusion about who was potentially subjected to physical abuse. Ear-wearable device(s) 102 are also advantageous in detecting many types of physical abuse because of their position on the user's head and the fact that many common types of physical abuse involve acceleration of the user's head. For instance, a wrist-worn accelerometer may not be able to detect slapping and the acceleration signals associated with shaking or being pushed to a lower surface may be damped by the time the acceleration signals reach the user's wrist due to actions of the arm muscles or whatever the user happens to be doing with their arms.

Moreover, in instances where the user wears two ear-wearable devices, the directionality of sound sources can be isolated. The directionality of a sound source can be determined in one or more ways. For instance, U.S. Patent Publication 2019/0253812, published Aug. 15, 2019, describes an example technique for determining a directionality of a sound source based on activation of periauricular muscles. In other examples, a head-related transfer function (HRTF) may be used to determine a directionality of a sound source. Determining the directionality of sound sources may be useful in determining whether the user has potentially been subject to physical abuse. For example, physical abuse is frequently associated with the abuser shouting. In cases of slapping, the abuser is frequently positioned perpendicular to the direction of acceleration of the user's head caused by the slap. In cases of shaking and being pushed to a lower surface, the abuser is typically positioned in parallel with the direction of acceleration of the user's head caused by the shaking or pushing. Thus, wellness evaluation system 602 may determine (e.g., determine with increased confidence) that the user of ear-wearable device(s) 102 has been subject to a type of physical abuse if the direction of acceleration associated with the type of physical abuse corresponds to a direction of the potential abuser's voice associated with that type of physical abuse. For instance, if wellness evaluation system 602 determines based on the IMU data that the user was potentially subject to slapping on the user's right cheek and a shouting sound is coming from a direction in front of the user, wellness evaluation system 602 may determine (e.g., determine with greater confidence) that the user was slapped.

Moreover, because of the separation of the two ear-wearable devices 102, a distance to a sound source may be determined based on audio recorded by ear-wearable devices 102. U.S. Patent Publication 2019/0253812, published Aug. 15, 2019, describes an example technique for determining a distance to a sound source based on activation of periauricular muscles. In other examples, the distance to the sound source may be determined in other ways. A potential abuser is frequently quite close to the user of ear-wearable device(s) 102 before, during, or after an act of potential physical abuse (e.g., less than 1 meter).

However, recording sound may consume additional power from a power source (e.g., battery 212 of FIG. 2) of an ear-wearable device. Moreover, analyzing and/or transmitting data based on the recorded sound may consume even more power from the power source of the ear-wearable device. Thus, it may not be desirable for the ear-wearable device to constantly record, analyze, and/or transmit sound or data characterizing the sound. It has been observed that the abuser typically continues shouting or otherwise vocalizing after performing an act of physical abuse. Accordingly, enough information may be obtained from audio recorded by ear-wearable device(s) 102 after a potential act of physical abuse to impact an ultimate determination that the user of ear-wearable device(s) 102 was potentially subject to a type of physical abuse. Not constantly recording sound may also improve privacy.

Furthermore, in the example of FIG. 16, wellness evaluation system 602 may perform audio analysis on the recorded audio (1604). In the context of FIG. 7, inputs 604 may include the audio data and data preparation system 700 may perform the audio analysis. In some examples, one or more of ear-wearable devices 102 performs some or all of the audio analysis on the recorded audio. In some such examples, one or more of ear-wearable devices 102 maintains a running buffer of audio data regardless of the detection of potential physical abuse, but only starts audio analysis and/or transmission of the audio data (or data resulting from audio analysis) in response to wellness evaluation system 602 determining based on the IMU data that the user of ear-wearable devices 102 was potentially subject to physical abuse.

Performing the audio analysis may include natural language processing. Natural language processing may include analyzing the audio data to identify words, sentences, screams, shouts, emotional association, and other aspects associated with semantic content of the recorded audio. Additionally, in some examples, performing audio analysis may include one or more of determining a direction or distance of a sound source.

Wellness evaluation system 602 may then determine whether the audio data is associated with potential physical abuse (1606). Thus, wellness evaluation system 602 may obtain a second set of features (e.g., features produced by the audio analysis) that characterize the recorded sound and may determine, based on the second set of features whether the user has potentially been subject to physical abuse.

In the context of FIG. 7, one or more of classification engines 702 may determine whether the audio data is associated with potential physical abuse. Wellness evaluation system 602 may determine that the audio data is associated with potential physical abuse in one or more of a variety of ways. For instance, in some examples, wellness evaluation system 602 may determine that the audio data is potentially associated with a type of physical abuse if the audio data contains a voice having a negative emotional context (e.g., anger, frustration, etc.), a source of the voice is in a direction consistent with the type of physical abuse potentially detected based on the IMU data, and the distance to the voice is less than a predetermined threshold. In other examples, one or more of these criteria may be omitted. In other examples, wellness evaluation system 602 may use other criteria.

If wellness evaluation system 602 determines that the audio data is associated with potential physical abuse ("YES" branch of 1606), wellness evaluation system 602 may perform an action associated with potential physical abuse (1608). In the context of FIG. 7, action engine 708 may perform an action based on a determination that the audio data is associated with potential physical abuse. Wellness evaluation system 602 may perform a variety of actions in response to determining that user of ear-wearable devices 102 has potentially been subject to physical abuse, such as any of the example actions provided elsewhere in this disclosure. For instance, wellness evaluation system 602 may generate notifications, request confirmation, and so on.

If wellness evaluation system 602 determines that the audio data is not associated with potential physical abuse ("NO" branch of 1606), wellness evaluation system 602 may perform some other action (1610). In other examples, wellness evaluation system 602 does not perform any action in response to determining that the audio data is not associated with potential physical abuse.

Neglect is another form of abuse. Neglect may be characterized by prolonged periods in which the victim does not move, has low social engagement from others, is provided food or beverages infrequently, prolonged periods in which the victim does not receive medicine on a regularity basis, prolonged periods in which the user is not bathed, and other situations in which a person fails to properly care for the victim. Neglect may be especially common among vulnerable populations, such as the elderly or people with disabilities. These vulnerable populations are also more likely than the general population to use ear-wearable devices, such as hearing aids. Ear-wearable devices may also be uniquely situated to detect instances of potential neglect.

In accordance with one or more techniques of this disclosure, wellness evaluation system 602 may detect potential instances of neglect. For instance, in some examples, wellness evaluation system 602 may receive input (e.g., input 604 (FIG. 6)) that includes data associated with one or more IMUs (e.g., IMU 220 (FIG. 2)) of hearing instrument(s) 102. Wellness evaluation system 602 may use the data associated with the IMUs to determine a level of movement of the user of ear-wearable device(s) 102. Furthermore, the data associated with the one or more IMUs indicating lack of motion may indicate that ear-wearable device(s) 102 are not being used and that a person has deprived the user of ear-wearable device(s) 102 of use of ear-wearable device(s) 102, which may itself be a form of improper care. Other types of sensors that may be used for determining whether ear-wearable device(s) 102 are being used may include electrodes, optical sensors, PPG sensors, magnetic field sensors, heart rate sensors, pressure sensors, blood perfusion sensors, capacitors, thermometers, etc.

As noted above, irregular provision of medication or other services may be a form of neglect. In accordance with a technique of this disclosure, wellness evaluation system 602 may be configured with a schedule of activities for the user of ear-wearable device(s) 102. The schedule may include events such as medication administration, bathroom trips, adjusting of the user's position in a bed (e.g., to prevent bedsores), food and liquid provision events, emesis events, and so on. Classification engines 702 may receive data associated with various sensors and determine based on the received data whether the events occurred as scheduled. For instance, if the user of ear-wearable device(s) 102 is to consume a pill a particular time of day, one or more of classification engines 702 may determine based on IMU data, audio data, and/or other types of data whether the user was provided the pill and consumed the pill.

In some examples, input 604 received by wellness evaluation system 602 may include data associated with microphones (e.g., microphone(s) 208 (FIG. 2)) of ear-wearable device(s) 102. The data associated with the microphones of ear-wearable device(s) 102 may include one or more of raw audio data generated by the microphones, statistical data based on sound captured by the microphones, and so on. Wellness evaluation system 602 may use the data associated with the microphones to detect sounds associated with care activities, such as bathing. In this example, one or more classification engines 702 (FIG. 7) and/or machine learning system 706 may be trained to recognize sounds associated with care activities. Alternatively or additionally, wellness evaluation system 602 may use the data associated with the microphones to determine levels of social engagement, e.g., as described elsewhere in this disclosure.

In some examples, input 604 received by wellness evaluation system 602 may include data regarding light levels, e.g., as detected by ear-wearable device(s) 102. One form of potential neglect is leaving lights off (e.g., keeping the user of ear-wearable device(s) 102 in the dark for prolonged amounts of time), leaving lights on (e.g., keeping the lights on when the user of ear-wearable device(s) 102 should be asleep), irregular timing of turning lights or off (e.g., indicative of sporadic care), and so on. Light sensors incorporated into ear-wearable device(s) 102 or accessory devices may generate such data. In some examples network-enabled lighting fixtures may provide operating time data. One or more classifications engines 702 of wellness evaluation system 602 may classify the light level data as indicative or not indicative of potential neglect.

Improper provision of food and liquids may be another form of neglect. Ear-wearable device(s) 102 may generate data indicative of food or liquid consumption. For example, IMU data may or other types of data generated by sensors (e.g., sensors for detecting changes of shape of the ear canal, internal microphones for detecting eating/drinking sounds, etc.) of ear-wearable device(s) 102 may be indicative or eating and drinking activities (e.g., jaw movement, swallowing, etc.). Classification engines 702 of wellness evaluation system 602 may be trained to recognize eating and drinking activities based on the provided input data.

In many cases, vulnerable individuals may be unable to put on their own ear-wearable devices or do not remember to do so. Similarly, vulnerable individuals may be unable to recharge their ear-wearable devices or do not remember to do so. In such cases, proper care of such an individual may involve putting in a user's ear-wearable devices and keeping the user's ear-wearable devices adequately charged. Accordingly, input 604 to wellness evaluation system 600 may include data associated with whether ear-wearable device(s) 102 are being worn. For example, input 604 may include IMU data and wellness evaluation system 600 may determine, based on the IMU data, whether ear-wearable device(s) 102 are being worn on a head of a user, e.g., as opposed to merely being powered-on but not used. To conserve battery power, wellness evaluation system 600 may disable other sensors of ear-wearable device(s) 102 (e.g., one or more of sensors 210 (FIG. 2)) in response to determining that the ear-wearable device(s) 102 are not being worn.

Furthermore, in some examples, input 604 to wellness evaluation system 600 may include data associated with charging statuses of the ear-wearable device(s) 102. For instance, input 604 may include data indicating times when ear-wearable device(s) 102 are recharged and/or times when battery levels of ear-wearable device(s) 102 reach specific thresholds (e.g., shutdown thresholds, low battery alert thresholds, etc.). In some examples, one or more charging accessory devices may generate data associated with charging statuses of ear-wearable device(s) 102. For example, a charging accessory may provide data indicating when batteries of ear-wearable device(s) 102 were recharged, data indicating that the charging accessory has not been used to recharge the batteries of ear-wearable device(s) 102 for at least a threshold amount of time, and so on.

Figure 17:
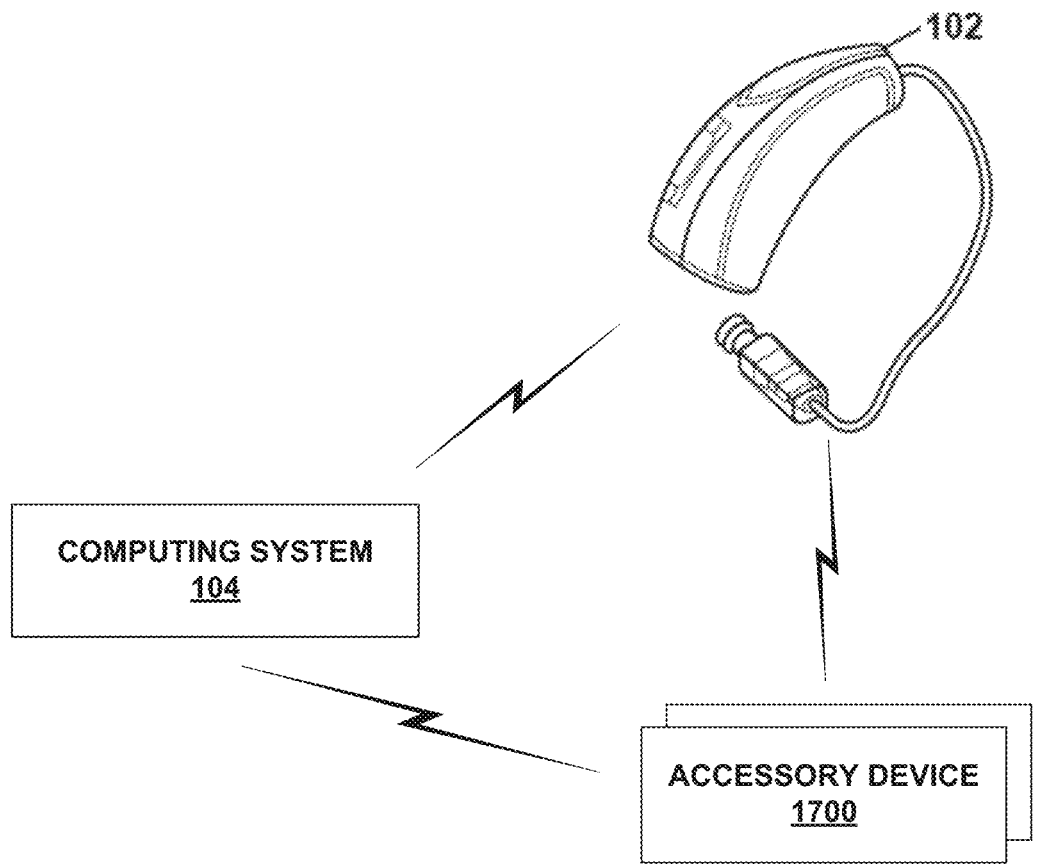
FIG. 17 is a conceptual diagram illustrating a system that includes ear-wearable device(s), a computing system, and one or more accessory devices, in accordance with one or more aspects of this disclosure.

FIG. 17 is a conceptual diagram illustrating a system that includes ear-wearable device(s) 102, computing system 104, and one or more accessory devices 1700, in accordance with one or more aspects of this disclosure. One or more accessory devices may be used ear-wearable device(s) 102. For instance, in the example of FIG. 17, one or more accessory devices 1700 may be used with ear-wearable device(s) 102. Example types of accessory devices 1700 may include charging cases, media streamer devices, remote microphone devices, and other types of devices configured to be used with ear-wearable device(s) 102. In some examples, one or more of accessory devices 1700 communicate with ear-wearable device(s) 102, e.g., through one or more wireless or non-wireless communication channels. Furthermore, in some examples, one or more of accessory devices 1700 may communicate with computing system 104, e.g., through one or more wireless or non-wireless communication channels. In some examples, ear-wearable device(s) 102 communicate with computing system 104 only through one or more of accessory devices 1700.

In some examples, one or more of accessory devices 1700 may generate input 604 to wellness evaluation system 600 in response to a determination that ear-wearable device(s) 102 are turned off or battery levels of ear-wearable device(s) 102 are allowed to reach specific thresholds (e.g., exhaustion thresholds, low battery alert thresholds, etc.). In some examples, this determination may be made by wellness evaluation system 600 and outputs 606 may include commands to one or more of accessory devices 1700 to start generating input 604. In some examples, this determination may be made by one or more of accessory devices 1700 without involvement of wellness evaluation system 600. Thus, wellness evaluation system 600 may continue to receive information about the user of ear-wearable device(s) 102 even if one or more of ear-wearable device(s) 102 is not operating. Example types of data that may be generated by accessory devices 1700 may include raw or processed audio data, light level data, motion sensing data, In some examples, ear-wearable device(s) 102 may continue to provide data to wellness evaluation system 600 even when ear-wearable device(s) 102 may appear to be powered-down (e.g., switched off or out of batteries). In such a state, specific functions of ear-wearable device(s) 102 may be turned off to conserve power and maintain the appearance of being powered-down. For instance, sound amplification may be turned off. One or more of accessory devices 1700 may also go into similar modes where the accessory devices 1700 appear to be powered-down but continue to provide data to wellness evaluation system 600. In some examples, one or more of accessory devices 1700 may start providing data to wellness evaluation system 600 in response to specific events, such as powering-down of one or more of ear-wearable device(s) 102, events detected by sensors of accessory devices 1700, and so on.

Wellness evaluation system 600 (e.g., machine learning system 706 of wellness evaluation system 600) may determine whether the user of ear-wearable device(s) 102 is potentially subject to neglect based on the frequency of movement, levels of social engagement, absence or infrequency of sounds associated with care activities, and so on. For instance, in some examples, classification engines 702 may take one or more types of data and generate classifications of the potential that the user is experiencing neglect. For instance, classification engines 702 may include an MLM (e.g., a neural network or other type of MLM) that has been trained to generate a numerical value indicative of a risk of potential neglect.

Outputs 606 of wellness evaluation system 602 may include commands to activate various types of sensors that generate data that wellness evaluation system 600 may use for assessing potential neglect. For example, outputs 606 may include a command to activate light sensors of ear-wearable device(s) 102 in response to wellness evaluation system 602 determining based on IMU data that there is a risk of neglect.

In some examples, wellness evaluation system 602 may generate one or more scores based on data associated with potential neglect. These scores may be presented by a companion application (e.g., third-party companion application 424 (FIG. 4), server companion application 524 (FIG. 5), etc.). Example scores may correspond to patterns or statistics related to the regularity of ear-wearable device(s) 102 being put on user, regularity of recharge of batteries of ear-wearable device(s) 102, regularity of light level cycles, regularity of food and beverage intake, levels of social engagement, levels of movement, etc. In some examples, wellness evaluation system 602 may generate a combined score (e.g., as a normalized sum of other scores) indicative of potential neglect. Scores may be presented to healthcare providers, family members, social workers, advocates, a user of ear-wearable device(s) 102, or other types of individuals.

Figure 18:
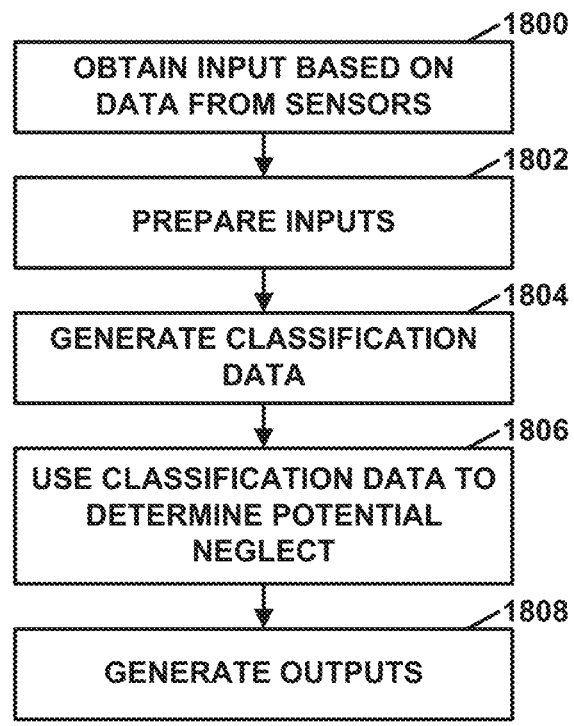
FIG. 18 is a flowchart illustrating an example operation for detecting potential neglect, in accordance with one or more aspects of this disclosure.

FIG. 18 is a flowchart illustrating an example operation for detecting potential neglect, in accordance with one or more aspects of this disclosure. In the example of FIG. 18, wellness evaluation system 602 may obtain inputs 604, which may be based on data from one or more sensors (e.g., one or more of sensors 210 (FIG. 2), sensors of one or more accessory devices 1700) (1800). For instance, in some examples, wellness evaluation system 602 may obtain one or more of inputs 604 from a data storage system, from a computer-readable medium, directly from a sensor, one or more accessory devices 1700, ear-wearable device(s) 102, or otherwise obtain inputs 604.

Furthermore, in the example of FIG. 18, data preparation system 700 of wellness evaluation system 602 may prepare inputs 604 for use in classification engines 702 (1802). Classification engines 702 may generate classification data based on the prepared inputs (1804). The classification data generated by classification engines 702 may include data associated with one or more characteristics of neglect (e.g., lack of movement, lack of regular provision of food and liquid, deprivation of use of ear-wearable devices, low social engagement, lack of regular provision of medicine, lack of regular bathing, and so on).

Wellness evaluation system 602 (e.g., machine learning system 706 of wellness evaluation system 602) may use the classification data to generate additional data regarding potential neglect (1806). In some examples, machine learning system 706 may use the classification data that is associated with characteristics of neglect to determine statistical data. Such statistical data may include statistics (e.g., averages, deviations, distributions, probabilities, etc.) of the characteristics of neglect. Additionally, in the example of FIG. 18, action engine 708 may generate outputs 606 (1808). Action engine 708 may generate one or more of outputs 606 based on the data regarding potential neglect. For instance, in some examples, action engine 708 may activate additional sensors, provide alerts, and so on. In one example, the classification data or data generated using the classification data may include one or more scores. In this example, if one or more of the scores exceed specific thresholds, action engine 708 may generate an alert.

The following paragraphs provided a non-limited set of enumerated examples in accordance with one or more techniques of this disclosure.

Example 1. A method comprising: obtaining, by one or more processing circuits, a set of features characterizing a segment of inertial measurement unit (IMU) data generated by an IMU of an ear-wearable device; applying, by the one or more processing circuits, a machine learning model (MLM) that takes the features characterizing the segment of the IMU data as input; determining, by the one or more processing circuits, based on output values produced by the MLM, whether a user of the ear-wearable device has potentially been subject to physical abuse; and performing, by the one or more processing circuits, an action in response to determining that the user of the ear-wearable device has potentially been subject to the type of physical abuse.

Example 2. The method of example 1, wherein: the MLM is an artificial neural network that includes a plurality of output neurons, the plurality of output neurons including a separate output neuron for each type of physical abuse in a plurality of types of physical abuse, applying the artificial neural network comprises generating an output value for each of the output neurons of the artificial neural network, and determining whether the user of the ear-wearable device has potentially be subject to physical abuse comprises: determining, by the one or more processing circuits, based on the output values produced by the output neurons of the artificial neural network, whether the user of the ear-wearable device has potentially been subject to a type of physical abuse in the plurality of the types of physical abuse.

Example 3. The method of example 2, wherein the plurality of types of physical abuse include one or more of slapping, shaking, or throwing to a lower surface.

Example 4. The method of any of examples 1-3, wherein: the segment is a current segment, the output values produced by the MLM are a first set of output values produced by the MLM, the method further comprises: obtaining, by the one or more processing circuits, a second set of features, the second set of features characterizing a first previous segment of IMU data generated by the IMU, wherein the first previous segment corresponds to a time before the current segment; obtaining, by the one or more processing circuits, a third set of features, the third set of features characterizing a second previous segment of IMU data generated by the IMU, wherein the second previous segment corresponds to a time before the first previous segment; applying the MLM to the second set of features to generate a second set of output values produced by the MLM; applying the MLM to the third set of features to generate a third set of output values produced by the MLM, and determining whether the user of the ear-wearable device has potentially been subject to physical abuse comprises: determining that the user has potentially been subject to slapping based on the first set of output values indicating that the user has potentially been subject to slapping and the second set of output values indicating that the user has not been potentially subject to abuse; determining that the user has potentially been subject to shaking based on the first set of output values indicating that the user has potentially been subject to shaking and the second set of output values indicating that the user has not been potentially subject to abuse; and determining that the user has potentially been subject to being thrown to the lower surface based on the first set of output values indicating that the user has potentially been subject to being thrown to the lower surface, the second set of output values indicating that the user has potentially been subject to being thrown to the lower surface, and the third set of output values indicating that the user has not been potentially subject to abuse.

Example 5. The method of any of examples 1-4, further comprising: obtaining, by the one or more processing circuits, the segment of IMU data from the ear-wearable device based on the segment of IMU data representing a level of acceleration above a predetermined threshold.

Example 6. The method of any of examples 1-5, wherein: the set of features is a first set of features, the method further comprises obtaining, by the one or more processing circuits, a second set of features, wherein the second set of features characterizes a segment of audio data generated by the ear-wearable device or another ear-wearable device concurrently worn by the user, and the MLM takes the first set of features and the second set of features as input.

Example 7. The method of any of examples 1-6, wherein: the determination based on the values produced by the MLM is a first determination, and the method further comprises: obtaining, by the one or more processing circuits, a second set of features, wherein the second set of features characterizes a segment of audio data generated by the ear-wearable device or another ear-wearable device concurrently worn by the user; making, by the one or more processing circuits, based on the second set of features, a second determination of whether the user has been potentially subject to physical abuse; and determining, by the one or more processing circuits, based on the first determination and the second determination whether the user has been potentially subject to physical abuse.

Example 8. The method of any of examples 1-7, further comprising activating, by the one or more processing circuits, recording of sound by the ear-wearable device or another ear-wearable device of the user in response to determining that the user of the ear-wearable device has potentially been subject to physical abuse.

Example 9. The method of example 8, wherein: the set of features is a first set of features, the method further comprises: obtaining, by the one or more processing circuits, a second set of features, wherein the second set of features characterizes the recorded sound; and determining, by the one or more processing circuits, based on the second set of features whether the user has potentially been subject to physical abuse.

Example 10. The method of any of examples 1-9, further comprising: obtaining, by the one or more processing circuits, location data for the ear-wearable device in response to determining that the user of the ear-wearable device has potentially been subject to physical abuse.

Example 11. The method of any of examples 1-10, further comprising: obtaining, by the one or more processing circuits, a list of wireless communication identifiers of devices detected by the ear-wearable device or another ear-wearable device worn by the user in response to determining that the user of the ear-wearable device has potentially been subject to physical abuse.

Example 12. The method of any of examples 1-11, further comprising: in response to determining that the user has potentially been subject to physical abuse, causing, by the one or more processing circuits, at least one of the ear-wearable device or another ear-wearable device worn by the user to output an audible request for confirmation that the user was subject to physical abuse; and determining, by the one or more processing circuits, based on data obtained from the ear-wearable device or the other ear-wearable device that the user provided an indication that the user was or was not subject to physical abuse.

Example 13. A system comprising: a data storage system configured to a set of features characterizing a segment of inertial measurement unit (IMU) data generated by an IMU of an ear-wearable device; and one or more processing circuits configured to: apply a machine learning model (MLM) that takes the features characterizing the segment of the IMU data as input, wherein: determine, based on output values produced by the MLM, whether a user of the ear-wearable device has potentially been subject to physical abuse; and perform an action in response to determining that the user of the ear-wearable device has potentially been subject to physical abuse.

Example 14. The system of example 13, wherein: the MLM is an artificial neural network that includes a plurality of output neurons, the plurality of output neurons including a separate output neuron for each type of physical abuse in a plurality of types of physical abuse, the one or more processing circuits are configured to generate an output value for each of the output neurons of the artificial neural network, and the one or more processing circuits are configured such that, as part of determining whether the user of the ear-wearable device has potentially be subject to physical abuse, the one or more processing circuits determine, based on the output values produced by the output neurons of the artificial neural network, whether the user of the ear-wearable device has potentially been subject to a type of physical abuse in the plurality of the types of physical abuse.

Example 15. The system of example 14, wherein the plurality of types of physical abuse include one or more of slapping, shaking, or throwing to a lower surface.

Example 16. The system of any of examples 13-15, wherein: the segment is a current segment, the output values produced by the MLM are a first set of output values produced by the MLM, the one or more processing circuits are further configured to: obtain a second set of features, the second set of features characterizing a first previous segment of IMU data generated by the IMU, wherein the first previous segment corresponds to a time before the current segment; obtain a third set of features, the third set of features characterizing a second previous segment of IMU data generated by the IMU, wherein the second previous segment corresponds to a time before the first previous segment; apply the MLM to the second set of features to generate a second set of output values produced by the MLM; apply the MLM to the third set of features to generate a third set of output values produced by the MLM, and the one or more processing circuits are configured such that, as part of determining whether the user of the ear-wearable device has potentially been subject to physical abuse, the one or more processing circuits: determine that the user has potentially been subject to slapping based on the first set of output values indicating that the user has potentially been subject to slapping and the second set of output values indicating that the user has not been potentially subject to abuse; determine that the user has potentially been subject to shaking based on the first set of output values indicating that the user has potentially been subject to shaking and the second set of output values indicating that the user has not been potentially subject to abuse; and determine that the user has potentially been subject to being thrown to the lower surface based on the first set of output values indicating that the user has potentially been subject to being thrown to the lower surface, the second set of output values indicating that the user has potentially been subject to being thrown to the lower surface, and the third set of output values indicating that the user has not been potentially subject to abuse.

Example 17. The system of any of examples 13-16, wherein the one or more processing circuits are further configured to: obtain the segment of IMU data from the ear-wearable device based on the segment of IMU data representing a level of acceleration above a predetermined threshold.

Example 18. The system of any of examples 13-17, wherein: the set of features is a first set of features, the one or more processing circuits are further configured to obtain a second set of features, wherein the second set of features characterizes a segment of audio data generated by the ear-wearable device or another ear-wearable device concurrently worn by the user, and the MLM takes the first set of features and the second set of features as input.

Example 19. The system of any of examples 13-18, wherein: the determination based on the values produced by the MLM is a first determination, and the one or more processing circuits are further configured to: obtain a second set of features, wherein the second set of features characterizes a segment of audio data generated by the ear-wearable device or another ear-wearable device concurrently worn by the user; make, based on the second set of features, a second determination of whether the user has been potentially subject to physical abuse; and determine, based on the first determination and the second determination whether the user has been potentially subject to physical abuse.

Example 20. The system of any of examples 13-19, wherein the one or more processing circuits are further configured to activate recording of sound by the ear-wearable device or another ear-wearable device of the user in response to determining that the user of the ear-wearable device has potentially been subject to physical abuse.

Example 21. The system of example 20, wherein: the set of features is a first set of features, the one or more processing circuits are further configured to: obtain a second set of features, wherein the second set of features characterizes the recorded sound; and determine, based on the second set of features, whether the user has potentially been subject to physical abuse.

Example 22. The system of any of examples 13-21, wherein the one or more processing circuits are further configured to: obtain location data for the ear-wearable device in response to determining that the user of the ear-wearable device has potentially been subject to physical abuse.

Example 23. The system of any of examples 13-22, wherein the one or more processing circuits are further configured to obtain a list of wireless communication identifiers of devices detected by the ear-wearable device or another ear-wearable device worn by the user in response to determining that the user of the ear-wearable device has potentially been subject to physical abuse.

Example 24. The system of any of examples 13-23, wherein the one or more processing circuits are further configured to: in response to determining that the user has potentially been subject to physical abuse, cause at least one of the ear-wearable device or another ear-wearable device worn by the user to output an audible request for confirmation that the user was subject to physical abuse; and determine, based on data obtained from the ear-wearable device or the other ear-wearable device that the user provided an indication that the user was or was not subject to physical abuse.

Example 25. A system comprising: means for obtaining a set of features characterizing a segment of inertial measurement unit (IMU) data generated by an IMU of an ear-wearable device; means for applying a machine learning model (MLM) that takes the features characterizing the segment of the IMU data as input; means for determining, based on output values produced by the MLM, whether a user of the ear-wearable device has potentially been subject to a type of physical abuse in the plurality of the types of physical abuse; and means for performing an action in response to determining that the user of the ear-wearable device has potentially been subject to the type of physical abuse.

Example 26. A computer-readable data storage medium having instructions stored thereon that, when executed, cause one or more processing circuits to: obtain a set of features characterizing a segment of inertial measurement unit (IMU) data generated by an IMU of an ear-wearable device; apply a machine learning model (MLM) that takes the features characterizing the segment of the IMU data as input; determine, based on output values produced by the MLM, whether a user of the ear-wearable device has potentially been subject to a type of physical abuse in the plurality of the types of physical abuse; and perform an action in response to determining that the user of the ear-wearable device has potentially been subject to the type of physical abuse.

In this disclosure, ordinal terms such as "first," "second," "third," and so on, are not necessarily indicators of positions within an order, but rather may be used to distinguish different instances of the same thing. Examples provided in this disclosure may be used together, separately, or in various combinations.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, an integrated circuit (IC) or a set of ICs (e.g., a chip set). Various components, modules, or units are described in this disclosure to emphasize functional aspects of devices configured to perform the disclosed techniques, but do not necessarily require realization by different hardware units. Rather, as described above, various units may be combined in a hardware unit or provided by a collection of interoperative hardware units, including one or more processors as described above, in conjunction with suitable software and/or firmware.

Various examples have been described. These and other examples are within the scope of the following claims.

What is claimed is:

1. A method comprising:
  obtaining, by one or more processing circuits, a first set of features characterizing a segment of inertial measurement unit (IMU) data generated by an IMU of an ear-wearable device;
  obtaining, by the one or more processing circuits, a second set of features, wherein the second set of features characterizes a segment of audio data generated by the ear-wearable device or another ear-wearable device concurrently worn by a user of the ear-wearable device;
  applying, by the one or more processing circuits, a machine learning model (MLM) that takes the first set of features and the second set of features as input;
  determining, by the one or more processing circuits, based on output values produced by the MLM, whether the user of the ear-wearable device has potentially been subject to improper care; and
  performing, by the one or more processing circuits, an action in response to determining that the user of the ear-wearable device has potentially been subject to improper care, wherein:

the MLM is an artificial neural network that includes a plurality of output neurons, the plurality of output neurons including a separate output neuron for each type of improper care in a plurality of types of improper care, applying the MLM comprises applying the artificial neural network, wherein applying the artificial neural network comprises generating an output value for each of the output neurons of the artificial neural network, and determining whether the user of the ear-wearable device has potentially been subject to improper care comprises determining, by the one or more processing circuits, based on the output values produced by the output neurons of the artificial neural network, whether the user of the ear-wearable device has potentially been subject to a type of improper care in the plurality of the types of improper care.

2. The method of claim 1, wherein the plurality of types of improper care include one or more of a prolonged period of the user not moving, a deviation from a schedule of activities associated with properly caring for the user, or depriving the user of the ear-wearable device.

3. The method of claim 2, wherein the schedule of activities includes one or more of medication administration, food and liquid provision events, emesis events, bathroom trips, or adjusting a position of the user in a bed.

4. The method of claim 1, wherein:
the segment of IMU data is a current segment of IMU data,
the output values produced by the MLM are a first set of output values produced by the MLM,
the method further comprises:
obtaining, by the one or more processing circuits, a third set of features, the third set of features characterizing a first previous segment of IMU data generated by the IMU, wherein the first previous segment of IMU data corresponds to a time before the current segment of IMU data;
obtaining, by the one or more processing circuits, a fourth set of features, the fourth set of features characterizing a second previous segment of IMU data generated by the IMU, wherein the second previous segment of IMU data corresponds to a time before the first previous segment of IMU data;
applying the MLM to the third set of features to generate a second set of output values produced by the MLM; and
applying the MLM to the fourth set of features to generate a third set of output values produced by the MLM, and
determining whether the user of the ear-wearable device has potentially been subject to improper care comprises:
determining that the user has potentially been subject to a prolonged period of not moving based on the first set of output values indicating that the user has potentially been subject to the prolonged period of not moving and the second set of output values indicating that the user has not been potentially subject to improper care;
determining that the user has potentially been subject to a deviation from a schedule of activities associated with properly caring for the user based on the first set of output values indicating that the user has potentially been subject to the deviation from the schedule of activities and the second set of output values indicating that the user has not been potentially subject to improper care; and
determining that the user has potentially been subject to deprivation of the ear-wearable device based on the first set of output values indicating that the user has potentially been subject to deprivation of the ear-wearable device and the second set of output values indicating that the user has not been potentially subject to improper care.

5. The method of claim 1, further comprising:
obtaining, by the one or more processing circuits, the segment of IMU data from the ear-wearable device based on the segment of IMU data representing a level of acceleration below a predetermined threshold for a prolonged period.

6. The method of claim 1, wherein:
the segment of audio data is a first segment of audio data,
the determination based on the output values produced by the MLM is a first determination, and
the method further comprises:
obtaining, by the one or more processing circuits, a third set of features, wherein the third set of features characterizes a second segment of audio data generated by the ear-wearable device or another ear-wearable device concurrently worn by the user;
making, by the one or more processing circuits, based on the third set of features, a second determination of whether the user has been potentially subject to improper care; and
determining, by the one or more processing circuits, based on the first determination and the second determination whether the user has been potentially subject to improper care.

7. The method of claim 1, further comprising activating, by the one or more processing circuits, recording of sound by the ear-wearable device or another ear-wearable device of the user in response to determining that the user of the ear-wearable device has potentially been subject to improper care.

8. The method of claim 7, wherein:
the method further comprises:
obtaining, by the one or more processing circuits, a third set of features, wherein the third set of features characterizes the recorded sound; and
determining, by the one or more processing circuits, based on the third set of features whether the user has potentially been subject to improper care.

9. The method of claim 1, further comprising:
obtaining, by the one or more processing circuits, location data for the ear-wearable device in response to determining that the user of the ear-wearable device has potentially been subject to improper care.

10. The method of claim 1, further comprising:
obtaining, by the one or more processing circuits, a list of wireless communication identifiers of devices detected by the ear-wearable device or another ear-wearable device worn by the user in response to determining that the user of the ear-wearable device has potentially been subject to improper care.

11. The method of claim 1, further comprising:
in response to determining that the user has potentially been subject to improper care, causing, by the one or more processing circuits, at least one of the ear-wearable device or another ear-wearable device worn by the user to output an audible request for confirmation that the user was subject to improper care; and determining, by the one or more processing circuits, based on data obtained from the ear-wearable device or the other ear-wearable device that the user provided an indication that the user was or was not subject to improper care.

12. A system comprising:
a data storage system configured to store:
a first set of features characterizing a segment of inertial measurement unit (IMU) data generated by an IMU of an ear-wearable device; and
a second set of features characterizing a segment of audio data generated by the ear-wearable device or another ear-wearable device concurrently worn by a user of the ear-wearable device; and
one or more processing circuits configured to:
apply a machine learning model (MLM) that takes the first set of features and the second set of features as input;
determine, based on output values produced by the MLM, whether the user of the ear-wearable device has potentially been subject to improper care; and
perform an action in response to determining that the user of the ear-wearable device has potentially been subject to improper care, wherein:
the MLM is an artificial neural network that includes a plurality of output neurons, the plurality of output neurons including a separate output neuron for each type of improper care in a plurality of types of improper care,
to apply the MLM, the one or more processing circuits are configured to apply the artificial network by generating an output value for each of the output neurons of the artificial neural network, and
the one or more processing circuits are configured such that, as part of determining whether the user of the ear-wearable device has potentially been subject to improper care, the one or more processing circuits determine, based on the output values produced by the output neurons of the artificial neural network, whether the user of the ear-wearable device has potentially been subject to a type of improper care in the plurality of the types of improper care.

13. The system of claim 12, wherein the plurality of types of improper care includes one or more of a prolonged period of the user not moving, a deviation from a schedule of activities associated with properly caring for the user, or depriving the user of the ear-wearable device.

14. The system of claim 13, wherein the schedule of activities includes one or more of medication administration, food and liquid provision events, emesis events, bathroom trips, or adjusting a position of the user in a bed.

15. The system of claim 12, wherein:
the segment of IMU data is a current segment of IMU data, the output values produced by the MLM are a first set of output values produced by the MLM,
the one or more processing circuits are further configured to:
obtain a third set of features, the third set of features characterizing a first previous segment of IMU data generated by the IMU, wherein the first previous segment of IMU data corresponds to a time before the current segment of IMU data;
obtain a fourth set of features, the fourth set of features characterizing a second previous segment of IMU data generated by the IMU, wherein the second previous segment corresponds to a time before the first previous segment;
apply the MLM to the third set of features to generate a second set of output values produced by the MLM;
apply the MLM to the fourth set of features to generate a third set of output values produced by the MLM, and
the one or more processing circuits are configured such that, as part of determining whether the user of the ear-wearable device has potentially been subject to improper care, the one or more processing circuits:
determine that the user has potentially been subject to a prolonged period of not moving based on the first set of output values indicating that the user has potentially been subject to the prolonged period of not moving and the second set of output values indicating that the user has not been potentially subject to improper care;
determine that the user has potentially been subject to a deviation from a schedule of activities associated with properly caring for the user based on the first set of output values indicating that the user has potentially been subject to the deviation from the schedule of activities and the second set of output values indicating that the user has not been potentially subject to improper care; and
determine that the user has potentially been subject to deprivation of the ear-wearable device based on the first set of output values indicating that the user has potentially been subject to deprivation of the ear-wearable device and the second set of output values indicating that the user has not been potentially subject to improper care.

16. The system of claim 12, wherein the one or more processing circuits are further configured to:
obtain the segment of IMU data from the ear-wearable device based on the segment of IMU data representing a level of acceleration below a predetermined threshold for a prolonged period.

17. The system of claim 12, wherein:
the segment of audio data is a first segment of audio data,
the determination based on the values produced by the MLM is a first determination, and
the one or more processing circuits are further configured to:
obtain a third set of features, wherein the third set of features characterizes a second segment of audio data generated by the ear-wearable device or another ear-wearable device concurrently worn by the user;
make, based on the second set of features, a second determination of whether the user has been potentially subject to improper care; and
determine, based on the first determination and the second determination whether the user has been potentially subject to improper care.

18. A non-transitory computer-readable data storage medium having instructions stored thereon that, when executed, cause one or more processing circuits to:
obtain a first set of features characterizing a segment of inertial measurement unit (IMU) data generated by an IMU of an ear-wearable device;
obtain a second set of features, wherein the second set of features characterizes a segment of audio data generated by the ear-wearable device or another ear-wearable device concurrently worn by a user of the ear-wearable device;

apply a machine learning model (MLM) that takes the first set of features and the second set of features as input;
determine, based on output values produced by the MLM, whether the user of the ear-wearable device has potentially been subject to improper care; and
perform an action in response to determining that the user of the ear-wearable device has potentially been subject to improper care, wherein:
　the MLM is an artificial neural network that includes a plurality of output neurons, the plurality of output neurons including a separate output neuron for each type of improper care in a plurality of types of improper care,
　to apply the MLM, the one or more processing circuits are configured to apply the artificial neural network by generating an output value for each of the output neurons of the artificial neural network, and
　the one or more processing circuits are configured such that, as part of determining whether the user of the ear-wearable device has potentially been subject to improper care, the one or more processing circuits determine, based on the output values produced by the output neurons of the artificial neural network, whether the user of the ear-wearable device has potentially been subject to a type of improper care in the plurality of the types of improper care.

\* \* \* \* \*